(12) United States Patent
Vogan et al.

(10) Patent No.: US 11,441,164 B2
(45) Date of Patent: Sep. 13, 2022

(54) BIOSYNTHETIC PRODUCTION OF PSILOCYBIN AND RELATED INTERMEDIATES IN RECOMBINANT ORGANISMS

(71) Applicant: CB Therapeutics, INC., Carlsbad, CA (US)

(72) Inventors: Jacob Michael Vogan, San Diego, CA (US); Laura Flatauer Peiffer, Carlsbad, CA (US); James Lee Wade, San Diego, CA (US); Tyrone Jacob Yacoub, Murrieta, CA (US); Kirsten Tang, Carlsbad, CA (US); Rachel Nadine Burnett, San Diego, CA (US)

(73) Assignee: CB THERAPEUTICS, INC., Carlsbad, CA (US)

( * ) Notice: Subject to any disclaimer, the term of this patent is extended or adjusted under 35 U.S.C. 154(b) by 0 days.

(21) Appl. No.: 17/099,539

(22) Filed: Nov. 16, 2020

(65) Prior Publication Data
US 2021/0147888 A1    May 20, 2021

Related U.S. Application Data

(60) Provisional application No. 62/936,387, filed on Nov. 15, 2019.

(51) Int. Cl.
*C12P 17/10*   (2006.01)
*C12N 9/88*    (2006.01)
(Continued)

(52) U.S. Cl.
CPC .............. *C12P 17/10* (2013.01); *C12N 1/16* (2013.01); *C12N 9/0083* (2013.01);
(Continued)

(58) Field of Classification Search
CPC ...... C12N 9/88; C12N 9/0014; C12N 9/1217; C12N 9/1007; C12N 9/0083; C12N 9/1205; C12P 17/10
See application file for complete search history.

(56) References Cited

U.S. PATENT DOCUMENTS 10,435,727 B2 †  10/2019  Butt
11,136,293 B2 *  10/2021  Protzko ............... C12Y 207/01
(Continued)

FOREIGN PATENT DOCUMENTS

WO      2019180309 A1 †   9/2019
WO   WO-2019173797 A1 *   9/2019  .............. C12P 17/10
WO      2021086513 A1 †   5/2021

OTHER PUBLICATIONS

Hoefgen. Facile assembly and fluorescence-based screening method for heterologous expression of biosynthetic pathways in fungi. Metabolic Engineering. Volumn 48, Jul. 2018, pp. 44-51.*

(Continued)

*Primary Examiner* — Yong D Pak
(74) *Attorney, Agent, or Firm* — Torrey Pines Law Group, PC

(57) ABSTRACT

The systems and methods herein include engineering a host to produce psilocybin using engineered enzymes, genetic changes, and exogenous psilocybin precursor addition (e.g., addition of L-tryptophan to a growing culture of a psilocybin producing recombinant host strain). The process occurs in genetically engineered host cell(s) that can produce psilocybin.

12 Claims, 10 Drawing Sheets

Specification includes a Sequence Listing.

(51) Int. Cl.
   C12N 9/02      (2006.01)
   C12N 9/12      (2006.01)
   C12N 9/10      (2006.01)
   C12N 1/20      (2006.01)
   C12N 15/00     (2006.01)
   C12N 1/16      (2006.01)
   C12N 15/81     (2006.01)

(52) U.S. Cl.
   CPC ......... *C12N 9/1007* (2013.01); *C12N 9/1085* (2013.01); *C12N 9/1205* (2013.01); *C12N 9/88* (2013.01); *C12N 15/81* (2013.01); *C12Y 205/01054* (2013.01)

(56) References Cited

U.S. PATENT DOCUMENTS

| | | | |
|---|---|---|---|
| 2010/0205690 | A1 | 8/2010 | Bläsing et al. |
| 2014/0245496 | A1 | 8/2014 | Hansen et al. |
| 2016/0083722 | A1 | 3/2016 | Young et al. |
| 2016/0298151 | A1 † | 10/2016 | Butt |
| 2021/0010015 | A1 * | 1/2021 | Mojzita ............ C12N 15/52 |
| 2021/0108238 | A1 * | 4/2021 | Protzko .......... C12Y 114/16004 |

OTHER PUBLICATIONS

Borodina. Advances in metabolic engineering of yeast *Saccharomyces cerevisiae* for production of chemicals. Biotechnol. J. 2014, 609-620.*

Averesch et al., Metabolic Engineering of the Shikimate Pathway for Production of Aromatics and Derived Compounds • Present and Future Strain Construction Strategies. Front Bioeng Biotechnol. 2018, vol. 6: 32. PDF File: p. 1-19.

Chubukov et al., Synthetic and systems biology for microbial production of commodity chemicals. NPJ Syst Biol Appl. 2016, vol. 2: 16009. PDF File: p. 1-11.

GenBank_KY984101, Psilocybe cubensis strain FSU 12409 tryptophan decarboxylase (psiD) mRNA, complete eds. GenBank Accession No. Aug. 26, 2017. (online]. [Retrieved on Feb. 8, 2021]. Retrieved from the Internet.

GenBank_LR732084, Armillaria ostoyae strain C18/9 genome assembly, chromosome: LG10. Oct. 21, 2019. [Online]. [Retrieved on Feb. 8, 2021]. Retrieved from the Internet: < URL: https://www.ncbi.nlm.nih.gov/nuccore/LR732084.

International Search Report and Written Opinion dated May 18, 2021 for PCT/US20/60788, 10 pages.

Milne et al., Metabolic engineering of *Saccharomyces cerevisiae* for the de novo production of psilocybin and related tryptamine derivatives. Metab Eng. 2020, vol. 60, p. 25-36.

Reynolds et al., Horizontal gene cluster transfer increased hallucinogenic mushroom diversity. Evol Lett. 2018, vol. 2(2), p. 88-101.

UniProtKB_A0A409VZH1, PSDC domain-containing protein. Last Modified: May 8, 2019. [online]. [Retrieved on Feb. 8, 2021]. Retrieved from the Internet: < URL: https://www.uniprot.org/uniproUA0A409VZH1 >.

Fricke et al, "Enzymatic synthesis of psilocybin" Angew. Chem. Int. Ed. 10.1002/anie.201705489.

Fricke et al, "Enzymatic synthesis of psilocybin—Supporting Information" Angew. Chem. Int. Ed. 10.1002/ anie.201705489.

Fricke, J., Blei, F., Hoffmeister, D. (2017). Enzymatic synthesis of psilocybin. Angewandte Chemie Int. Ed. 56, 12352-12355.†

Niederberger, P., Aebi, M., Furter, R., Prantl, F., & Hütter, R. (1984). Expression of an artificial yeast TRP-gene cluster in yeast & *Escherichia coli*. Mol. & gen. genetics: MGG, 195(3), 481-486.†

Hoefgen, S., Lin, J., Fricke, J., Stroe, M. C., Mattern, D. J., Kufs, J. E., Hortschansky, P., Brakhage, A. A., Hoffmeister, D., & Valiante, V. (2018). Facile assembly and fluorescence-based screening method for heterologous expression of biosynthetic pathways in fungi. Metab. Eng'g. 48, 44-51.†

Lanza, A. M., Curran, K. A., Rey, L. G., & Alper, H. S. (2014). A condition-specific codon optimization approach for improved heterologous gene expression in *Saccharomyces cerevisiae*. BMC systems biology, 8, 33.†

\* cited by examiner
† cited by third party

AMINO ACID TABLE

| Full Name | Abbreviation(3 Letter) | Abbreviation(1 Letter) |
|---|---|---|
| Alanine | Ala | A |
| Arginine | Arg | R |
| Asparagine | Asn | N |
| Aspartate | Asp | D |
| Aspartate or Asparagine | Asx | B |
| Cysteine | Cys | C |
| Glutamate | Glu | E |
| Glutamine | Gln | Q |
| Glutamate or Glutamate | Glx | Z |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

NUCLEIC ACID TABLE

| First Base In Codon | Second Base In Codon: U | C | A | G |
|---|---|---|---|---|
| U | UUU, UUC } Phe<br>UUA, UUG } Leu | UCU, UCC, UCA, UCG } Ser | UAU, UAC } Tyr<br>UAA TERM<br>UAG TERM | UGU, UGC } Cys<br>UGA TERM<br>UGG Trp |
| C | CUU, CUC, CUA, CUG } Leu | CCU, CCC, CCA, CCG } Pro | CAU, CAC } His<br>CAA, CAG } Gln | CGU, CGC, CGA, CGG } Arg |
| A | AUU, AUC, AUA } Ile<br>AUG Met | ACU, ACC, ACA, ACG } Thr | AAU, AAC } Asn<br>AAA, AAG } Lys | AGU, AGC } Ser<br>AGA, AGG } Arg |
| G | GUU, GUC, GUA, GUG } Val | GCU, GCC, GCA, GCG } Ala | GAU, GAC } Asp<br>GAA, GAG } Glu | GGU, GGC, GGA, GGG } Gly |

FIG. 1

| Gene/Enzyme | Function | Further description | Example Gane Source Organism |
|---|---|---|---|
| PsiD | decarboxylase | L-tryptophan decarboxylase | Psilocybe_cubensis, Psilocybe_cyanescens, Gymnopilus_junonius |
| PsiH | monooxygenase | Tryptamine 4-monooxygenase | Psilocybe_cubensis, Psilocybe_cyanescens, Gymnopilus_junonius |
| PsiK | kinase | 4-hydroxytryptamine kinase | Psilocybe_cubensis, Psilocybe_cyanescens |
| PsiM | methyl transferase | Psilocybin synthase | Psilocybe_cubensis, Psilocybe_cyanescens, Panaeolus_cyanescens, Gymnopilus_junonius, Gymnopilus_dilepis |

FIG. 2

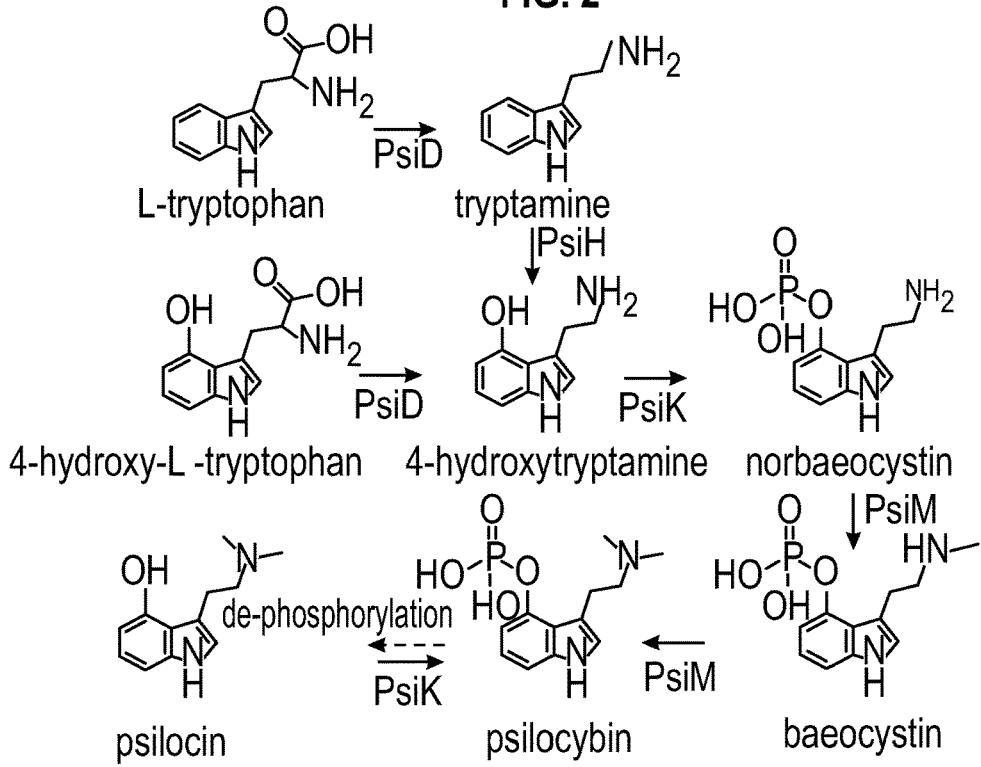

FIG. 3

Multiple-sequence alignment recombinant PsiD enzymes

```
Psilocybe_cubensis_PSID      MQVIPACNSAAIRSLCPTPESFRNMGWLSVSDAVYSEFIGELATRASNRNYSNEFGLMQP 60
Psilocybe_cyanescens_PSID    MQVLPACQSSALKTLCPSPEAFRKLGWLPTSDEVYNEFIDDLTGRTCNEKYSSQVTLLKP 60
Gymnopilus_junonius_PSID     -------------MSSPRIVLHRVGGWLPKDQNVLEAWLSKKIAKAKTRNR-APKDWAPV 46
                                          .*    .* ***   .:  * . ::..   ::  ..:

Psilocybe_cubensis_PSID      IQEFKAFIESDPVVHQEFIDMFEGIQDS-------------PRNYQELCNMFNDIFRKAP 107
Psilocybe_cyanescens_PSID    IQDFKTFIENDPIVYQEFISMFEGIEQS-------------PTNYHELCNMFNDIFRKAP 107
Gymnopilus_junonius_PSID     IQDFQRLIETDAEIYMGFHQMFEQVPKKTPYDKDPTNEQWQVRNYMHMLDLFDLIITEAP 106
                             **:*: :**.*  ::   * .***  :  ..            **  .: ::* *: :**

Psilocybe_cubensis_PSID      VYGD---LGPPVYMIMAKLMNTRAGFSAFTRQRLNLHFKKLFDTWGLFLSSKDSRNVLVA 164
Psilocybe_cyanescens_PSID    LYGD---LGPPVYMIMARIMNTQAGFSAFTKESLNFHFKKLFDTWGLFLSSKNSRNVLVA 164
Gymnopilus_junonius_PSID     DFEQNDLVGFPINAILDWPMGTPGGLTAFINPKVNIMFHKMFDVWAVFLSSPASCYVLN- 165
                              :     :* *: *:   *.*  ..:** .  .:* .:** *.**** *   * **

Psilocybe_cubensis_PSID      DQFDDRHCGWLNERALSAMVKHYNGRAFDEVFLCDKNAPYYGFNSYDDFFNRRFRNRDID 224
Psilocybe_cyanescens_PSID    DQFDDKHYGWFSERAKTAMMINYPGRTFEKVFICDEHVPYHGFTSYDDFFNRRFRDKDTD 224
Gymnopilus_junonius_PSID     ----TSDSGWFGPAATAAI------PNFKETFICDPSLPYLGYTSWDNFFTRLFRPGVR- 214
                                   .  **:.  *  :*:       *...*:** **  *:.*:*:**.* **

Psilocybe_cubensis_PSID      RPVVGGVNNTTLISAACESLSYNVSYDVQSLDTLVFKGETYSLKHLLNMDPFTPQFEHGS 284
Psilocybe_cyanescens_PSID    RPVVGGVTDTLIGAACESLSYNVSHNVQSLDTLVIKGEAYSLKHLLHNMDPFTPQFEHGS 284
Gymnopilus_junonius_PSID     -P-VEFPNNDAIVNSACESTVYNIAPNIKPLDKFWIKGEPYSLNHILNMDPYASQFVGGT 272
                              * *   .:  :::.: ****  **::  :::   **.: :*** ***.:.:***:: ** *:

Psilocybe_cubensis_PSID      ILQGFLNVTAYHRWHAPVNGTIVKIINVPGTYFAQAPSTIGDPIPDNDYDPPPYLKSLVY 344
Psilocybe_cyanescens_PSID    IIQGFLNVTAYHRWHSPVNGTIVKIVNVPGTYFAQAPYTIGSPIPDNDRDPPPYLKSLVY 344
Gymnopilus_junonius_PSID     ISQAFLSALNYHRWASPVNGNIVKVVNVPGIYYAESPVIGFGNPEG--PDPAAPNLSQGF 330
                             * *.**. **** .****.***::****** *:*:*  .   .  **      *  :

Psilocybe_cubensis_PSID      FSNIAARQIMFIEADNKEIGLIFLVFIGMTEISTCEATVSEGQHVNRGDDLGMFHFGGSS 404
Psilocybe_cyanescens_PSID    FSNIAARQIMFIEADNKDIGLIFLVFIGMTEISTCEATCCEGQHVNRGDDLGMFHFGGSS 404
Gymnopilus_junonius_PSID     ITAVAARALIFIEADPNIGLMCFVGVGMAEVSTCEVTVSVGDVVKKGDEIGMFHFGGGST 390
                             ::   *** ::  ****** :****:  :*   :  **:*.****.**   *:*** :.:********:.

Psilocybe_cubensis_PSID      FALGLRKDCRAEIVEKFIEPGTVIRINEVVAALKA  439
Psilocybe_cyanescens_PSID    FALGLRKDSKAKILEKFAKPGTVIRINELVASVRK  439
Gymnopilus_junonius_PSID     HCLIFRPQTKITFNPDYPVST-AVPLNAAVATVV-  423
                              ..*  :*  :    :    .:    .:  :*  **::
```

EMBOSS Needle Pairwise Sequence Alignment statistics (using EBLOSUM62) with Psilocybe Cubensis (PSID gene) as reference

| GENE USED IN PAIRWISE ALIGNMENT (VS. PSILOCYBE CUBENSIS (PSID GENE)) | IDENTITY % | SIMILARITY % |
|---|---|---|
| PSILOCYBE CUBENSIS (PSID GENE) | 100.0 | 100.0 |
| PSILOCYBE CUBENSIS (PSID GENE) | 78.1 | 90.7 |
| GYMNOPILUS JUNONIUS (PSID GENE) | 36.2 | 52.2 |

FIG. 4

Multiple-sequence alignment recombinant PsiD enzymes

```
Psilocybe_cubensis_PSIH    ---------------MIAVLFSFVIAGCIYYIVSRRVRRSRLPPGIPIPFIGNMFEESPW 51
Psilocybe_cyanescens_PSIH  -MAPLI--TMIPIVLSLLIAGCIYYINARRIKRSRLPPGPPGIPIPFIGNMFDMFSESPW 57
Gymnopilus_junonius_PSIH   MMSEMNGMDKLALLTTLLAAGFLYFKNKRR-SAIPFPPGP--KKHPLLGNLLDLPKKLEW 57
                                          :  :: ::: ** :*:   **   :****  *:::**::*:*..: *

Psilocybe_cubensis_PSIH    LTFLQWGRDYNTDILYVDAGGTEMVIINTLETIIDLLEKRGSIYSGRLESTMVNELMGWE 111
Psilocybe_cyanescens_PSIH  LIFLQWGQEYQTDIIYVDAGGTDMIIINSLEAIIDLLEKRGSLYSGRLESTMVNELMGWE 117
Gymnopilus_junonius_PSIH   ETYRRWGKEYNSDVIHVSAGSVNLIIVNSFEAATDLFDKRSANYSSRPQFTMVRELMGWN 117
                            : ,**::*::*.**  **..::*.*::*..:   **, *  :   ***.*****:

Psilocybe_cubensis_PSIH    FDLGFITYGDRWREERRMFAKEFSEKGIKQFRHAQVKAAHCLVQQLTKTPDRWACHIRHQ 171
Psilocybe_cyanescens_PSIH  FDLGFITYGDRWREERRMFAKEFSEKGIKQFRHAQVKAANCLVROLTDKPDRWSHHIRHO 177
Gymnopilus_junonius_PSIH   WLMSALIYGDKWREQRRLFCKHFSTTNAELYQNIQLEYVRKALQHLLEEPSDFMGITRHM 177
                           : :,   : **::***:**:* *.**  .. . ::::*::  ,.: :::*  . *.  **

Psilocybe_cubensis_PSIH    IAAMSLDIGYGIDLA-EDDPWLEATHLANEGLAIASVPGKFWVDSFPSLKYLPAWFPGAV 230
Psilocybe_cyanescens_PSIH  IASMALDIGYGIDLA-EDDPWIAASELANEGLAVASVPGSFWVDTFPFLKYLPSWLPGAE 236
Gymnopilus_junonius_PSIH   AGGVSMSLAYGLNIQKKNDPFVDLAQRAVHSITEASVPGTFWVDVMPWLKYIPEWVPGAG 237
                             ..::::.**::: ::*::   :. *  ..:: *****.****.:* ***:* *.***

Psilocybe_cubensis_PSIH    FKRKAKVWREAADHMVDMPYETMRKLAPQGLTRPSYASARLQAMDLNGDLEHQEHVIKNT 290
Psilocybe_cyanescens_PSIH  FKRNAKMWKEGADHMVNMPYETMKKLSAQGLTRPSYASARLQAMDPNGDLEHQERVIKNT 296
Gymnopilus_junonius_PSIH   FQKKARVWRKLQQDFRQVPYQAALKDMASGKAKPSFASECLETIDDNEDAQRQREVIKDT 297
                           *:::*::**::  ..: ::**:.  *  .* ::**:**  *:::* * * ::*.***:*

Psilocybe_cubensis_PSIH    AAEVNVGGGDTTVSAMSAFILAMVKYPEVQRKVQAELDALTNNGQIPDYDEEDDSLPYLT 350
Psilocybe_cyanescens_PSIH  ATQVNVGGGDTTVGAVSAFILAMVKYPEVQRKVQAELDEFTSKGRIPDYDEDNDSLPYLT 356
Gymnopilus_junonius_PSIH   AAIVFAAGADTSLSGIHTLFAAMLCYPEVQKKAQEELDRVLGGRRLPEFTDE-PNMPYIS 356
                           *:.* ..*.**::.: :::  ***:* ,* ***  . .::*::  ::  ..:**::

Psilocybe_cubensis_PSIH    ACIKELFRWNQIAPLAIPHKLMKDDVYRGYLIPKNTLVFANTWA---VLNDPEVYPDPSV 407
Psilocybe_cyanescens_PSIH  ACFKELFRWGQIAPLAIAHRLIKDDVYREYTIPKNALVFANNWYGRTVLNDPSEYPNPSE 416
Gymnopilus_junonius_PSIH   ALVKEILRWKPATPIGVPHLASEDDVYNGYYIPKRAVVIGNSWA---MLHDEETYPDPST 413
                           *  .**::**  :*.:. *   :****. * ***:::*:.*.*    :*:* . **:**

Psilocybe_cubensis_PSIH    FRPERYLGPDGK-----PDNTVRDPRKAAFGYGRRNCPGIHLAQSTVWIAGATLLSAFNI 462
Psilocybe_cyanescens_PSIH  FRPERYLGPDGK-----PDDTVRDPRKAAFGYGRRVCPGIHLAQSTVWIAGVALVSAFNI 471
Gymnopilus_junonius_PSIH   FNPDRFLTTNKSTGKLELDPTVRDPALMAFGFGRRMCPGRDVALSVIWLTIASVLATFNI 473
                           *.*:*:* :  :  ..  * *****   ***:***  .:* * .:*:: ::::::***

Psilocybe_cubensis_PSIH    ERPVDQNGKPIDIPADFTIGFFRHPVPFQCRFVPRTEQVSQSVSGP---- 508
Psilocybe_cyanescens_PSIH  ELPVDKDGKCIDIPAAFTTGFFR-------------------------- 494
Gymnopilus_junonius_PSIH   TKAIDENGKELEPDVQYWSGLIVHPLPFKCTIKPRSKAAEELVKSGADAY 523
                             :*:::**  ::   .  : :*::
```

EMBOSS Needle Pairwise Sequence Alignment statistics (using EBLOSUM62) with Psilocybe cubensis (PSIH gene) as reference

| GENE USED IN PAIRWISE ALIGNMENT (VS. PSILOCYKE CUBENSIS (PSIH GENE)) | IDENTITY % | SIMILARITY % |
|---|---|---|
| PSILOCYKE CUBENSIS (PSIH GENE) | 100.0 | 100.0 |
| PSILOCYKE CYANESCENS (PSIH GENE) | 76.2 | 84.7 |
| GYMNOPILUS JUNONIUS (PSID GENE) | 39.3 | 61.1 |

FIG. 5

Multiple-sequence alignment recombinant PsiK enzymes

```
Psilocybe_cubensis_PSIK    MAFDLKTEDGLITYLTKHLSLDVDTSGVKRLSGGFVNVTWRIKLNAPYQGHTSIILKHAQ 60
Psiloybe_cyanescens_PSIK   MTFDLKTEEGLLSYLTKHLSLDVAPNGVKRLSGGFVNVTWRVGLNAPYHGHTSIILKHAQ 60
                           *.******.**..**********  .*************.  *****.***********

Psilocybe_cubensis_PSIK    PHMSTDEDFKIGVERSVYEYQAIKLMMANREVLGGVDGIVSVPEGLNYDLENNALIMQDV 120
Psiloybe_cyanescens_PSIK   PHLSSDIDFKIGVERSAYEYQAIKIVSANSSLIGSSDIRVSVPEGLHYDVVNNALIMQDV 120
                           **.*.* ********.******.*.:  **  .**. *   ******.**.. *******

Psilocybe_cubensis_PSIK    GKMKTLLDYVTAKPPLATDIARLVGTEIGGFVARLHNIGRERRDDPEFKFFSGNIVGRTT 180
Psiloybe_cyanescens_PSIK   GTMKTLLDYVTAKPPISAEIASLVGSQIGAFIARLHNLGRENKDDFKFFSGNIVGRTT 180
                           *.*************...:** ***..**.*.:*****.***..*. .************

Psilocybe_cubensis_PSIK    SDQLYQTIIPNAAKYGVDDPLLPTVVKDLVDDVMHSEETLVMADLWSGNILLQLEEGNPS 240
Psiloybe_cyanescens_PSIK   ADQLYQTIIPNAAKYGIDDPILPTVVKELVEEVMNSEETLIMADLWSGNILLQFDEN-ST 239
                           .***************.***.******:**:.**.*****.***********..*.  :

Psilocybe_cubensis_PSIK    KLQKIYILDWELCKYGPASLDLGYFLGDCYLISRFQDEQVGTTMRQAYLQSYARTSKHSI 300
Psiloybe_cyanescens_PSIK   ELTRIWLVDWELCKYGPPSLDMGYFLGDCFLVARFQDQLVGTSMRQAYLKSYARNVKEPI 299
                           :* .*:::.*********.***.******:*.****..***.*******.****.*.*

Psilocybe_cubensis_PSIK    NYAKVTAGIAAHIVMWTDFMQWGSEEERINFVKKGVAAFHDARGNNDNGEITSTLLKESS 360
Psiloybe_cyanescens_PSIK   NYAKATAGIGAHLVMWTDFMKWGNDEEREEFVKKGVEAFHEANEDNRNGEITSTLVKEAS 359
                           ****.****.**:*******.**..***.:******.***...*.*.*******:**:*

Psilocybe_cubensis_PSIK    TA  362
Psiloybe_cyanescens_PSIK   RT  361
                           :
```

EMBOSS Needle Pairwise Sequence Alignment statistics (using EBLOSUM62) with Psilocybe cubensis (PSIK Gene) as refernce

| GENE USED IN PAIRWISE ALIGNMENT (VS, PSILOCYBE CUBENSIS (PSIK GENE)) | IDENTITY % | SIMILARITY % |
|---|---|---|
| PSILOCYBE CUBENSIS (PSIK GENE) | 100.0 | 100.0 |
| PSILOCYBE CYANESCENS (PSIK GENE) | 73.5 | 87.8 |

FIG. 6

Multiple-sequence alignment recombinant PsiM enzymes

```
Psilocybe_cubensis_PSIM      MHIRNPYRTPIDYQALSEAFPPLKPFVSVNA-DGTSSVDLTIPEAQRAFTAALLHRDFGL 59
Psiloybe_cyanescens_PSIM     MHIRNPYRDGVDYQALSEAFPALKPHVTVNS-DNTTSIDFAVPEAQRLYTAALLHRDFGL 59
Panaeolus_cyanescens_PSIM    MHNRNPYRDVIDYQALSEAYPPLKPHVTVNA-DNTASIDLTIPEVQRQYTAALLHRDFGL 59
Gymnopilus_junonius_PSIM     MHSRNPYRSPPDFAALSAAYPPLSPYITTDLSSGRKTIDFRNEEAQRRLTEAIMLRDFGV 60
Gymnopilus_dilepis_PSIM      MHIRNPYLTPPDYEALAEAFPALKPYVTVNP-DKTTTTDFAIPEAQRLYTAALLYRDFGL 59
                             ** ****    *: **: *:* *.*.::.:  .  ::*:   *.**  * *:: ****:

Psilocybe_cubensis_PSIM      TMTIPEDRLCPTVPNRLNYVLWIEDIFNYTNKTLGLSDDRPIKGVDIGTGASAIYPMLAC 119
Psiloybe_cyanescens_PSIM     TITIPEDRLCPTVPNRLNYVLWVEDILKVTSDALGLPDNRQVKGIDIGTGASAIYPMLAC 119
Panaeolus_cyanescens_PSIM    TITIPEDRLCPTVPNRLNYVLWIEDIFQCTNKALGLSDDRPVKGVDIGTGASAIYPMLAC 119
Gymnopilus_junonius_PSIM     VLNIPSNRLCPPVPNRMNYVLWIQDIVYAHQTILGVS-SRRIRGLDIGTGATAIYPILAC 119
Gymnopilus_dilepis_PSIM      TITLPPDRLCPTVPNRLNYVLWIQDILQITSAALGLPEARQVKGVDIGTGAAAIYPILGC 119
                             .:.:* :**** ****:*****:**.      **:   * ::*:******.*****:*.*

Psilocybe_cubensis_PSIM      ARFKAWSMVGTEVERKCIDTARLNVVANNLQDRLSILETSIDGPILVPIFEA----TEEY 175
Psiloybe_cyanescens_PSIM     SRFKTWSMVATEVDQKCIDTARLNVIANNLQERLAIIATSVDGPILVPLLQA----NSDF 175
Panaeolus_cyanescens_PSIM    ARFKQWSMIATEVERKCIDTARLNVLANNLQDRLSILEVSVDGPILVPIFDTFERATSDY 179
Gymnopilus_junonius_PSIM     KKEQSWEMVATELDDYSYECACDNVSSNNMQTSIKVKKASVDGPILFPVE--------NQ 171
Gymnopilus_dilepis_PSIM      SLAKNWSMVGTEVEQKCIDIAEQNVISNGLQDRITITANTIDAPILLPLFEG----DSNF 175
                              : *.*:.**::   .   *  ** :*.:*  : :    ::*.***.*:        :

Psilocybe_cubensis_PSIM      EYEFIMCNPPFYDGAADMQTSDAAKGFGFGVGAPHSGTVIEM-STEGGESAFVAQMVRES 234
Psiloybe_cyanescens_PSIM     EYDFIMCNPPFYDGASDMQTSDAAKGFGFGVNAPHTGTVLEM-ATEGGESAFVAQMVRES 234
Panaeolus_cyanescens_PSIM    EFEFIMCNPPFYDGAADMQTSDAAKGFGFGVNAPHSGTVIEM-ATEGGEAAFVAQMVRES 238
Gymnopilus_junonius_PSIM     NFDFSMCNPPFYDGAADMETSQDAKGFGFGVNAPHTGTVVEM-ATDGGEAAFVSQMVRES 229
Gymnopilus_dilepis_PSIM      EWEFTMCNPPFYDGAADMWTSQDAKGFGFGVNAPHTGTVVEM-ATDGGEAAFVSQMVRES 234
                             :::*:*******.. :: * :*   : .* :*: :** ::*** .**.:**.**

Psilocybe_cubensis_PSIM      LKLRTRCRWYTSNLGKLKSLKEIVGLLKELEISNYAINEYVQGSTRRYAVAWSFTDIQLP 294
Psiloybe_cyanescens_PSIM     LNLQTRCRWFTSNLGKLKSLYEIVGLLREHQISNYAINEYVQGATRRYAIAWSFTDVRLP 294
Panaeolus_cyanescens_PSIM    MKLQTRCRWFISNLGKLKSLHEIVALLRESQITNYAINEYVQGTTRRYALAWSFTDIKLT 298
Gymnopilus_junonius_PSIM     ERLQTRCKWYTSMLGKMSSVSTIVQALRARSIMNYALTEFVQGQTRRWAIAWSFSDTHLP 289
Gymnopilus_dilepis_PSIM      LHLKTRCRWFISNLGKLKSLHEIVGLLREHQITNYAINEYVQGTTRRYAIAWSFTDLRLS 294
                              .*:***:*:** ***:.*: **  *: .* ***:.*:*** ***::**** * :*

Psilocybe_cubensis_PSIM      EELSRPSNPELSSLF---- 309
Psiloybe_cyanescens_PSIM     DHLSRPSNPDLSSLF---- 309
Panaeolus_cyanescens_PSIM    EELYRPSNPELGPLCSTFV 317
Gymnopilus_junonius_PSIM     DAVSRISS----------- 297
Gymnopilus_dilepis_PSIM      DHLPRPPNPDLSALF---- 309
                             :  *   .
```

EMBOSS Needle Pairwise Sequence Alignment statistics (using EBLOSUM62) with Psilocybe cubensis (PSIM gene) as refernce

| GENE USED IN PAIRWISE ALIGNMENT (VS, PSILOCYBE CUBENSIS (PSIM GENE)) | IDENTITY % | SIMILARITY % |
|---|---|---|
| PSILOCYBE CUBENSIS (PSIM GENE) | 100.0 | 100.0 |
| PSILOCYBE CYANESCENS (PSIM GENE) | 77.7 | 91.3 |
| PANAEOLUS CYANESCENS (PSIM GENE) | 82.0 | 90.2 |
| GYMNOPILUS JUNONIUS (PSIM GENE) | 47.4 | 67.0 |
| GYMNOPILUS DILEPIS (PSIM GENE) | 71.2 | 86.4 |

FIG. 7

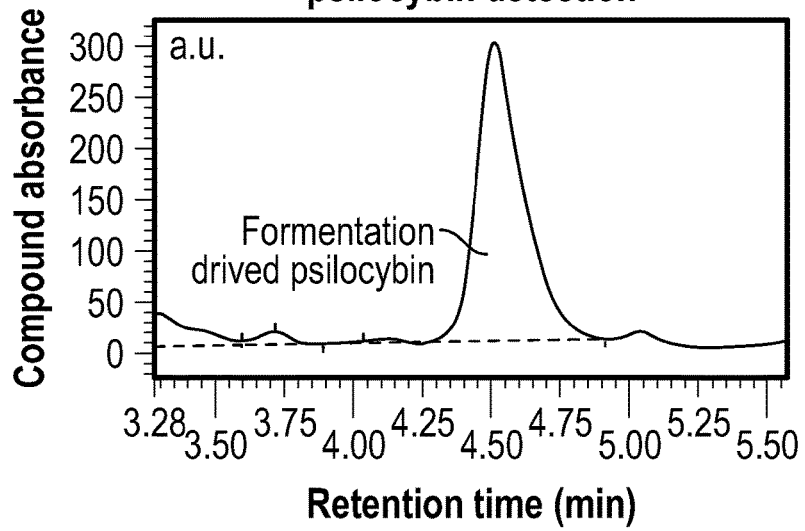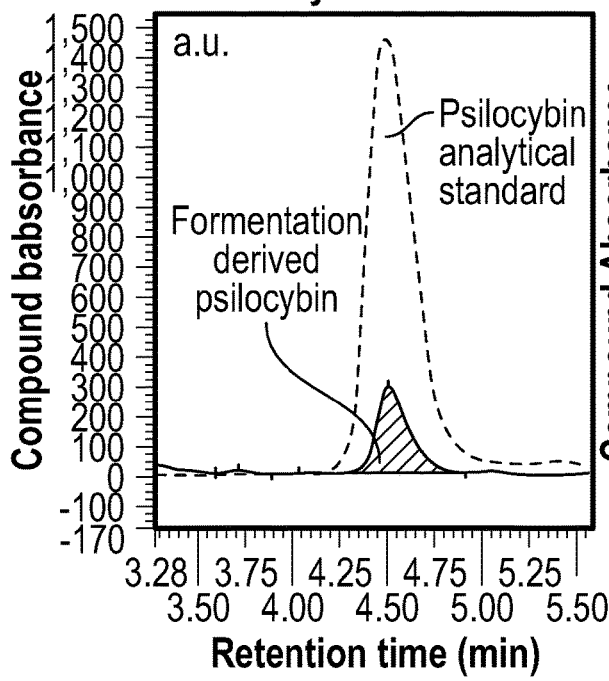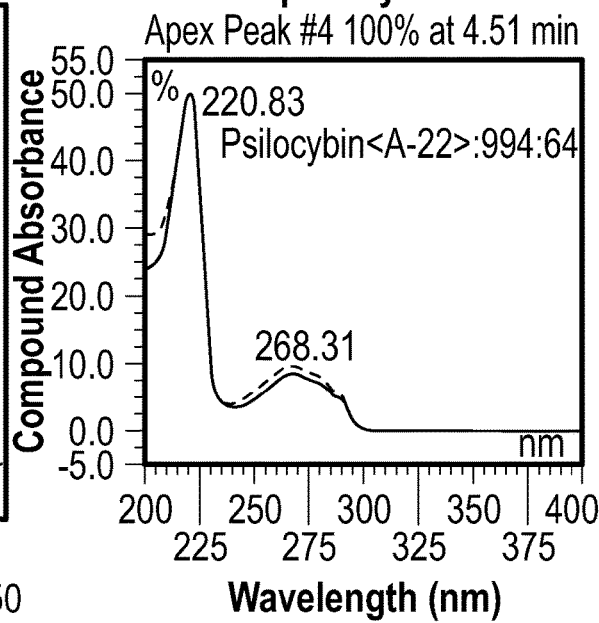
FIG. 11

BIOSYNTHETIC PRODUCTION OF PSILOCYBIN AND RELATED INTERMEDIATES IN RECOMBINANT ORGANISMS

CROSS-REFERENCE TO RELATED APPLICATIONS

This application claims priority from U.S. Provisional Application Ser. No. 62/936,387 filed on Nov. 15, 2019, which is incorporated herein by reference in its entirety.

STATEMENT REGARDING FEDERALLY SPONSORED RESEARCH OR DEVELOPMENT

Not Applicable.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: SEQ_listing_CBTH-06-US.txt, date recorded: Nov. 15, 2020, size: 84 Kbytes). The content of the Sequence Listing file is incorporated herein by reference in its entirety.

FIELD

The present invention generally relates to the production of psilocybin and its intermediates (e.g., tryptamine, 4-hydroxytryptamine, norbaeocystin, baeocystin, and psilocin) in a modified heterologous microorganism.

INTRODUCTION

Mental health problems, which may also be referred to as mental illness or psychiatric disorder, are behavioral or mental patterns which impair the functioning of individuals across the world. Psilocybin has been increasingly evaluated for treating mental health problems. Such mental health disorders include: personality disorders, anxiety disorders, major depressions, and various addictions. In contrast to anxiolytic medicines, usage of psilocybin does not lead to physical dependence.

SUMMARY

The present teachings include a recombinant host organism. The recombinant host organism can include: a plurality of cells transfected by a set of genes for synthesizing psilocybin in the recombinant host organism via at least a first pathway and a second pathway. The recombinant host organism can be a fungal species comprising: *Schizosaccharomyces cerevisiae, Schizosaccharomyces japonicus, Schizosaccharomyces pombe, Schizosaccharomyces cryophilus, Saccharomyces cerevisiae, Kluyveromyces lactis, Kluyveromyces dobzhanskii,* and *Yarrowia lipolytica*. The set of genes can include any combination of a gene selected from a group consisting of PsiD, PsiH, PsiK, and PsiM.

In accordance with a further aspect, PsiD can comprise codon optimized nucleic acid sequences SEQ ID NO: 1, SEQ ID NO: 2, and SEQ ID NO: 3 that encode for isolated amino acid sequences SEQ ID NO: 14, SEQ ID NO: 15, and SEQ ID NO: 16, respectively; PsiH can comprise codon optimized nucleic acid sequences SEQ ID NO: 4, SEQ ID NO: 5, and SEQ ID NO: 6 that encode for isolated amino acid sequences SEQ ID NO: 17 SEQ ID NO: 18, and SEQ ID NO: 19, respectively; PsiK can comprise codon optimized nucleic acid sequences SEQ ID NO: 7 and SEQ ID NO: 8 that encode for isolated amino acid sequences SEQ ID NO: 20 and SEQ ID NO: 21, respectively; and PsiM can comprises codon optimized nucleic acid sequences SEQ ID NO: 9, SEQ ID NO:10, SEQ ID NO:11, SEQ ID NO: 12, and SEQ ID NO: 13 that encode for isolated amino acid sequences SEQ ID NO: 22, SEQ ID NO: 23, SEQ ID NO: 24; SEQ ID NO: 25, and SEQ ID NO: 26, respectively.

In accordance with a further aspect, the set of genes can express amino acid sequences that increase titers of psilocybin in the plurality of cells.

In accordance with a further aspect, the set of genes can synthesize intermediates of psilocybin, wherein the intermediates comprise: tryptamine, 4-hydroxytryptamine, norbaeocystin, baeocystin, and psilocin.

In accordance with a further aspect, a protein can be heterologous to the plurality of cells and an exogenous substrate, wherein the protein is encoded by codon optimized SEQ ID NO: 36.

In accordance with a further aspect, the carbon source can include at least one of: glucose, galactose, sucrose, fructose, corn syrup, corn steep liquor, ethanol, and molasses.

In accordance with another aspect, the first pathway can be a shikimate-chorismate pathway and the second pathway can be a L-tryptophan pathway In accordance with another aspect, the first pathway can be modified by codon optimized SEQ ID NO: 27, SEQ ID NO. 28, SEQ ID NO: 29, SEQ ID NO: 30, and SEQ ID NO: 31 and the second pathway is modified by codon optimized SEQ ID NO: 32, SEQ ID NO: 33, SEQ ID NO: 34, and SEQ ID NO: 35.

The present teaching include a plurality of sequences containing nucleotides or amino acids for producing psilocybin in a recombinant host organism, wherein the plurality of sequences comprise SEQ ID NO: 1-SEQ ID NO: 36.

In accordance with a further aspect, an isolated amino acid sequence comprises SEQ ID NO: 14, SEQ ID NO: 15, and SEQ ID NO: 16, wherein SEQ ID NO: 14, SEQ ID NO: 15, and SEQ ID NO: 16 can be at least 50% similar to each other, and wherein SEQ ID NO: 14 is encoded by codon optimized SEQ ID NO: 1, SEQ ID NO: 15 is encoded by codon optimized SEQ ID NO: 2, and SEQ ID NO: 16 is encoded by codon optimized SEQ ID NO: 3.

In accordance with a further aspect, an isolated amino acid sequence comprises at least one of: SEQ ID NO: 17, SEQ ID NO: 18, and SEQ ID NO: 19, wherein SEQ ID NO: 17, SEQ ID NO: 18, and SEQ ID NO: 19 are at least 40% similar to each other, and wherein SEQ ID NO: 17 is encoded by codon optimized SEQ ID NO: 4, SEQ ID NO: 18 is encoded by codon optimized SEQ ID NO: 5, and SEQ ID NO: 19 is encoded by codon optimized SEQ ID NO: 6.

In accordance with a further aspect, an isolated amino acid sequence comprises at least one of: SEQ ID NO: 20 and SEQ ID NO: 21, wherein SEQ ID NO: 20 and SEQ ID NO: 21 are at least 85% similar to each other; and wherein SEQ ID NO: 21 is encoded by codon optimized SEQ ID NO: 7 and SEQ ID NO: 22 is encoded by codon optimized SEQ ID NO: 8.

In accordance with a further aspect, an isolated amino acid sequence comprises at least one of: SEQ ID NO: 22, SEQ ID NO: 23, SEQ ID NO: 24, SEQ ID NO: 25, and SEQ ID NO: 26, wherein SEQ ID NO: 22, SEQ ID NO: 23, SEQ ID NO: 24, SEQ ID NO: 25, and SEQ ID NO: 26 are at least 55% similar to each other, and wherein SEQ ID NO: 22 is encoded by codon optimized SEQ ID NO: 9, SEQ ID NO:

23 is encoded by codon optimized SEQ ID NO: 10, SEQ ID NO: 24 is encoded by SEQ ID NO: 11, SEQ ID NO: 25 is encoded by SEQ ID NO: 12, and SEQ ID NO: 26 is encoded by SEQ ID NO: 13.

The present teachings include a method. The method can include: transfecting a plurality of cells in a recombinant host organism a set of genes for synthesizing psilocybin via at least a first pathway and a second pathway; and increasing titers of psilocybin in the plurality of cells via the set of genes; and synthesizing intermediates of psilocybin via the set of genes. The recombinant host organism can be a fungal species comprising: Schizosaccharomyces cerevisiae, Schizosaccharomyces japonicus, Schizosaccharomyces pombe, Schizosaccharomyces cryophilus, Saccharomyces cerevisiae, Kluyveromyces lactis, Kluyveromyces dobzhanskii, and Yarrowia lipolytica. The The set of genes can include a gene from a group consisting of: PsiD, PsiH, PsiK, and PsiM.

In accordance with a further aspect, PsiD can comprise codon optimized nucleic acid sequences SEQ ID NO: 1, SEQ ID NO: 2, and SEQ ID NO: 3 that encode for isolated amino acid sequences SEQ ID NO: 14, SEQ ID NO: 15, and SEQ ID NO: 16, respectively; wherein PsiH can comprise codon optimized nucleic acid sequences SEQ ID NO: 4, SEQ ID NO: 5, and SEQ ID NO: 6 that encode for isolated amino acid sequences SEQ ID NO: 17, SEQ ID NO: 18, and SEQ ID NO: 19, respectively; wherein PsiK can comprise codon optimized nucleic acid sequences SEQ ID NO: 7 and SEQ ID NO: 8 that encode for isolated amino acid sequences SEQ ID NO: 20 and SEQ ID NO: 21, respectively; and wherein PsiM can comprise codon optimized nucleic acid sequences SEQ ID NO: 9, SEQ ID NO:10, SEQ ID NO:11, SEQ ID NO: 12, and SEQ ID NO: 13 that encode for isolated amino acid sequences SEQ ID NO: 22, SEQ ID NO: 23, SEQ ID NO: 24; SEQ ID NO: 25, and SEQ ID NO: 26, respectively.

In accordance with a further aspect, the carbon source can include at least one of: glucose, galactose, sucrose, fructose, corn syrup, corn steep liquor, ethanol, and molasses.

In accordance with a further aspect, the method can also include an exogenous substrate and a transporter protein.

In accordance with a further aspect, the first pathway can be a shikimate-chorismate pathway modified by codon optimized SEQ ID NO: 27, SEQ ID NO. 28, SEQ ID NO: 29, SEQ ID NO: 30, and SEQ ID NO: 31 and the second pathway can be a L-tryptophan pathway modified by codon optimized SEQ ID NO: 32, SEQ ID NO: 33, SEQ ID NO: 34, and SEQ ID NO: 35.

In accordance with a further aspect, the transporter protein can be encoded by codon optimized SEQ ID NO: 36.

In accordance with a further aspect, the intermediates can include: tryptamine, 4-hydroxytryptamine, norbaeocystin, baeocystin, and psilocin.

These and other features, aspects, and advantages of the present teachings will become better understood with reference to the following description, examples and appended claims.

DRAWINGS

Those of skill in the art will understand that the drawings, described below, are for illustrative purposes only. The drawings are not intended to limit the scope of the present teachings in any way.

FIG. 1 depicts a table of amino acids and codon triplets.
FIG. 2 depicts a table of genes and enzymes inserted into a recombinant host organism
FIG. 3 depicts the biosynthesis of psilocybin.

FIG. 4 depicts isolated amino acid sequence alignments of recombinant PsiD enzymes SEQ ID NO:14, SEQ ID NO:15, and SEQ ID NO:16.

FIG. 5 depicts isolated amino acid sequence alignments of recombinant PsiH enzymes SEQ ID NO:17, SEQ ID NO:18, and SEQ ID NO:19.

FIG. 6 depicts isolated amino acid sequence alignments of recombinant PsiK enzymes SEQ ID NO:20 and SEQ ID NO:21.

FIG. 7 depicts isolated amino acid sequence alignments of recombinant PsiM enzymes SEQ ID NO:22, SEQ ID NO:23, SEQ ID NO:24, SEQ ID NO:25, and SEQ ID NO:26.

Figure 8:
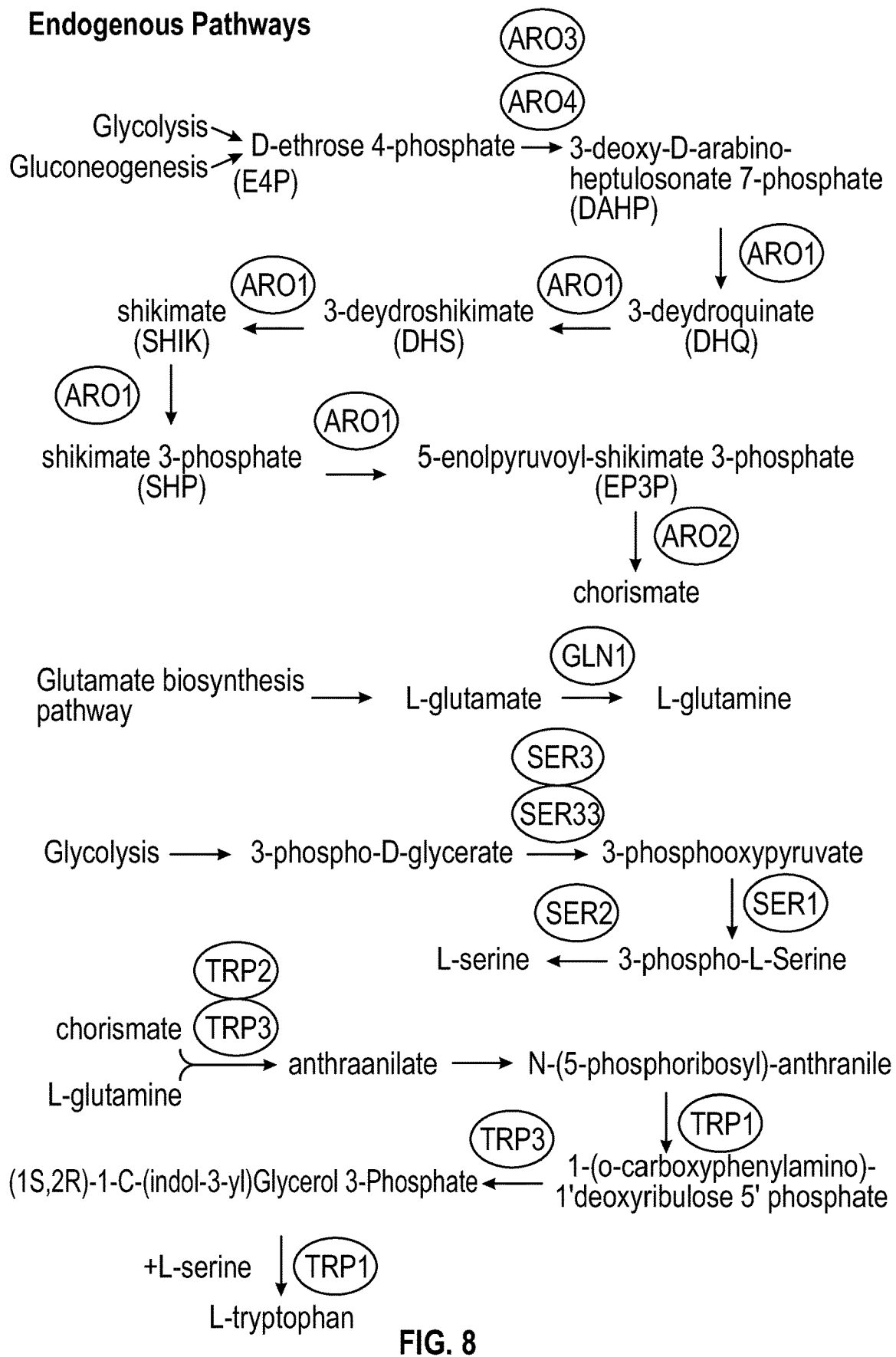
Figure 9:
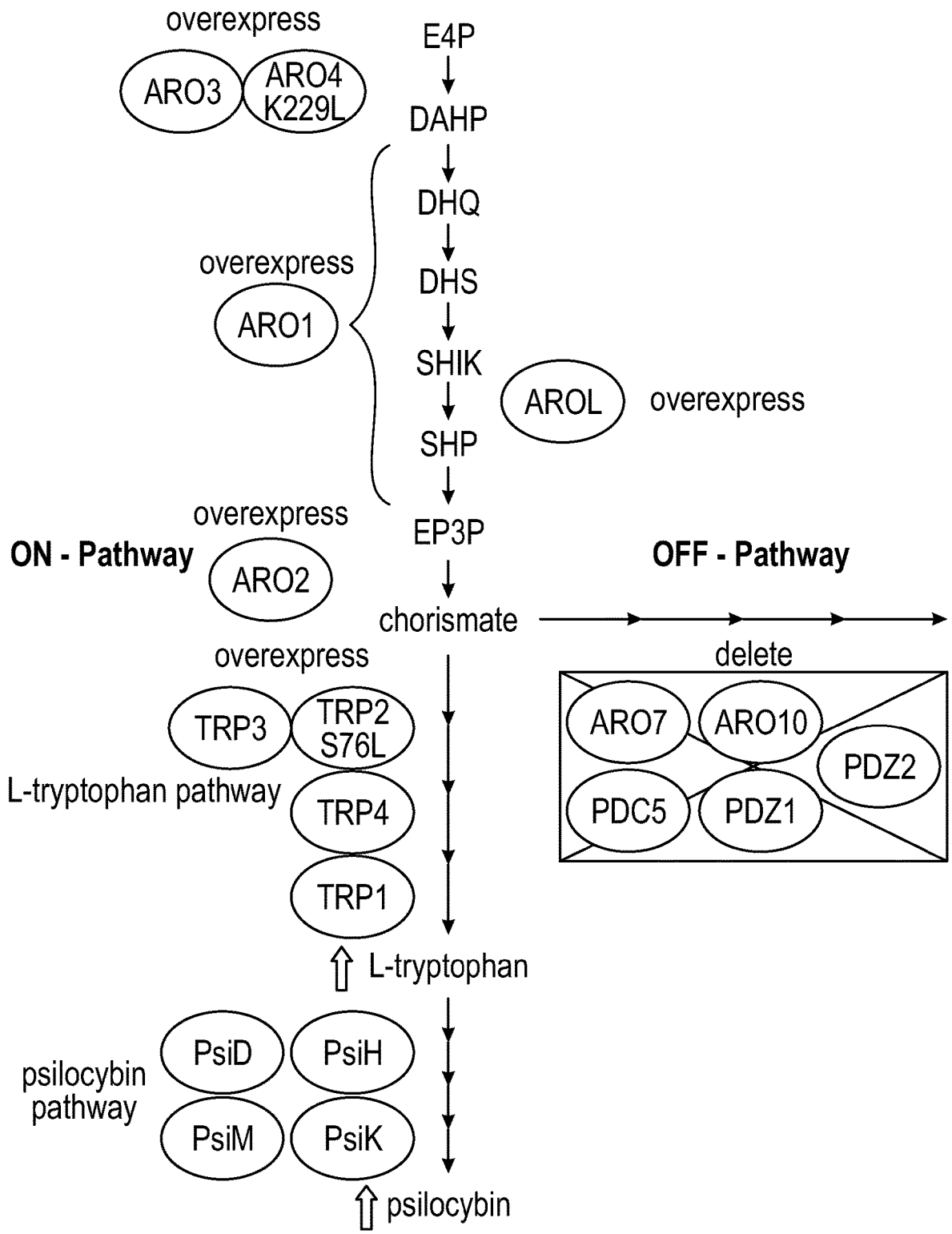
Figure 10:
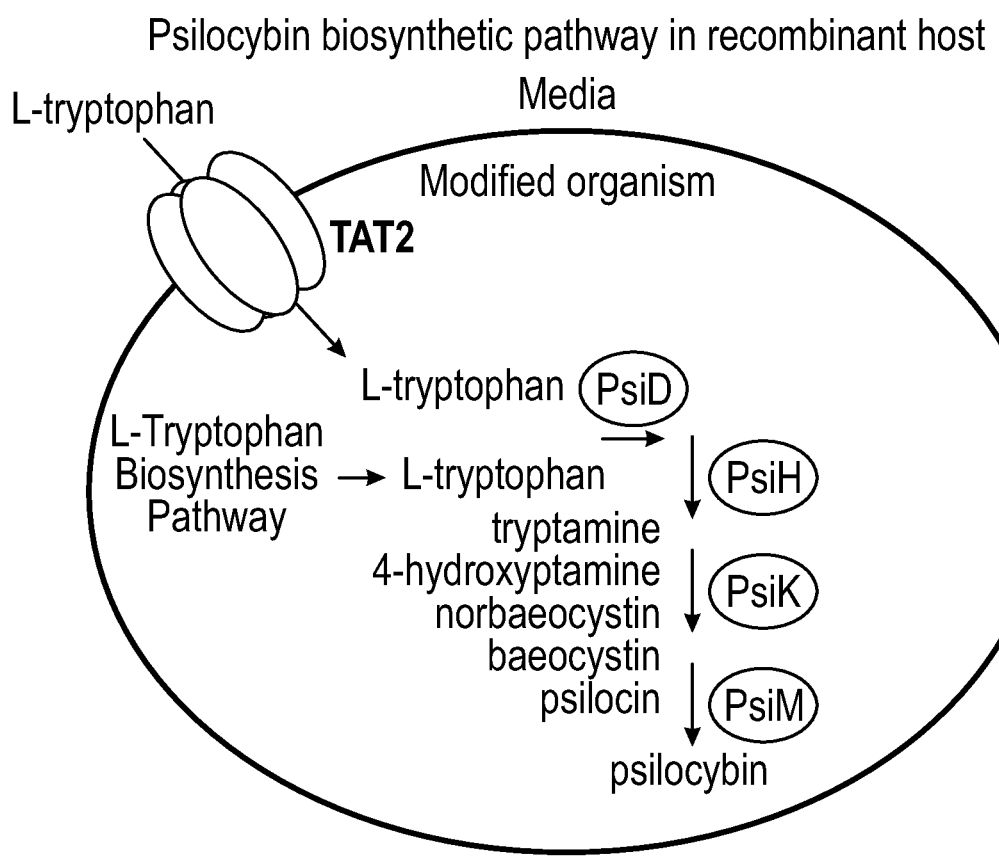

FIG. 8 depicts endogenous pathways in a host organism.
FIG. 9 depicts a scheme to increase metabolic flux through shikimate-chorismate and L-tryptophan pathways.
FIG. 10 depicts a heterologous recombinant host organism.
FIG. 11 depicts HPLC chromatograms and UV/Vis spectra.

DETAILED DESCRIPTION

Abbreviations and Definitions

To facilitate understanding of the invention, a number of terms and abbreviations as used herein are defined below as follows:

Amino acids: As used herein, the term "amino acids" refer to the molecular basis for constructing and assembling proteins, such as enzymes. (See FIG. 1 for a table of amino acids.). Peptide bonds (i.e., polypeptides) are formed between amino acids and assemble three-dimensionally (3-D). The 3-D assembly can influence the properties, function, and conformational dynamics of the protein. Within biological systems, the protein may: (i) catalyze reactions as enzymes; (ii) transport vesicles, molecules, and other entities within cells as transporter entities; (iii) provide structure to cells and organisms as protein filaments; (iv) replicate deoxyribonucleic acid (DNA); and (v) coordinate actions of cells as cell signalers.

Nucleotides: As used herein, the term "nucleotides" refers to the molecular basis for constructing and assembling nucleic acids, such as DNA and ribonucleic acid (RNA). There are two types of nucleotides—purines and pyrimidines. The specific purines are adenine (A) and guanine (G). The specific pyrimidines are cytosine (C), uracil (U), and thymine (T). T is found in DNA, whereas U is found in RNA. The genetic code defines the sequence of nucleotide triplets (i.e., codons) for specifying which amino acids are added during protein synthesis.

Genes: As used herein, the term "genes" refers to regions of DNA. Amino acid sequences in the proteins, as defined by the sequence of a gene, are encoded in the genetic code.

The present invention is directed to biosynthetic production of psilocybin and related intermediates in recombinant organisms. The syntheses of psilocybin and intermediates of psilocybin in a laboratory environment typically involve tedious techniques of organic chemistry. Often reproducibility is elusive and the solvents used during the syntheses of psilocybin and intermediates of psilocybin are environmentally toxic. Decarboxylations, selective methylations, and selective phosphorylations can be difficult to obtain via the techniques of organic chemistry. Further, the yields and purity of the intermediates for obtaining the target molecules can be low using the techniques of organic chemistry, where the starting molecule is L-tryptophan and the target molecule is psilocybin.

The systems and method herein disclose more environmentally benign processes which can have higher throughputs (i.e., more robust processes). The systems and methods herein include: (i) growing modified recombinant host cells and thereby yielding a recombinant host organism; (ii) expressing engineered psilocybin biosynthesis genes and enzymes in the recombinant host organism; (iii) producing or synthesizing psilocybin and/or intermediates of psilocybin in the recombinant host organism; (iv) fermenting the recombinant host organism; and (v) isolating the psilocybin and/or intermediates of psilocybin from the recombinant host organism. Endogenous pathways of the recombinant host can be modified by the systems and methods herein to produce high purity psilocybin and/or intermediates of psilocybin.

Reference is made to the figures to further describe the systems and methods disclosed herein.

Referring to FIG. 2, a table lists the enzymes involved in the direct biosynthesis of psilocybin and psilocybin intermediates in species of fungus (i.e., mushrooms). Gene source organisms provide a genetic starting source (i.e., raw gene sequences) which is codon optimized and engineered to function in the recombinant host organisms. The recombinant host organisms include but are not limited to: *Schizosaccharomyces cerevisiae, Schizosaccharomyces japonicus, Schizosaccharomyces pombe, Schizosaccharomyces cryophilus, Saccharomyces cerevisiae, Kluyveromyces lactis, Kluyveromyces dobzhanskii,* and *Yarrowia lipolytica.*

Further, the genes/enzymes that are inserted or engineered into the recombinant host are PsiD, PsiH, PsiK, and PsiM.

A PsiD enzyme, which is a decarboxylase (e.g., L-tryptophan decarboxylase) derives from a gene source organism herein—*Psilocybe cubensis, Psilocybe cyanescens,* and *Gymnopilus junonius.* The decarboxylase can catalyze the decarboxylation of an aliphatic carboxylic acid (i.e., release carbon dioxide) L-tryptophan to tryptamine and 4-hydroxy-L-tryptophan to 4-hydroxytryptamine, as depicted in FIG. 3.

A PsiH enzyme, which is a monooxygenase (e.g., Tryptamine 4-monooxygenase) derives from a gene source organism herein—*Psilocybe cubensis, Psilocybe cyanescens,* and *Gymnopilus junonius.* The monooxygenase can catalyze the oxidative hydroxylation of the phenyl ring of tryptamine to 4-hydroxytryptamine, as depicted in FIG. 3.

A PsiK enzyme, which is a kinase (e.g., 4-hydroxytryptamine kinase) derives from a gene source organism herein—*Psilocybe cubensis* and *Psilocybe cyanescens.* The kinase can catalyze the phosphorylatation (i.e., adding $O=P(OH)_2$) of the phenolic oxygen of 4-hydroxytryptamine to norbaeocystin, as depicted in FIG. 3. The kinase can also catalyze the phosphorylation of psilocin to psilocybin.

A PsiM enzyme, which is a methyl transferase (e.g., psilocybin synthase) derives from a gene source organism herein—*Psilocybe cubensis, Psilocybe cyanescens, Panaeolus cynascens, Gymnopilus junonius,* and *Gymnopilus dilepis.* The methyl transferase can catalyze the alkylation (i.e., adding a methyl ($CH_3$) group) of the primary amine in norbaeocystin to baecystin, as depicted in FIG. 3. Another alkylation can take place where the methyl transferase when the secondary amine of baecystin becomes a tertiary amine of psilocybin, as depicted in FIG. 3.

As depicted in FIG. 3, the engineered PsiD, PsiH, PsiK, and PsiM enzymes act on substrates in the psilocybin biosynthetic pathway to produce intermediates of psilocybin and psilocybin itself. The initial substrate for psilocybin intermediates and psilocybin can be L-tryptophan and/or 4-hydroxy-L-tryptophan. These initial substrates can be produced endogenously in a recombinant host as described and/or provided exogenously to a fermentation involving a recombinant host, whereby the host uptakes the starting substrates to feed into the psilocybin biosynthetic pathway. The recombinant host herein described that is expressing all, one, or multiple combinations of the engineered PsiD, PsiH, PsiK, PsiM genes can produce tryptamine, 4-hydroxytryptamine, norbaeocystin, baeocystin, psilocybin, and psilocin. Psilocybin may be converted to psilocin due to spontaneous dephosphorylation. Psilocin is in turn an intermediate which can be acted on by the PsiK enzyme to produce psilocybin.

As depicted in FIG. 4, the amino acid alignments of recombinant PsiD enzymes are presented. Recombinant PsiD enzymes have been reengineered from various fungal species to function in heterologous recombinant host organisms herein. The gene used in the pair wise alignment is the PsiD gene from the fungal species—*Psilocybe cubensis, Psilocybe cyanescens,* and *Gymnopilus junonius.* The alignment is performed with EMBOSS Needle Pair wise Sequence Alignment statistic (EBLOSUM62) with *Psilocybe cubensis* (PsiD gene) as a reference. The identity percentage and similarity percentage of the amino acid sequences are presented.

For the PsiD gene, codon optimized nucleic acid sequences SEQ ID NO: 1, SEQ ID NO: 2, and SEQ ID NO: 3 encode for isolated amino acid sequences SEQ ID NO: 14, SEQ ID NO: 15, and SEQ ID NO: 16, respectively. SEQ ID NO: 14 is *Psilocybe cubensis* (PsiD gene); SEQ ID NO: 15 is *Psilocybe cyanescens* (PsiD gene); and SEQ ID NO: 16 is *Gymnopilus junonius* (PsiD gene).

As depicted in FIG. 5, the amino acid alignment of recombinant PsiH enzymes are presented. Recombinant PsiH enzymes have been reengineered from various fungal species to function in heterologous recombinant host organisms herein. The gene used in the pair wise alignment is the PsiH gene from the fungal species—*Psilocybe cubensis, Psilocybe cyanescens,* and *Gymnopilus junonius.* The alignment is performed with EMBOSS Needle Pair wise Sequence Alignment statistic (EBLOSUM62) with *Psilocybe cubensis* (PsiH gene) as a reference. The identity percentage and similarity percentage of the amino acid sequences are presented.

For the PsiH gene, codon optimized nucleic acid sequences SEQ ID NO: 4, SEQ ID NO: 5, and SEQ ID NO: 6 encode for isolated amino acid sequences SEQ ID NO: 17, SEQ ID NO: 18, and SEQ ID NO: 19, respectively. SEQ ID NO: 17 is *Psilocybe cubensis* (PsiH gene); SEQ ID NO: 18 is *Psilocybe cyanescens* (PsiH gene); and SEQ ID NO: 19 is *Gymnopilus junonius* (PsiH gene).

As depicted in FIG. 6, the amino acid alignment of recombinant PsiK enzymes are presented. Recombinant PsiK enzymes have been reengineered from various fungal species to function in heterologous recombinant host organisms herein. The gene used in the pair wise alignment is the PsiK gene from the fungal species—*Psilocybe cubensis* and *Psilocybe cyanescens.* The alignment is performed with EMBOSS Needle Pair wise Sequence Alignment statistic (EBLOSUM62) with *Psilocybe cubensis* (PsiK gene) as a reference. The identity percentage and similarity percentage of the amino acid sequences are presented.

For the PsiK gene, codon optimized nucleic acid sequences SEQ ID NO: 7 and SEQ ID NO: 8 encode for isolated amino acid sequences SEQ ID NO: 20 and SEQ ID NO: 21, respectively. SEQ ID NO: 20 is *Psilocybe cubensis* (PsiK gene) and SEQ ID NO: 21 is *Psilocybe cyanescens* (PsiK gene).

As depicted in FIG. 7, the amino acid alignment of recombinant PsiM enzymes are presented. Recombinant PsiM enzymes have been reengineered from various fungal species to function in heterologous recombinant host organisms herein. The gene used in the pair wise alignment is the PsiM gene from the fungal species—*Psilocybe cubensis, Psilocybe cyanescens, Panaeolus cynascens, Gymnopilus junonius,* and *Gymnopilus dilepis*. The alignment is performed with EMBOSS Needle Pair wise Sequence Alignment statistic (EBLOSUM62) with *Psilocybe cubensis* (PsiM gene) as a reference. The identity percentage and similarity percentage of the amino acid sequences are presented.

For the PsiM gene, codon optimized nucleic acid sequences SEQ ID NO: 9, SEQ ID NO:10, SEQ ID NO:11, SEQ ID NO: 12, and SEQ ID NO: 13 encode for isolated amino acid sequences SEQ ID NO: 22, SEQ ID NO: 23, SEQ ID NO: 24; SEQ ID NO: 25, and SEQ ID NO: 26, respectively. SEQ ID NO: 22 is *Psilocybe cubensis* (PsiM gene); SEQ ID NO: 23 is *Psilocybe cyanescens* (PsiM gene); SEQ ID NO: 24 is *Panaeolus cynascens* (PsiM gene); SEQ ID NO: 25 is *Gymnopilus junonius* (PsiM gene), and SEQ ID NO: 26 is *Gymnopilus dilepis* (PsiM gene).

As depicted in FIG. 8, the endogenous pathways of a recombinant host organism produce precursors for the engineered PsiD, PsiH, PsiK, PsiM genes. Pathways relating to chorismate, L-glutamine, and L-serine, feed into the endogenous pathway for L-tryptophan production, which a recombinant host organism expressing the psilocybin biosynthetic pathway herein described can use to create tryptamine, 4-hydroxytryptamine, norbaeocystin, baeocystin, psilocin, and psilocybin. The enzymes in the endogenous pathways of the recombinant host organism are encircled in FIG. 8. Glycolysis and gluconeogenesis in combination with ARO3, ARO4, ARO1, and ARO2 enzymes can be subjected to the depicted precursors at the specified point in the pathway to selectively yield chrorismate. The glutamate biosynthesis pathway in combination with a GLN1 enzyme can be subjected to the depicted precursor at the specified point in the pathway to selectively yield L-glutamine. Glycolysis in combination with SER3, SER33, SER1, and SER2 enzymes can be subjected to the depicted precursors at the specified points in the pathway to selectively yield L-serine. Chorismate and L-glutamine in combination with TRP1, TRP2, TRP3, and TRP4 enzymes can be subjected to the depicted precursors at the specified point to selectively yield (1S,2R)-1-C-indol-3-yl)glycerol 3-phosphate. The addition of L-serine to (1S,2R)-1-C-indol-3-yl)glycerol 3-phosphate in the presence of the TRP1 enzyme can yield L-tryptophan.

As depicted in FIG. 9, a scheme to increase metabolic flux through the shikimate-chorismate and L-tryptophan pathways is disclosed. The increased metabolic flux through the shikimate-chorismate and L-tryptophan pathways increases the production of L-tryptophan, a key precursor compound for the production of psilocybin and intermediates of psilocybin. Specific enzymes in the described native pathways are overexpressed. Enzymes subject to allosteric inhibition are mutated and overexpressed to render the enzymes insensitive to feedback mechanisms. Enzymes that consume pathway intermediates for off-pathway compound production are hereby deleted.

L-tryptophan production is improved herein by overexpressing a series of enzymes that first increase production of the aromatic compound intermediate, chorismate in a series of enzymatic reactions known as the shikimate pathway. As described in FIG. 5, the shikimate-chorismate pathway initial precursors, PEP and E4P are converted into 3-deoxy-D-arabinoheptulosonate 7-phosphate (DAHP), catalyzed by ARO3 and ARO4 enzymes.

Overexpression of the genes encoding ARO3 enzyme (as encoded by codon optimized SEQ ID NO: 29), and a feedback-resistant mutant ARO4 K229L enzyme (as encoded by codon optimized SEQ ID NO: 30) are described herein and can increase metabolic flux through the pathway. In addition, genes that encode key enzymes, ARO1 enzyme (as encoded by codon optimized SEQ ID NO: 27) and ARO2 (as encoded by codon optimized SEQ ID NO: 28) are overexpressed as part of a series of enzymes that can convert DAHP to chorismate. In addition, the gene that encodes the *Escherichia coli* shikimate kinase II (AROL enzyme) can be overexpressed to increase pathway flux from DHAP to chorismate via codon optimized SEQ ID NO: 31.

Chorismate as a general precursor compound can be converted specifically to L-tryptophan by overexpressing a series of enzymes in the L-tryptophan pathway. As described in FIG. 9, flux through the L-tryptophan pathway can be increased by overexpressing the genes that encode specific enzymes, TRP1 enzyme (as encoded by codon optimized by SEQ ID NO: 32), TRP3 enzyme (as encoded by codon optimized by SEQ ID NO: 34), and TRP4 enzyme (as encoded by codon optimized by SEQ ID NO: 35). Furthermore, overexpression of the gene that encodes the feedback-resistant mutant of TRP2 S76L enzyme (as encoded by SEQ ID NO: 33) is described herein.

Chorismate is a precursor that feeds into the metabolic pathways that produce a variety of aromatic alcohols and aromatic amino acids. The mechanism made operable by systems and methods herein reduce pathway flux into pathways that produce off-pathway targets. As described in FIG. 9, genes that encode native enzymes—PDC5 enzyme and ARO10 enzyme—have been deleted to reduce pathway flux through the pathways that produce aromatic alcohols. The gene that encodes the native enzyme, ARO7 enzyme has been deleted to reduce production of tyrosine and phenylalanine. Genes that encode PDZ1 and PDZ2 enzymes have been deleted to reduce pathway flux through the pABA production pathway.

As depicted in FIG. 10, a modified heterologous recombinant host organism is: (i) expressing endogenous pathways for L-tryptophan; (ii) expressing a recombinant version of the TAT2 L-tryptophan importer protein; and (iii) selectively expressing recombinant psilocybin biosynthetic pathway genes. Such a recombinant host can produce tryptamine, 4-hydroxytryptamine, norbaeocystin, baeocystin, psilocin, and psilocybin from L-tryptophan. L-tryptophan can be created by the host through endogenous pathways (FIG. 8) or engineered pathways (FIG. 9). L-tryptophan may also be fed to the recombinant host organism by media supplementation and up taken by the host expressing the recombinant TAT2 importer protein. Accordingly, contact with the L-tryptophan and the recombinant host organism in the media can selectively direct flux towards psilocybin. Other carbon sources can make contact with the recombinant host organism in the media, wherein the other carbon sources include at least one of: glucose, galactose, sucrose, corn steep liquor, ethanol, fructose, and molasses.

Besides the recombinant TAT2 importer protein, which is encoded by a codon optimized L-tryptophan importer (SEQ ID NO: 36), the nucleotide and amino acid sequences provided are in the order of the psilocybin pathway: PsiD, PsiH, PsiK, and PsiM genes which encode for the respective enzymes. In the systems and methods herein, PsiD enzyme selectively and cleanly catalyzes decarboxylation; the PsiH enzyme catalyzes selective hydroxylation at the 4-position of an indole; the PsiK enzyme catalyzes selective phosphorylation at the hydroxylated 4-position of an indole; and the PsiM enzyme catalyzes selective and stepwise methylations of an amine group, respectively.

By expressing the PsiD gene in the recombinant host organism, codon optimized nucleic acid sequences SEQ ID NO: 1, SEQ ID NO: 2, and SEQ ID NO: 3 encode for isolated amino acid sequences SEQ ID NO: 14, SEQ ID NO: 15, and SEQ ID NO: 16, respectively. Using the techniques of organic chemistry, decarboxylations would require harsh and toxic tin hydrides (e.g., Barton Decarboxylation), as opposed to the selective and clean decarboxylation by the PsiD enzyme in the recombinant host.

By expressing the PsiH gene in the recombinant host organism, codon optimized nucleic acid sequences SEQ ID NO: 4, SEQ ID NO: 5, and SEQ ID NO: 6 encode for isolated amino acid sequences SEQ ID NO: 17, SEQ ID NO: 18, and SEQ ID NO: 19, respectively. Phenyl group functionalization is often done at high temperatures and pressures, while leading to a mixture of products (e.g., hydroxylations at the 5, 6, and 7 positions of the indole). The regioisomers of the hydroxylated products at the 5, 6, and 7 positions of the indole are structurally distinct from each other, but also structurally similar to each other. Separation of such regioisomers can be very challenging and requires cumbersome separation techniques (e.g., slow column chromatography with poor separation (i.e., the regioisomers have similar $R_f$ values to each other) and low accompanying yields). In contrast, the PsiH enzyme catalyzes selective hydroxylation of indole at the 4-position in the recombinant host organism herein at standard room conditions (~25 degrees Celsius at ~1 atm of atmospheric pressure). The systems and methods herein can produce and increase the titers of the hydroxylated indole at the 4-position within the recombinant organism. Using the purification techniques, as described in more detail with respect to the Examples, a sample can be obtained, which exclusively contains the hydroxylated indole at the 4-position. This is indicative of a more facile procedure for obtaining the hydroxylated indole at the 4-position, in comparison to the techniques of organic chemistry.

By expressing the PsiK gene in the recombinant host organism, codon optimized nucleic acid sequences SEQ ID NO: 7 and SEQ ID NO: 8 encode for isolated amino acid sequences SEQ ID NO: 20 and SEQ ID NO: 21, respectively. Primary amines and indole nitrogen are nucleophilic groups than can compete with phenolic oxygen for phosphorylation. In contrast, the recombinant host supports the PsiK enzyme catalysis of selective phosphorylation of the phenolic oxygen. The recombinant host and the PsiK enzyme can also catalyze the undoing of de-phosphorylations that yield psilocin. Stated another way, the recombinant host organism and the expressed PsiK gene for encoding the PsiK enzyme can convert psilocin back to the target molecule psilocybin. Stated yet another way, the recombinant host organism and the expressed PsiK gene for encoding the PsiK enzyme can provide a corrective mechanism to obtain the target molecule psilocybin.

By expressing the PsiM gene in the recombinant host organism, codon optimized nucleic acid sequences SEQ ID NO: 9, SEQ ID NO:10, SEQ ID NO:11, SEQ ID NO: 12, and SEQ ID NO: 13 encode for isolated amino acid sequences SEQ ID NO: 22, SEQ ID NO: 23, SEQ ID NO: 24, SEQ ID NO: 25, and SEQ ID NO: 26, respectively. The primary amine when subjected to methyl iodide may get over alkylated to the quaternary amine. Further, the reaction is not selective as monoalklyated and dialkylated products may also be obtained. To further complicate the alkylation, the nitrogen of the indole is sufficiently nucleophilic to perform alkylations. In contrast, the PsiM enzyme catalyzes selective methylation at the primary amine in the recombinant host organism, which is also stepwise. The first methylation yields norbaeocystin and the second methylation yields psilocybin. The indole nitrogen does not get methylated.

SEQ ID NO: 1-SEQ ID NO: 36 of the systems and methods herein aid in increasing titers of psilocybin in the recombinant host organism in comparison to the titers of psilocybin in natural state of the host organism. As described above, the mutations at specific points of the pathways above direct flux toward yielding psilocybin in the recombinant host organism.

EXAMPLES

Aspects of the present teachings may be further understood in light of the following examples, which should not be construed as limiting the scope of the present teachings in any way.

The following examples are provided to illustrate various aspects of the present invention. They are not intended to limit the invention, which is defined by the accompanying claims.

In the examples below, genetically engineered host cells may be any species of yeast herein, including but not limited to any species of *Saccharomyces, Candida, Schizosaccharomyces, Yarrowia*, etc., which have been genetically altered to produce precursor molecules, intermediate molecules, and psilocybin molecules. Additionally, genetically engineered host cells may be any species of filamentous fungus, including but not limited to any species of *Aspergillus*, which have been genetically altered to produce precursor molecules, intermediate molecules, and psilocybin molecules. Some of the species of yeast herein for the recombinant host organism include but are not limited to: *Schizosaccharomyces cerevisiae, Schizosaccharomyces japonicus, Schizosaccharomyces pombe, Schizosaccharomyces cryophilus, Saccharomyces cerevisiae, Kluyveromyces lactis, Kluyveromyces dobzhanskii,* and *Yarrowia lipolytica*.

The gene sequences from gene source organisms are codon optimized to improve expression using techniques disclosed in U.S. patent application Ser. No. 15/719430, filed Sep. 28, 2017, entitled "An Isolated Codon Optimized Nucleic Acid". The gene source organisms can include, but are not limited to: *Psilocybe cubensis, Psilocybe cyanescens, Panaeolus cynascens, Gymnopilus junonius,* and *Gymnopilus dilepis*. DNA sequences are synthesized and cloned using techniques known in the art. Gene expression can be controlled by inducible or constitutive promoter systems using the appropriate expression vectors. Genes are transformed into an organism using standard yeast or fungus transformation methods to generate modified host strains (i.e., the recombinant host organism). The modified strains express genes for: (i) producing L-tryptophan and precursor molecules to L-tryptophan; (ii) increasing an output of L-tryptophan molecules and precursor molecules to L-tryptophan molecules; (iii) increasing the import of exogenous L-tryptophan into the host strain; and (iv) the genes for the psilocybin biosynthetic pathway. In the presence or absence of exogenous L-tryptophan, fermentations are run to determine if the cell will convert the L-tryptophan into psilocybin. The L-tryptophan and psilocybin pathway genes herein can be integrated into the genome of the cell or maintained as an episomal plasmid. Samples are: (i) prepared and extracted using a combination of fermentation, dissolution, and purification steps; and (ii) analyzed by HPLC for the presence of precursor molecules, intermediate molecules, and psilocybin molecules.

Using the systems and methods herein, the genes which can be expressed to encode for a corresponding enzyme or other type of proteins include but are not limited to: PsiM, PsiH, PsiD, PsiK, TRP1, TRP2 S76L, TRP3, TRP4, ARO1, ARO2, ARO3, ARO4 K229L, and AROL. For example, the PsiM gene is expressed or (overexpressed) to encode for the PsiM enzyme; the PsiH gene is overexpressed to encode for the PsiH enzyme; and so forth. These PsiM, PsiH, PsiD, and PsiK genes can derive from: *Psilocybe cubensis, Psilocybe cyanescens, Panaeolus cynascens, Gymnopilus junonius,* and *Gymnopilus dilepis*. These TRP1, TRP2 S76L, TRP3, TRP4, ARO1, ARO2, ARO3, and ARO4 K229L genes can derive from *Saccharomyces cerevisiae*. These AROL genes can derive from *Escherichia coli*. Further, these genes are transformed into *Schizosaccharomyces cerevisiae, Schizosaccharomyces japonicus, Schizosaccharomyces pombe, Schizosaccharomyces cryophilus, Saccharomyces cerevisiae, Kluyveromyces lactis, Kluyveromyces dobzhanskii,* and *Yarrowia lipolytica*. The PsiM, PsiH, PsiD, PsiK, TRP1, TRP2 S76L, TRP3, TRP4, ARO1, ARO2, ARO3, ARO4 K229L, and AROL genes which derive from at least one of: *Psilocybe cubensis, Psilocybe cyanescens, Panaeolus cynascens, Gymnopilus junonius, Gymnopilus dilepis, Saccharomyces cerevisiae,* and *Escherichia coli* can be expressed at the same time. Gene sequences can be determined using the techniques disclosed in U.S. Nonprovisional patent application Ser. No. 16/558,909 filed on Sep. 3, 2019, entitled "Automated Pipeline".

Example 1—Construction of *Saccharomyces cerevisiae* Platform Strains with Elevated Metabolic Flux Towards L-tryptophan via Overexpression of the Feedback Resistant Mutant, ARO4 K229L The optimized ARO4 K229L gene is synthesized using DNA synthesis techniques known in the art. The optimized gene can be cloned into vectors with the proper regulatory elements for gene expression (e.g. promoter, terminator) and the derived plasmid can be confirmed by DNA sequencing. As an alternative to expression from an episomal plasmid, the optimized ARO4 K229L gene is inserted into the recombinant host genome. Integration is achieved by a single cross-over insertion event of the plasmid. Strains with the integrated gene can be screened by rescue of auxotrophy and genome sequencing.

Example 2—Construction of *Saccharomyces cerevisiae* Platform Strains with Elevated Metabolic Flux Towards L-tryptophan via Deletion of PDC5

Deletion of PDC5 is performed by replacement of the PDC5 gene with the URA3 cassette in the recombinant host. The PDC5 URA3 knockout fragment, carrying the marker cassette, URA3, and homologous sequence to the targeted gene, PDC5, can be generated by bipartite PCR amplification. The PCR product is transformed into a recombinant host and transformants can be selected on synthetic URA drop-out media. Further verification of the modification in said strain can be carried out by genome sequencing, and analyzed by the techniques disclosed in U.S. Nonprovisional patent application Ser. No. 16/558,909 filed on Sep. 3, 2019, entitled "Automated Pipeline".

Example 3—Method of Growth

Modified host cells that yield recombinant host cells, such as the psilocybin-producing strain herein, express engineered psilocybin biosynthesis genes and enzymes. More specifically, the psilocybin-producing strain herein is grown in rich culture media containing yeast extract, peptone and a carbon source of glucose, galactose, sucrose, fructose, corn syrup, corn steep liquor, ethanol, and/or molasses. The recombinant host cells are grown in either shake flasks or fed-batch bioreactors. Fermentation temperatures can range from 25 degrees Celsius to 37 degrees Celsius at a pH range from pH 4 to pH 7.5. Exogenous L-tryptophan can be added to media to supplement the precursor pool for psilocybin production, which can be up taken by strains expressing the TAT2 L-tryptophan importer protein. The strains herein can be harvested during a fermentation period ranging from 12 hours onward from the start of fermentation.

Example 4—Detection of Isolated Product

To identify fermentation derived psilocybin produced by a recombinant host expressing the engineered psilocybin biosynthetic pathway, an Agilent 1100 series liquid chromatography (LC) system equipped with a HILIC column (Obelisc N, SIELC, Wheeling, Ill. USA) is used. A gradient is used of mobile phase A (ultraviolet (UV) grade $H_2O$+ 0.1% Formic Acid) and mobile phase B (UV grade acetonitrile+0.1% Formic Acid). Column temperature is set at 40 degree Celsius. Compound absorbance is measured at 220 nanometers (nm) and 270 nm wavelength using a diode array detector (DAD) and spectral analysis from 200 nm to 400 nm wavelengths. A 0.1 milligram (mg)/milliliter (mL) analytical standard is made from psilocybin certified reference material (Cayman Chemical Company, USA). Each sample is prepared by diluting fermentation biomass from a recombinant host expressing the engineered psilocybin biosynthesis pathway 1:1 in 100% ethanol and filtered in 0.2 um nanofilter vials. Samples are compared to the psilocybin analytical standard retention time and UV-visible spectra for identification. As depicted in inset A of FIG. 11, a fermentation derived product is obtained which has absorption of 300 au at 220 nm with a retention time of 4.55 minutes in a HPLC chromatogram. As depicted in inset B of FIG. 11, the fermentation derived product obtained matches the retention time of the psilocybin analytical standard in the overlaid HPLC chromatograms. This indicates that the fermentation derived product is psilocybin. As depicted in inset C of FIG. 11, the UV-visible spectra of the fermentation derived product and the psilocybin analytical standard are identical. This further corroborates that the fermentation derived product is psilocybin.

OTHER EMBODIMENTS

The detailed description set-forth above is provided to aid those skilled in the art in practicing the present invention. However, the invention described and claimed herein is not to be limited in scope by the specific embodiments herein disclosed because these embodiments are intended as illustration of several aspects of the invention. Any equivalent embodiments are intended to be within the scope of this invention. Indeed, various modifications of the invention in addition to those shown and described herein will become apparent to those skilled in the art from the foregoing description which does not depart from the spirit or scope of the present inventive discovery. Such modifications are also intended to fall within the scope of the appended claims.

REFERENCES CITED

All publications, patents, patent applications and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present invention.

SEQUENCE LISTINGS
(*Psilocybe cubensis* (PSID gene))
SEQ ID NO: 1
ATGCAAGTCATCCCCGCGTGCAACAGCGCAGCTATAAGGTCACTTTGTCCGACCC

CCGAGAGCTTTAGAAATATGGGCTGGCTTTCCGTGAGCGATGCCGTCTATAGCGA

ATTTATAGGTGAACTTGCGACGAGAGCATCTAATAGAAACTACAGCAATGAGTT

CGGTTTAATGCAACCAATACAAGAATTTAAAGCGTTCATCGAGAGTGATCCCGTT

GTACACCAAGAGTTTATCGACATGTTTGAAGGCATCCAAGATTCTCCGAGGAACT

ACCAAGAACTATGTAACATGTTCAATGATATTTTTAGGAAGGCTCCCGTATACGG

AGATTTGGGCCCTCCGGTCTACATGATTATGGCGAAGTTGATGAATACAAGGGCG

GGTTTCAGTGCGTTCACAAGACAACGTCTGAACCTGCATTTTAAAAAGCTGTTCG

ATACCTGGGGTTTATTTCTTTCATCCAAAGACAGCAGGAATGTCCTGGTAGCTGA

CCAGTTTGATGATAGGCACTGCGGCTGGCTGAACGAGAGGGCATTATCTGCGAT

GGTGAAACACTATAATGGGCGTGCATTTGATGAAGTATTTCTATGTGACAAAAAT

GCACCCTATTACGGCTTTAATTCATACGACGATTTCTTCAATAGGAGGTTCCGTA

ATAGAGACATTGATAGACCCGTTGTCGGCGGCGTGAACAACACGACGCTTATAT

CAGCAGCCTGTGAGTCTCTGTCTTATAACGTCAGCTATGACGTGCAATCCTTAGA

TACTTTAGTTTTCAAAGGTGAGACGTACTCATTAAAACATCTTTTGAATAATGAT

CCATTTACGCCACAATTCGAGCACGGTTCCATATTGCAAGGATTCCTAAACGTGA

CAGCATATCATCGTTGGCACGCGCCGGTTAACGGAACTATCGTCAAGATAATCAA

CGTTCCTGGTACTTATTTCGCACAAGCGCCGTCTACCATCGGTGATCCGATCCCA

GATAATGACTATGATCCACCGCCATATCTAAAGAGTCTTGTGTACTTCAGTAACA

TTGCAGCGAGACAGATTATGTTCATAGAAGCTGATAACAAGGAGATAGGCCTAA

TTTTCCTGGTTTTTATAGGCATGACAGAAATTTCAACGTGTGAAGCAACGGTATC

CGAGGGGCAACATGTCAATAGAGGGGACGACCTGGGTATGTTTCATTTCGGGGG

CTCTTCTTTTGCCCTTGGCCTGCGTAAAGACTGCCGTGCCGAAATTGTTGAGAAG

TTCACGGAGCCCGGGACAGTTATAAGGATTAACGAAGTCGTCGCCGCCTTGAAG

GCTTAA (*Psilocybe cyanescens* (PSID gene))
SEQ ID NO: 2
ATGCAAGTGCTTCCTGCTTGCCAAAGCTCTGCCCTTAAAACCCTGTGTCCGAGCC

CCGAGGCTTTTAGAAAGCTGGGATGGCTACCTACGTCTGACGAAGTGTACAACG

AGTTCATAGATGATCTGACTGGCAGGACTTGCAATGAGAAGTATAGCAGCCAAG

TAACCCTGTTAAAGCCAATCCAAGACTTCAAGACTTTCATAGAGAATGACCCGAT

AGTATATCAAGAGTTCATTAGCATGTTTGAGGGCATAGAACAGAGCCCTACTAAC

TATCATGAGCTATGTAACATGTTCAACGATATTTTTCGTAAGGCACCCCTATACG

GAGACTTAGGACCACCTGTCTACATGATAATGGCACGTATTATGAATACGCAGGC

GGGTTTTTCAGCGTTCACCAAAGAATCTCTGAACTTCCATTTTAAGAAGCTATTC

GACACGTGGGGTCTATTCCTAAGCTCTAAAAATTCCAGAAACGTACTTGTCGCCG

ATCAGTTTGACGACAAACATTACGGATGGTTTTCTGAGAGAGCAAAGACTGCGA

TGATGATCAACTATCCAGGACGTACATTCGAGAAGGTCTTCATCTGTGACGAGCA

TGTGCCTTATCACGGATTTACTTCCTATGACGACTTCTTTAACAGGAGATTTCGTG

ACAAGGATACAGACCGTCCCGTCGTCGGTGGCGTCACCGACACGACGTTGATAG

-continued

GCGCGGCATGTGAAAGTTTATCTTATAACGTTTCTCACAACGTCCAATCACTGGA

CACCCTTGTCATAAAAGGCGAGGCGTACTCTTTAAAACACCTTCTGCATAATGAC

CCATTTACGCCACAGTTTGAACATGGATCTATCATCCAAGGATTCTTGAACGTTA

CAGCCTATCACAGATGGCACTCTCCAGTTAACGGCACTATTGTGAAGATTGTAAA

CGTACCAGGGACATACTTTGCCCAGGCGCCCTATACCATAGGTAGCCCAATCCCT

GATAATGACCGGGACCCGCCGCCCTACTTGAAGAGCCTTGTTTATTTTAGCAACA

TTGCTGCCAGACAGATTATGTTTATTGAGGCTGACAATAAAGATATTGGCCTTAT

CTTTCTTGTGTTCATTGGCATGACTGAAATTAGCACATGTGAAGCGACGGTATGC

GAAGGACAGCACGTTAACAGAGGCGATGACCTTGGGATGTTTCATTTTGGGGGA

TCGAGTTTTGCATTGGGGCTTAGAAAAGATAGCAAAGCAAAAATACTAGAAAAA

TTTGCAAAGCCGGGAACAGTAATAAGGATTAACGAGCTGGTGGCATCCGTCAGA

AAATAA (*Gymnopilus junonius* (PSID gene))

SEQ ID NO: 3

ATGTCATCTCCTCGTATCGTGCTGCACAGGGTTGGTGGCTGGCTGCCTAAAGACC

AAAACGTGCTAGAAGCATGGCTGAGCAAGAAGATTGCTAAAGCAAAAACTAGA

AATAGGGCTCCAAAAGATTGGGCTCCTGTGATTCAAGACTTCCAGAGACTGATA

GAGACCGATGCCGAGATCTACATGGGTTTCCATCAGATGTTCGAGCAGGTCCCCA

AGAAAACTCCGTACGATAAAGACCCCACCAATGAGCAATGGCAAGTAAGAAATT

ATATGCACATGTTAGATCTGTTCGACCTAATTATAACCGAGGCACCGGATTTCGA

ACAAAATGATCTTGTTGGATTTCCAATAAATGCAATCCTGGATTGGCCCATGGGG

ACCCCCGGTGGGCTTACTGCATTTATTAACCCTAAAGTAAATATTATGTTTCATA

AAATGTTTGACGTTTGGGCAGTATTTCTGTCATCTCCAGCATCATGCTACGTCCTA

AATACAAGCGATAGCGGTTGGTTCGGTCCCGCTGCAACCGCAGCTATACCCAACT

TCAAAGAGACCTTCATCTGCGACCCAAGTCTGCCATACCTAGGGTACACTAGCTG

GGATAATTTCTTCACCAGGCTGTTTAGGCCGGGGGTGCGTCCTGTCGAGTTCCCG

AACAATGATGCCATTGTTAACAGTGCGTGTGAATCCACGGTTTATAATATAGCTC

CAAACATTAAACCACTAGATAAATTTTGGATTAAGGGAGAGCCGTATTCCCTAAA

TCACATACTTAATAACGACCCGTACGCGAGCCAGTTCGTAGGTGGAACCATATCC

CAAGCATTCTTATCTGCGCTGAACTATCACCGTTGGGCGAGTCCGGTTAACGGCA

ACATTGTCAAGGTCGTCAATGTTCCGGGTACATACTACGCGGAGTCCCCAGTTAC

CGGTTTTGGGAATCCAGAAGGGCCAGATCCAGCGGCGCCCAATCTATCTCAAGG

TTTCATTACTGCTGTGGCTGCGAGAGCCCTGATTTTCATAGAGGCCGATAACCCT

AACATCGGATTAATGTGTTTTGTGGGGGTTGGCATGGCAGAGGTCTCAACATGTG

AAGTTACCGTGAGTGTAGGCGATGTTGTCAAGAAAGGAGATGAGATTGGAATGT

TCCATTTCGGGGGAAGCACTCACTGCTTGATATTTAGGCCACAAACAAAAATTAC

GTTCAATCCCGACTATCCTGTGTCAACCGCCGTACCCTTGAATGCTGCAGTGGCA

ACCGTCGTATAA (*Psilocybe cubensis* (PSIH gene))

SEQ ID NO: 4

ATGATTGCCGTCTTATTCTCTTTTGTCATAGCTGGCTGCATCTATTATATAGTATC

CCGTCGTGTGCGTCGTTCAAGACTTCCGCCCGGACCACCAGGCATCCCTATCCCC

TTTATCGGCAATATGTTTGACATGCCCGAAGAATCACCCTGGTTGACGTTTCTGC

```
AATGGGGCAGAGATTATAATACAGACATTTTGTATGTAGATGCAGGCGGAACTG

AGATGGTAATATTGAATACCCTTGAGACAATCACTGATTTGTTAGAAAAGAGGG

GGTCTATATATTCTGGCAGGCTAGAAAGTACCATGGTTAATGAGTTGATGGGGTG

GGAGTTTGATCTAGGATTCATCACCTACGGTGATCGTTGGAGAGAGGAGAGAAG

GATGTTCGCGAAAGAGTTCAGCGAAAAGGGAATCAAACAATTCAGGCACGCCCA

AGTAAAGGCGGCGCATCAACTTGTCCAACAGCTGACAAAAACACCGGATCGTTG

GGCTCAACACATACGTCATCAGATAGCCGCCATGTCTTTAGACATCGGCTATGGC

ATAGACTTAGCGGAGGATGATCCATGGTTAGAAGCAACACACTTAGCTAACGAA

GGACTGGCGATAGCTTCCGTCCCAGGAAAATTTTGGGTAGACTCATTTCCGTCTC

TGAAATACCTACCAGCCTGGTTTCCTGGAGCTGTCTTCAAACGTAAGGCAAAAGT

ATGGAGGGAGGCAGCAGACCATATGGTGGACATGCCATATGAGACTATGAGGAA

ATTGGCGCCACAGGGCTTGACTAGACCATCCTATGCATCTGCAAGACTACAGGCC

ATGGACCTAAACGGTGATTTGGAGCACCAAGAGCACGTAATTAAAAACACAGCA

GCCGAAGTGAACGTCGGAGGGGAGATACAACCGTCTCTGCGATGAGTGCGTTC

ATACTAGCGATGGTCAAGTATCCGGAAGTACAGCGTAAAGTCCAGGCCGAGCTA

GACGCACTTACTAACAACGGCCAGATTCCCGATTACGACGAGGAAGACGATAGT

CTACCTTACTTGACCGCATGTATTAAAGAGTTATTTAGATGGAATCAAATTGCGC

CCCTAGCGATTCCTCACAAGTTAATGAAAGACGATGTATATAGGGGTTATCTAAT

ACCTAAGAATACGCTAGTTTTTGCAAACACATGGGCGGTCCTGAACGACCCTGAA

GTCTACCCAGACCCTAGCGTATTTAGGCCGGAGCGTTATTTAGGACCCGACGGTA

AGCCCGATAATACTGTCAGGGACCCCAGGAAGGCTGCGTTCGGGTATGGGAGGA

GGAACTGTCCAGGAATACACTTAGCCCAATCAACCGTCTGGATAGCCGGAGCGA

CCTTACTTAGTGCGTTTAATATCGAGAGGCCAGTTGACCAGAATGGGAAACCCAT

CGATATTCCAGCAGACTTCACAACCGGGTTTTTCAGGCATCCTGTTCCTTTTCAGT

GCCGTTTCGTGCCTAGGACTGAACAGGTCTCCCAATCAGTCAGTGGGCCGTAA (Psilocybe cyanescens (PSIH gene))
                                           SEQ ID NO: 5
ATGGCGCCTTTGACAACCATGATTCCGATCGTTCTATCTCTTCTAATAGCGGGGT

GTATATATTATATCAACGCAAGGAGAATTAAAAGGTCCAGGTTGCCACCAGGAC

CGCCGGGTATTCCTATTCCATTCATCGGGAACATGTTCGACATGCCAAGCGAAAG

TCCCTGGCTAATCTTCCTACAATGGGACAAGAGTACCAGACCGATATAATTTAC

GTTGACGCGGGAGGAACTGATATGATAATACTTAATTCCCTAGAGGCAATTACA

GATCTGTTAGAGAAAAGGGGCTCATTGTATAGCGGGAGGTTGGAATCCACGATG

GTAAACGAGCTAATGGGTTGGGAGTTTGATTTCGGTTTCATACCTTACGGTGAAA

GATGGAGGGAAGAACGTCGTATGTTCGCCAAAGAGTTTTCTGAGAAGAACATAA

GGCAGTTTAGACACGCCCAAGTAAAGGCTGCCAATCAGCTAGTGCGTCAACTAA

CCGATAAACCGGACAGGTGGTCACACCACATAAGGCATCAAATCGCGTCCATGG

CCCTGGACATCGGTTACGGAATCGATCTTGCTGAAGACGATCCGTGGATCGCAGC

TTCCGAACTGGCGAATGAAGGCTTGGCTGTAGCCTCAGTGCCAGGATCTTTTTGG

GTAGATACGTTCCCGTTTCTTAAATATTTGCCAAGTTGGTTACCTGGCGCGGAGTT

CAAAAGAAACGCAAAGATGTGGAAGGAAGGAGCAGATCATATGGTCAATATGC
```

-continued
CTTACGAAACGATGAAAAAGCTAAGCGCACAAGGACTGACTAGACCATCATATG

CAAGTGCGAGGCTACAGGCTATGGACCCGAACGGGGATCTTGAACATCAAGAAA

GAGTGATCAAAAATACGGCCACGCAGGTAAATGTTGGTGGTGGGGATACTACAG

TCGGGGCAGTAAGTGCGTTTATCCTTGCGATGGTAAAATACCCGGAAGTTCAAAG

GAAAGTACAAGCCGAGCTGGACGAGTTCACGAGCAAGGGGAGGATACCGGATT

ACGATGAAGATAACGATTCTCTTCCCTATCTATCGGCTTGCTTCAAAGAGCTGTT

CAGGTGGGGCCAGATTGCGCCTTTGGCGATTGCTCATAGGCTGATAAAGGACGA

TGTCTATAGGGAATATACTATCCCAAAGAATGCTCTGGTCTTTGCGAACAATTGG

TATGGGCGTACTGTATTGAATGACCCTTCTGAGTATCCCAATCCTTCAGAATTTA

GACCTGAAAGGTACTTGGGGCCCGATGGTAAGCCAGATGACACCGTCAGGGACC

CAAGAAAGGCAGCGTTTGGGTACGGACGTAGAGTGTGTCCAGGGATACACCTGG

CGCAGAGCACGGTCTGGATTGCTGGTGTCGCGTTGGTATCTGCCTTCAACATTGA

GCTGCCCGTGGACAAAGACGGGAAATGTATAGATATTCCGGCGGCCTTCACGAC

GGGATTCTTTAGATAA (*Gymnopilus junonius* (PSIH gene))
SEQ ID NO: 6
ATGATGTCCGAGATGAATGGGATGGATAAATTGGCGCTATTGACGACGTTATTAG

CTGCCGGTTTTCTATACTTCAAGAATAAGCGTCGTTCCGCGTTGCCGTTCCCGCCA

GGGCCGAAAAAGCATCCCCTTTTAGGTAACTTGCTGGACCTTCCGAAGAAGCTGG

AGTGGGAGACGTACAGAAGATGGGGAAAAGAATACAATTCAGATGTAATACATG

TTAGCGCGGGGAGTGTAAACTTAATTATCGTTAATTCCTTTGAAGCTGCGACAGA

CCTGTTTGATAAGAGATCAGCCAATTATTCAAGTAGGCCACAATTCACGATGGTG

AGAGAACTGATGGGATGGAATTGGTTGATGTCTGCATTAATATACGGTGACAAG

TGGAGAGAGCAACGTAGGTTGTTTCAGAAACATTTCAGTACAACGAATGCCGAA

CTTTACCAAAATACACAATTAGAATATGTTCGTAAAGCCCTGCAGCATCTGCTAG

AAGAGCCTTCAGATTTTATGGGAATAACACGTCACATGGCTGGGGCGTCAGCA

TGTCCCTGGCATATGGCTTAAACATTCAGAAGAAAAACGACCCTTTTGTTGACCT

TGCACAAAGGGCAGTGCACAGCATAACAGAGGCCTCAGTTCCTGGGACATTTTG

GGTAGACGTAATGCCTTGGCTAAAGTATATTCCAGAATGGGTGCCGGGTGCTGGC

TTTCAGAAGAAGGCTAGAGTGTGGAGGAAATTACAGCAAGATTTTCGTCAGGTC

CCATATCAGGCAGCTCTGAAAGACATGGCTTCAGGGAAAGCTAAACCATCATTT

GCAAGTGAGTGTTTGGAGACGATAGACGACAATGAGGATGCACAAAGGCAAAG

GGAGGTGATAAAAGACACAGCTGCCATTGTATTCGCAGCCGGTGCGGATACAAG

CCTTAGTGGAATCCATACATTATTCGCCGCAATGTTGTGTTACCCAGAGGTCCAG

AAGAAAGCACAAGAAGAACTGGATCGTGTCTTGGGTGGGAGACGTCTACCGGAA

TTTACCGATGAGCCCAACATGCCCTACATCTCTGCGTTAGTGAAGGAAATATTGA

GGTGGAAACCGGCTACTCCGATTGGCGTACCCCACTTAGCCAGCGAGGATGACG

TTTACAACGGATATTACATACCAAAACGTGCGGTTGTCATAGGCAACAGCTGGGC

TATGCTTCATGATGAGGAAACTTATCCGGACCCAAGCACCTTTAACCCTGACAGA

TTTTTGACCACAAATAAAAGCACTGGAAAATTGGAATTAGATCCCACAGTGAGA

GATCCCGCTTTAATGGCCTTCGGATTTGGTAGACGTATGTGTCCAGGACGTGATG

TAGCTCTTTCTGTCATATGGCTGACTATCGCAAGCGTTTTAGCAACGTTTAATATT

-continued

ACCAAGGCGATAGACGAAAACGGGAAGGAACTGGAACCGGATGTACAGTACTG

GAGCGGTCTAATCGTCCACCCGCTGCCATTCAAATGTACGATCAAGCCAAGATCA

AAGGCAGCGGAAGAACTTGTGAAATCTGGCGCAGACGCCTATTAA (*Psilocybe cubensis* (PSIK gene))

SEQ ID NO: 7

ATGGCATTCGACTTGAAAACTGAAGACGGGCTAATAACTTACCTAACGAAACAC

CTTTCTTTGGATGTGGATACATCAGGTGTGAAAAGGTTAAGCGGTGGCTTCGTTA

ACGTGACCTGGAGAATAAAACTAAACGCACCCTATCAGGGTCACACATCAATAA

TTCTAAAGCACGCACAGCCGCATATGTCAACCGACGAAGACTTCAAAATTGGCG

TGGAGCGTTCCGTCTATGAGTACCAGGCTATCAAACTTATGATGGCCAATAGGGA

GGTGCTAGGGGGTGTTGACGGGATCGTGTCTGTGCCAGAGGGGTTGAACTACGA

CCTTGAAAATAATGCATTGATCATGCAGGACGTAGGTAAGATGAAGACCCTATT

AGACTACGTAACGGCAAAACCCCCGCTTGCGACTGATATAGCACGTTTGGTAGGT

ACAGAGATTGGGGGTTTCGTGGCTAGACTGCATAACATAGGGAGGGAGAGGAGA

GACGACCCGGAGTTCAAGTTTTTCTCTGGAAATATAGTCGGCAGGACAACAAGC

GATCAACTATACCAAACAATTATCCCTAACGCAGCTAAGTACGGGGTAGATGAC

CCTCTACTGCCTACCGTTGTAAAAGATCTGGTCGATGATGTCATGCACAGTGAGG

AGACTCTTGTAATGGCGGATTTATGGAGCGGCAATATACTTCTACAGTTGGAGGA

GGGGAATCCTTCAAAGTTACAGAAAATCTACATTTTAGATTGGGAATTGTGTAAA

TACGGCCCAGCTTCACTAGACCTTGGGTATTTCTTGGGTGATTGCTACCTGATTTC

TCGTTTCCAAGATGAGCAGGTCGGCACAACTATGAGACAAGCCTACTTACAAAG

CTACGCTCGTACCTCTAAACATTCCATAAACTACGCCAAGGTCACTGCGGGAATT

GCAGCACATATAGTGATGTGGACAGACTTTATGCAGTGGGGGAGTGAGGAAGAG

AGAATTAACTTCGTCAAGAAAGGCGTGGCCGCCTTCCATGACGCAAGAGGGAAC

AATGATAATGGTGAAATCACCTCTACTCTGTTGAAGGAGAGTTCAACTGCCTAA (*Psilocybe cyanescens* (PSIK gene))

SEQ ID NO: 8

ATGACTTTCGATCTAAAAACGGAGGAGGGCTTATTATCTTATCTTACCAAGCATT

TAAGTTTAGACGTAGCACCGAATGGTGTCAAAAGATTATCTGGTGGATTCGTCAA

TGTGACTTGGAGGGTAGGGTTAAATGCACCGTACCATGGGCACACGTCTATAATC

CTTAAACACGCTCAACCACATTTAAGCTCCGATATTGACTTCAAAATAGGGGTGG

AAAGAAGTGCGTATGAGTACCAGGCTTTGAAGATTGTCTCTGCCAACAGCAGCCT

ACTTGGTTCTTCTGATATCCGTGTCTCAGTTCCAGAAGGTTTGCACTATGATGTTG

TGAATAACGCCCTAATCATGCAGGACGTGGGTACAATGAAGACCTTGCTGGACT

ATGTTACAGCGAAACCCCCTATATCTGCTGAAATTGCCAGCCTAGTAGGTAGTCA

GATTGGCGCTTTCATAGCAAGATTACACAATTTGGGCAGAGAAAATAAAGATAA

GGACGACTTTAAATTTTTCTCCGGAAATATAGTTGGGAGGACGACGGCAGACCA

ACTGTATCAGACCATAATTCCTAATGCGGCAAAATATGGAATCGATGACCCAATT

CTTCCAATAGTTGTCAAAGAACTTGTTGAAGAAGTCATGAACTCAGAGGAAACC

CTGATTATGGCGGACCTATGGAGCGGTAATATCTTGCTACAGTTCGACGAGAACA

GTACGGAACTAACCCGTATTTGGCTGGTAGACTGGGAGCTATGCAAGTACGGGC

CGCCGTCACTGGATATGGGTTACTTCTTGGGCGACTGCTTTTTGGTAGCTAGATTC

CAAGACCAACTTGTAGGCACATCTATGAGACAAGCATACCTTAAAAGCTACGCA

CGTAACGTAAAAGAGCCGATCAACTATGCTAAGGCCACAGCAGGCATCGGCGCT

CATTTGGTAATGTGGACTGACTTCATGAAGTGGGGTAACGATGAAGAAAGGGAG

GAGTTCGTGAAAAAGGGGGTCGAAGCATTCCACGAGGCCAACGAAGACAATAG

GAACGGAGAGATAACGAGCATATTGGTGAAAGAGGCATCACGTACGTAA (*Psilocybe cubensis* (PSIM gene))

SEQ ID NO: 9

ATGCACATCAGAAACCCCTATAGAACCCCCATAGATTACCAGGCGCTGAGTGAG

GCCTTTCCACCATTGAAGCCCTTTGTATCCGTAAACGCTGATGGTACGAGTTCCG

TAGATCTAACGATCCCGGAGGCGCAACGTGCGTTCACTGCCGCATTGTTACATAG

AGATTTCGGGCTAACCATGACTATACCGGAAGATAGACTGTGCCCTACTGTCCCT

AACAGGTTAAATTATGTACTGTGGATTGAAGATATTTTCAACTACACGAATAAGA

CCCTGGGGCTGAGCGATGACAGACCGATAAAGGGGGTGGATATTGGCACAGGCG

CCAGCGCAATATACCCTATGCTTGCTTGCGCCAGGTTTAAGGCATGGTCCATGGT

AGGGACAGAGGTAGAACGTAAATGTATTGATACGGCTAGACTAAATGTCGTCGC

CAATAATCTACAGGATAGATTGAGTATATTAGAGACATCCATCGACGGTCCCATT

CTTGTTCCAATCTTCGAGGCCACAGAAGAATATGAGTATGAGTTCACCATGTGTA

ATCCGCCATTCTACGATGGTGCGGCCGACATGCAGACCTCTGACGCGGCCAAAG

GATTCGGCTTTGGAGTGGGGGCCCCTCACTCTGGAACAGTTATCGAAATGTCCAC

TGAAGGAGGGGAGTCCGCATTCGTAGCCCAGATGGTGAGAGAGAGCTTGAAACT

GCGTACCAGATGCAGATGGTATACGTCTAATCTTGGGAAATTAAAAAGCCTAAA

GGAGATTGTGGGTCTTTTAAAAGAGCTGGAGATTTCCAACTACGCCATAAACGA

GTACGTCCAAGGGTCTACCAGAAGATACGCCGTCGCGTGGTCTTTTACTGACATT

CAGCTTCCAGAGGAGCTATCTCGTCCCAGTAACCCGGAATTGTCCTCCTTGTTTTA

A (*Psilocybe cyanescens* (PSIM gene))

SEQ ID NO: 10

ATGCATATCAGGAATCCGTACCGTGACGGCGTGGACTACCAGGCATTAGCCGAG

GCTTTCCCGGCGCTAAAGCCACACGTCACTGTCAATTCAGACAATACAACTTCTA

TAGATTTCGCGGTACCCGAGGCCCAGAGACTTTACACCGCAGCATTACTTCATAG

GGACTTTGGTTTAACCATAACCTTACCCGAGGATAGACTATGTCCTACGGTCCCG

AATAGATTGAACTATGTGTTGTGGGTGGAAGATATACTGAAGGTTACGTCAGAC

GCATTGGGATTACCGGATAATAGACAAGTGAAAGGTATTGATATTGGAACAGGA

GCAAGCGCAATTTATCCCATGTTAGCTTGTTCCAGGTTTAAGACTTGGTCCATGG

TAGCTACAGAGGTGGATCAAAAATGCATAGATACCGCAAGGCTAAACGTAATAG

CTAATAACCTTCAGGAGAGATTGGCAATCATAGCCACTTCCGTGGACGGGCCTAT

TCTTGTTCCTCTGTTGCAGGCTAATTCCGACTTTGAATATGACTTCACCATGTGCA

ATCCGCCCTTTTACGACGGCGCCTCTGATATGCAGACAAGTGATGCCGCTAAAGG

CTTTGGCTTCGGAGTAAACGCACCTCACACTGGGACAGTACTTGAAATGGCGACA

GAAGGAGGGGAAAGTGCGTTCGTTGCCCAAATGGTTCGTGAGTCCTTGAACCTG

CAGACTAGATGCAGGTGGTTCACATCTAATTTGGGTAAACTAAAATCACTGTACG

AGATTGTGGGTCTATTAAGAGAACACCAGATTTCTAACTACGCCATAAATGAGTA

TGTACAAGGCGCAACTCGTAGGTATGCAATTGCGTGGAGTTTCATAGATGTAAGA

CTGCCCGACCATTTGTCCAGACCATCTAATCCCGATCTATCCAGTTTGTTTTAA (*Panaeolus cyanescens* (PSIM gene))

SEQ ID NO: 11

ATGCATAACCGTAACCCGTATAGGGACGTGATTGATTACCAAGCACTTGCGGAA

GCCTACCCGCCCCTAAAACCCCACGTCACGGTGAACGCGGATAACACGGCATCC

ATAGATCTTACGATCCCCGAGGTCCAGAGGCAATACACAGCAGCTCTTTTACATC

GTGATTTCGGATTAACTATCACACTACCAGAAGATAGGCTGTGCCCGACAGTACC

GAACCGTTTAAACTATGTATTGTGGATAGAGGATATATTTCAGTGTACGAATAAG

GCTCTGGGATTGTCAGATGACAGACCCGTTAAGGGGGTAGATATAGGGACCGGC

GCCTCCGCCATCTATCCAATGCTTGCTTGCGCGAGGTTTAAGCAGTGGTCCATGA

TTGCCACAGAAGTGGAGCGTAAGTGCATAGATACAGCGAGATTGAATGTCCTGG

CGAATAACTTACAGGACCGTTTGTCAATTCTTGAGGTTTCAGTAGACGGCCCGAT

TTTGGTACCCATCTTTGATACCTTCGAGCGTGCGACAAGCGATTACGAATTTGAG

TTCACGATGTGTAACCCTCCATTTTACGACGGGGCCGCGGATATGCAAACATCAG

ATGCAGCTAAGGGTTTCGGTTTTGGAGTTAACGCTCCACACTCCGGTACCGTGAT

AGAGATGGCTACTGAAGGAGGTGAGGCTGCTTTTGTGGCGCAAATGGTCCGTGA

GAGCATGAAGTTACAGACAAGGTGTCGTTGGTTTACAAGCAACTTAGGCAAGCT

AAAATCACTGCATGAAATTGTTGCTTTGTTGAGAGAATCCCAGATCACAAACTAT

GCCATAAATGAGTACGTTCAGGGACGACGAGAAGGTACGCTCTTGCTTGGTCCT

TCACAGACATAAAACTTACTGAGGAACTTTACAGGCCCTCCAATCCAGAATTAGG

ACCTCTTTGCAGCACATTTGTCTAA (*Gymnopilus dilepis* (PSIM gene))

SEQ ID NO: 12

ATGCACATTAGAAACCCTTACTTAACACCTCCGGACTACGAGGCCCTTGCGGAGG

CCTTCCCCGCACTAAAGCCTTATGTTACAGTTAACCCCGATAAGACTACTACAAT

TGACTTTGCCATACCGGAGGCTCAGAGATTATACACGGCTGCTCTACTTTACAGG

GACTTTGGACTGACAATAACATTGCCGCCGGATAGGTTATGCCCAACCGTGCCCA

ATAGGCTTAATTATGTTTTGTGGATTCAGGACATTCTGCAGATTACCTCCGCTGCC

TTGGGCTTGCCAGAGGCTAGACAAGTAAAGGGAGTAGACATAGGTACCGGAGCG

GCAGCGATATACCCTATTCTTGGTTGCAGCCTTGCAAAGAATTGGTCTATGGTGG

GGACAGAGGTCGAACAAAAATGTATCGACATAGCGCGTCAAAACGTGATTTCAA

ATGGATTGCAGGATAGGATAACCATAACTGCTAATACCATAGACGCTCCCATTCT

GCTGCCCTTATTTGAAGGAGACAGTAACTTCGAATGGGAGTTCACCATGTGTAAC

CCGCCATTTTACGACGCGCTGCGGACATGGAGACAAGCCAGGACGCTAAAGGC

TTCGGGTTCGGCGTCAACGCCCCGCATACAGGAACAGTGGTGGAAATGGCCACG

GACGGTGGTGAGGCTGCATTCGTCAGCCAAATGGTGAGAGAGTCCTTGCACCTA

AAGACACGTTGTAGATGGTTCACGTCCAATCTAGGTAAATTGAAGAGTCTACATG

AAATTGTGGGATTGTTGCGTGAACACCAAATTACCAACTACGCGATAAATGAAT

ATGTTCAGGGAACGACACGTAGATACGCGATTGCATGGTCATTTACTGACCTACG

TCTATCAGACCACCTGCCACGTCCTCCGAACCCCGATCTATCAGCCCTATTTTAA

-continued (*Gymnopilus junonius* (PSIM gene))
SEQ ID NO: 13
ATGCACTCTCGTAACCCTTATAGATCCCTCCTGATTTCGCGGCATTAAGTGCGG

CTTATCCTCCGCTGTCACCATACATAACTACCGATCTAAGCAGCGGTCGTAAAAC

AATTGACTTTAGAAATGAGGAAGCGCAACGTCGTCTAACTGAGGCTATCATGTTG

CGTGACTTCGGCGTTGTGTTAAACATACCATCTAACAGGCTGTGCCCGCCTGTGC

CGAATCGTATGAACTATGTACTTTGGATACAAGATATAGTTTACGCGCACCAGAC

AATACTGGGAGTGAGTTCTCGTCGTATCAGAGGTCTTGATATTGGTACTGGTGCT

ACCGCTATATATCCTATACTGGCATGCAAGAAAGAGCAGAGCTGGGAGATGGTT

GCAACTGAATTGGACGACTACTCCTATGAGTGTGCATGTGATAACGTGTCATCCA

ACAATATGCAGACTTCCATTAAAGTAAAGAAGGCTTCGGTAGATGGGCCCATCCT

GTTCCCAGTGGAAAACCAAAATTTCGACTTTAGCATGTGCAACCCGCCTTTCTAC

GGCTCTAAGGAGGAGGTGGCGCAATCCGCAGAGTCAAAAGAACTGCCGCCCAAT

GCTGTTTGCACGGGTGCAGAGATCGAGATGATATTTAGTCAAGGAGGAGAAGAG

GGTTTCGTAGGTAGAATGGTAGAGGAATCAGAGAGGTTGCAAACGAGATGCAAA

TGGTACACTTCAATGCTTGGTAAGATGTCTAGTGTAAGCACTATAGTTCAGGCTC

TGCGTGCGAGATCAATTATGAATTATGCTTTGACAGAATTTGTACAAGGACAAAC

CCGTAGGTGGGCGATAGCTTGGTCTTTCTCCGACACTCACTTACCGGATGCCGTC

AGTAGAATCTCTAGTTAA (*Psilocybe cubensis* (PSID gene))
SEQ ID NO: 14
MQVIPACNSAAIRSLCPTPESFRNMGWLSVSDAVYSEFIGELATRASNRNYSNEFGL

MQPIQEFKAFIESDPVVHQEFIDMFEGIQDSPRNYQELCNMFNDIFRKAPVYGDLGPP

VYMIIVIAKLMNTRAGFSAFTRQRLNLHFKKLFDTWGLFLSSKDSRNVLVADQFDDR

HCGWLNERALSAMVKHYNGRAFDEVFLCDKNAPYYGFNSYDDFFNRRFRNRDIDR

PVVGGVNNTTLISAACESLSYNVSYDVQSLDTLVFKGETYSLKHLLNNDPFTPQFEH

GSILQGFLNVTAYHRWHAPVNGTIVKIINVPGTYFAQAPSTIGDPIPDNDYDPPPYLKS

LVYFSNIAARQIMFIEADNKEIGLIFLVFIGMTEISTCEATVSEGQHVNRGDDLGMFHF

GGSSFALGLRKDCRAEIVEKFTEPGTVIRINEVVAALKA (*Psilocybe cyanescens* (PSID gene))
SEQ ID NO: 15
MQVLPACQSSALKTLCPSPEAFRKLGWLPTSDEVYNEFIDDLTGRTCNEKYSSQVTL

LKPIQDFKTFIENDPIVYQEFISMFEGIEQSPTNYHELCNMFNDIFRKAPLYGDLGPPV

YMIIVIARIMNTQAGFSAFTKESLNFHFKKLFDTWGLFLSSKNSRNVLVADQFDDKHY

GWFSERAKTAMMINYPGRTFEKVFICDEHVPYHGFTSYDDFFNRRFRDKDTDRPVV

GGVTDTTLIGAACESLSYNVSHNVQSLDTLVIKGEAYSLKHLLHNDPFTPQFEHGSII

QGFLNVTAYHRWHSPVNGTIVKIVNVPGTYFAQAPYTIGSPIPDNDRDPPPYLKSLVY

FSNIAARQIMFIEADNKDIGLIFLVFIGMTEISTCEATVCEGQHVNRGDDLGMFHFGGS

SFALGLRKDSKAKILEKFAKPGTVIRINELVASVRK (*Gymnopilus junonius* (PSID gene))
SEQ ID NO: 16
MSSPRIVLHRVGGWLPKDQNVLEAWLSKKIAKAKTRNRAPKDWAPVIQDFQRLIET

DAEIYMGFHQMFEQVPKKTPYDKDPTNEQWQVRNYMHMLDLFDLIITEAPDFEQND

LVGFPINAILDWPMGTPGGLTAFINPKVNIMFHKMFDVWAVFLSSPASCYVLNTSDS

GWFGPAATAAIPNFKETFICDPSLPYLGYTSWDNFFTRLFRPGVRPVEFPNNDAIVNS

```
ACESTVYNIAPNIKPLDKFWIKGEPYSLNHILNNDPYASQFVGGTISQAFLSALNYHR

WASPVNGNIVKVVNVPGTYYAESPVTGFGNPEGPDPAAPNLSQGFITAVAARALIFIE

ADNPNIGLMCFVGVGMAEVSTCEVTVSVGDVVKKGDEIGMFHFGGSTHCLIFRPQT

KITFNPDYPVSTAVPLNAAVATVV
```

(*Psilocybe cubensis* (PSIH gene))
SEQ ID NO: 17
```
MIAVLFSFVIAGCIYYIVSRRVRRSRLPPGPPGIPIPFIGNMFDMPEESPWLTFLQWGRD

YNTDILYVDAGGTEMVILNTLETITDLLEKRGSIYSGRLESTMVNELMGWEFDLGFIT

YGDRWREERRMFAKEFSEKGIKQFRHAQVKAAHQLVQQLTKTPDRWAQHIRHQIA

AMSLDIGYGIDLAEDDPWLEATHLANEGLAIASVPGKFWVDSFPSLKYLPAWFPGAV

FKRKAKVWREAADHMVDMPYETMRKLAPQGLTRPSYASARLQAMDLNGDLEHQE

HVIKNTAAEVNVGGGDTTVSAMSAFILAMVKYPEVQRKVQAELDALTNNGQIPDYD

EEDDSLPYLTACIKELFRWNQIAPLAIPHKLMKDDVYRGYLIPKNTLVFANTWAVLN

DPEVYPDPSVFRPERYLGPDGKPDNTVRDPRKAAFGYGRRNCPGIHLAQSTVWIAGA

TLLSAFNIERPVDQNGKPIDIPADFTTGFFRHPVPFQCRFVPRTEQVSQSVSGP
```

(*Psilocybe cyanescens* (PSIH gene))
SEQ ID NO: 18
```
MAPLTTMIPIVLSLLIAGCIYYINARRIKRSRLPPGPPGIPIPFIGNMFDMPSESPWLIF

LQWGQEYQTDIIYVDAGGTDMIILNSLEAITDLLEKRGSLYSGRLESTMVNELMGWEFD

FGFIPYGERWREERRMFAKEFSEKNIRQFRHAQVKAANQLVRQLTDKPDRWSHEIR

HQIASMALDIGYGIDLAEDDPWIAASELANEGLAVASVPGSFWVDTFPFLKYLPSWL

PGAEFKRNAKMWKEGADHMVNMPYETMKKLSAQGLTRPSYASARLQAMDPNGDL

EHQERVIKNTATQVNVGGGDTTVGAVSAFILAMVKYPEVQRKVQAELDEFTSKGRI

PDYDEDNDSLPYLSACFKELFRWGQIAPLAIAHRLIKDDVYREYTIPKNALVFANNW

YGRTVLNDPSEYPNPSEFRPERYLGPDGKPDDTVRDPRKAAFGYGRRVCPGIHLAQS

TVWIAGVALVSAFNIELPVDKDGKCIDIPAAFTTGFFR
```

(*Gymnopilus junonius* (PSIH gene))
SEQ ID NO: 19
```
MMSEMNGMDKLALLTTLLAAGFLYFKNKRRSALPFPPGPKKHPLLGNLLDLPKKLE

WETYRRWGKEYNSDVIHVSAGSVNLIIVNSFEAATDLFDKRSANYSSRPQFTMVREL

MGWNWLMSALIYGDKWREQRRLFQKHFSTTNAELYQNTQLEYVRKALQHLLEEPS

DFMGITRHMAGGVSMSLAYGLNIQKKNDPFVDLAQRAVHSITEASVPGTFWVDVMP

WLKYIPEWVPGAGFQKKARVWRKLQQDFRQVPYQAALKDMASGKAKPSFASECLE

TIDDNEDAQRQREVIKDTAAIVFAAGADTSLSGIHTLFAAMLCYPEVQKKAQEELDR

VLGGRRLPEFTDEPNMPYISALVKEILRWKPATPIGVPHLASEDDVYNGYYIPKRAVV

IGNSWAMLHDEETYPDPSTENPDRELTTNKSTGKLELDPTVRDPALMAFGEGRRMCP

GRDVALSVIWLTIASVLATENITKAIDENGKELEPDVQYWSGLIVHPLPFKCTIKPRSK

AAEELVKSGADAY
```

(*Psilocybe cubensis* (PSIK gene))
SEQ ID NO: 20
```
MAFDLKTEDGLITYLTKHLSLDVDTSGVKRLSGGEVNVTWRIKLNAPYQGHTSIILK

HAQPHMSTDEDEKIGVERSVYEYQAIKLMMANREVLGGVDGIVSVPEGLNYDLENN

ALEVIQDVGKMKTLLDYVTAKPPLATDIARLVGTEIGGEVARLHNIGRERRDDPEEKE

FSGNIVGRTTSDQLYQTIIPNAAKYGVDDPLLPTVVKDLVDDVMHSEETLVMADLW
```

-continued

SGNILLQLEEGNPSKLQKIYILDWELCKYGPASLDLGYELGDCYLISREQDEQVGTTM

RQAYLQSYARTSKHSINYAKVTAGIAAHIVMWTDFMQWGSEEERINFVKKGVAAFH

DARGNNDNGEITSTLLKESSTA (*Psilocybe cyanescens* (PSIK gene))
SEQ ID NO: 21
MTFDLKTEEGLLSYLTKHLSLDVAPNGVKRLSGGFVNVTWRVGLNAPYHGHTSILK

HAQPHLSSDIDFKIGVERSAYEYQALKIVSANSSLLGSSDIRVSVPEGLHYDVVNNALI

MQDVGTMKTLLDYVTAKPPISAEIASLVGSQIGAFIARLHNLGRENKDKDDFKFFSG

NIVGRTTADQLYQTIIPNAAKYGIDDPILPIVVKELVEEVMNSEETLIMADLWSGNILL

QFDENSTELTRIWLVDWELCKYGPPSLDMGYELGDCELVAREQDQLVGTSMRQAYL

KSYARNVKEPINYAKATAGIGAHLVMWTDFMKWGNDEEREEFVKKGVEAFHEANE

DNRNGEITSILVKEASRT (*Psilocybe cyanescens* (PSIM gene))
SEQ ID NO: 22
MHIRNPYRDGVDYQALAEAFPALKPHVTVNSDNTTSIDEAVPEAQRLYTAALLHRDF

GLTITLPEDRLCPTVPNRLNYVLWVEDILKVTSDALGLPDNRQVKGIDIGTGASAIYP

MLACSRFKTWSMVATEVDQKCIDTARLNVIANNLQERLAIIATSVDGPILVPLLQANS

DFEYDFTMCNPPFYDGASDMQTSDAAKGFGFGVNAPHTGTVLEMATEGGESAFVA

QMVRESLNLQTRCRWFTSNLGKLKSLYEIVGLLREHQISNYAINEYVQGATRRYAIA

WSFIDVRLPDHLSRPSNPDLSSLF (*Psilocybe cubensis* (PSIM gene))
SEQ ID NO: 23
MHIRNPYRTPIDYQALSEAFPPLKPFVSVNADGTSSVDLTIPEAQRAFTAALLHRDFG

LTMTIPEDRLCPTVPNRLNYVLWIEDIFNYTNKTLGLSDDRPIKGVDIGTGASAIYPML

ACARFKAWSMVGTEVERKCIDTARLNVVANNLQDRLSILETSIDGPILVPIFEATEEY

EYEFTMCNPPFYDGAADMQTSDAAKGFGFGVGAPHSGTVIEMSTEGGESAFVAQM

VRESLKLRTRCRWYTSNLGKLKSLKEIVGLLKELEISNYAINEYVQGSTRRYAVAWS

FTDIQLPEELSRPSNPELSSLF (*Panaeolus cyanescens* (PSIM gene))
SEQ ID NO: 24
MHNRNPYRDVIDYQALAEAYPPLKPHVTVNADNTASIDLTIPEVQRQYTAALLHRDE

GLTITLPEDRLCPTVPNRLNYVLWIEDIFQCTNKALGLSDDRPVKGVDIGTGASAIYP

MLACARFKQWSMIATEVERKCIDTARLNVLANNLQDRLSILEVSVDGPILVPIFDTFE

RATSDYEFEETMCNPPFYDGAADMQTSDAAKGEGEGVNAPHSGTVIEMATEGGEAA

FVAQMVRESMKLQTRCRWFTSNLGKLKSLHEIVALLRESQITNYAINEYVQGTTRRY

ALAWSFTDIKLTEELYRPSNPELGPLCSTFV (*Gymnopilus junonius* (PSIM gene))
SEQ ID NO: 25
MHSRNPYRSPPDFAALSAAYPPLSPYITTDLSSGRKTIDFRNEEAQRRLTEAIMLRDFG

VVLNIPSNRLCPPVPNRMNYVLWIQDIVYAHQTILGVSSRRIRGLDIGTGATAIYPILA

CKKEQSWEMVATELDDYSYECACDNVSSNNMQTSIKVKKASVDGPILFPVENQNFD

FSMCNPPFYGSKEEVAQSAESKELPPNAVCTGAEIEMIFSQGGEEGFVGRMVEESERL

QTRCKWYTSMLGKMSSVSTIVQALRARSIMNYALTEFVQGQTRRWAIAWSFSDTHL

PDAVSRISS

-continued (*Gymnopilus dilepis* (PSIM gene))

SEQ ID NO: 26

MHIRNPYLTPPDYEALAEAFPALKPYVTVNPDKTTTIDFAIPEAQRLYTAALLYRDFG

LTITLPPDRLCPTVPNRLNYVLWIQDILQITSAALGLPEARQVKGVDIGTGAAAIYPIL

GCSLAKNWSMVGTEVEQKCIDIARQNVISNGLQDRITITANTIDAPILLPLFEGDSNFE

WEFTMCNPPFYDGAADMETSQDAKGFGFGVNAPHTGTVVEMATDGGEAAFVSQM

VRESLHLKTRCRWFTSNLGKLKSLHEIVGLLREHQITNYAINEYVQGTTRRYAIAWSF

TDLRLSDHLPRPPNPDLSALF (*Saccharmyces cerevisiae* (ARO1 gene))

SEQ ID NO: 27

ATGGTTCAACTAGCCAAGGTTCCAATACTAGGAAACGATATAATACACGTTGGAT

ATAATATACACGATCATCTTGTAGAGACAATTATTAAACACTGTCCTTCTTCTACT

TACGTCATCTGTAACGATACTAACCTTAGCAAGGTACCTTATTACCAGCAACTGG

TTCTGGAGTTCAAAGCAAGTCTTCCCGAAGGCTCCAGACTACTAACCTACGTGGT

CAAACCGGGCGAGACGTCTAAGAGTAGGGAGACGAAGGCGCAGTTAGAGGATT

ATCTTTTAGTAGAAGGGTGCACTCGTGATACGGTCATGGTAGCCATCGGCGGAGG

TGTCATCGGTGACATGATCGGTTTCGTAGCCTCCACGTTCATGAGAGGTGTGAGG

GTAGTACAGGTTCCGACGTCTCTTTTAGCAATGGTAGACTCATCCATAGGCGGTA

AAACGGCGATCGATACTCCGCTAGGAAAGAACTTCATTGGAGCCTTTTGGCAGCC

AAAATTTGTTCTTGTGGATATCAAGTGGCTTGAAACACTAGCTAAACGTGAATTT

ATCAACGGCATGGCAGAAGTGATCAAGACAGCGTGCATCTGGAACGCTGATGAA

TTTACTCGTCTCGAATCCAACGCGTCACTGTTCCTAAACGTAGTAAATGGTGCGA

AAAATGTAAAGGTGACTAACCAGCTGACGAACGAGATAGATGAGATCAGCAACA

CGGATATTGAAGCCATGTTGGACCATACTTATAAACTGGTATTAGAGAGTATTAA

GGTTAAAGCGGAGGTGGTAAGCAGCGATGAAAGGGAGAGCAGTCTTAGGAACCT

TTTAAACTTCGGGCATAGCATAGGTCACGCGTATGAAGCCATACTGACACCCCAG

GCTTTACATGGAGAGTGCGTATCCATCGGCATGGTAAAAGAAGCAGAACTATCA

AGGTATTTTGGGATACTTTCTCCGACCCAGGTGGCGCGTCTAAGCAAAATTCTAG

TTGCGTACGGATTGCCCGTTAGCCCCGATGAGAAATGGTTTAAAGAGCTTACACT

TCATAAGAAGACACCCTTGGACATACTGCTAAAGAAGATGAGCATCGACAAGAA

AAATGAAGGAAGCAAGAAGAAGGTCGTAATCCTAGAGTCTATCGGCAAATGTTA

CGGAGACTCAGCTCAGTTTGTTTCAGACGAAGACTTACGTTTTATATTGACAGAT

GAAACACTAGTATATCCTTTTAAGGATATTCCCGCTGATCAGCAGAAAGTCGTGA

TTCCACCCGGAAGTAAATCAATAAGCAATCGTGCTTTAATCTTAGCAGCTCTGGG

GGAGGGACAGTGCAAGATCAAGAACCTATTACACTCCGACGACACCCAAACATAT

GCTGACCGCAGTCCACGAGTTAAAAGGTGCTACCATCAGTTGGGAGGATAACGG

AGAAACAGTGGTCGTAGAGGGCCATGGCGGGAGCACTCTATCGGCTTGTGCTGA

TCCCTTATACTTAGGCAACGCGGGGACGGCGAGTAGATTCTTAACATCACTGGCG

GCACTAGTGAACAGTACATCCTCCCAAAAGTATATCGTACTAACAGGCAACGCA

AGGATGCAGCAACGTCCGATAGCGCCCCTTGTTGACAGCTTACGTGCTAACGGG

ACAAAGATCGAGTACTTGAACAACGAAGGTTCTTTGCCGATCAAAGTGTACACT

GATTCTGTATTTAAAGGCGGCCGTATTGAGTTGGCTGCGACAGTTAGTTCCCAAT

ACGTGAGCAGTATCCTGATGTGTGCGCCTTACGCAGAAGAGCCCGTGACTTTAGC

-continued

```
TTTGGTAGGTGGGAAACCGATCAGTAAACTATACGTTGATATGACAATTAAGATG
ATGGAAAAGTTCGGCATCAATGTGGAGACCTCAACCACGGAACCCTACACATAC
TACATTCCGAAGGGGCATTACATTAATCCAAGTGAGTACGTAATCGAGAGCGAC
GCTTCATCCGCTACCTATCCGTTAGCATTCGCCGCAATGACCGGTACCACCGTAA
CAGTCCCCAACATCGGCTTTGAATCTCTGCAGGGCGACGCTAGATTCGCAAGAGA
CGTCCTAAAGCCGATGGGGTGTAAAATCACCCAAACGGCTACGTCTACAACCGT
CAGTGGACCACCCGTCGGTACGCTAAAGCCATTAAAACACGTTGATATGGAACC
AATGACAGACGCCTTCTTAACCGCATGCGTTGTAGCCGCAATCAGTCATGACTCC
GACCCCAATTCAGCGAACACTACTACTATCGAGGGGATCGCAAACCAAAGGGTT
AAAGAATGCAACAGAATCTTAGCGATGGCTACCGAGCTGGCAAAGTTTGGAGTA
AAGACAACAGAACTTCCCGATGGCATACAGGTCCATGGGCTAAATTCCATCAAG
GACCTTAAAGTCCCATCTGACAGCTCAGGACCCGTCGGAGTCTGTACTTATGATG
ACCATAGGGTTGCCATGTCATTTTCCCTTTTGGCTGGCATGGTAAACAGTCAGAA
TGAGAGAGATGAAGTGGCAAACCCAGTTAGGATCTTAGAGAGGCACTGCACCGG
AAAGACGTGGCCAGGCTGGTGGGACGTTCTGCACAGCGAACTTGGAGCGAAGCT
GGATGGTGCCGAGCCGCTAGAATGCACATCCAAAAAGAACTCTAAGAAGAGCGT
AGTCATAATAGGCATGAGAGCTGCGGGCAAAACTACTATCTCTAAGTGGTGCGC
AAGTGCGCTGGGTTACAAGTTGGTAGATTTAGATGAATTGTTCGAGCAGCAGCAT
AATAACCAATCAGTAAAACAATTTGTAGTCGAGAATGGTTGGGAGAAATTCAGA
GAGGAAGAGACCAGGATATTCAAGGAGGTTATTCAAAATTACGGCGACGACGGG
TATGTCTTTAGCACTGGGGGAGGGATCGTCGAATCCGCGGAGAGCAGGAAAGCA
CTAAAGGACTTCGCCAGTTCCGGTGGGTATGTGCTTCACTTACATCGTGATATAG
AGGAGACGATAGTCTTCCTACAAAGTGATCCATCCAGGCCGGCGTATGTTGAGG
AGATTAGGGAGGTCTGGAACCGTAGAGAAGGCTGGTATAAAGAATGTAGTAATT
TTAGCTTTTTCGCACCTCACTGTAGCGCAGAGGCGGAGTTTCAAGCACTTAGACG
TTCATTCAGTAAGTATATAGCTACGATCACGGGGGTCCGTGAAATAGAGATTCCT
AGTGGGAGGAGTGCGTTTGTATGCTTAACTTTTGACGATCTAACTGAGCAAACGG
AGAATCTGACGCCTATATGCTACGGGTGTGAAGCCGTAGAGGTGCGTGTTGATCA
TCTTGCCAATTATTCCGCAGACTTCGTTAGCAAGCAATTAAGCATACTGAGAAAA
GCGACCGACAGTATACCCATTATCTTCACCGTCCGTACTATGAAACAAGGCGGTA
ATTTTCCCGATGAAGAGTTCAAGACATTGCGTGAGTTGTACGACATAGCTCTTAA
AAACGGAGTGGAGTTCCTTGATTTGGAACTTACTCTGCCTACAGATATACAGTAC
GAAGTCATCAACAAGAGAGGTAATACGAAGATCATTGGGTCTCATCATGACTTC
CAGGGTTTGTACAGCTGGGACGATGCTGAATGGGAAAACAGATTCAATCAGGCA
CTGACTCTTGACGTAGATGTGGTGAAATTTGTGGGTACCGCGGTGAATTTCGAGG
ACAACTTACGTTTGGAACATTTTCGTGACACGCACAAAAATAAACCACTAATAGC
AGTTAACATGACGTCTAAGGGCTCAATCAGTAGGGTACTAAATAATGTATTGACT
CCGGTTACTTCAGACCTTTTACCGAACAGCGCAGCGCCTGGTCAATTGACGGTTG
CACAGATTAATAAAATGTATACATCTATGGGAGGAATTGAGCCTAAAGAGCTAT
TTGTGGTGGGGAAGCCAATCGGCCACTCAAGATCACCTATACTACACAATACTGG
```

-continued
```
GTATGAGATTTTGGGTCTACCTCACAAATTCGATAAATTTGAGACGGAAAGCGCA

CAATTAGTGAAGGAGAAATTGTTAGACGGGAACAAGAATTTCGGTGGTGCAGCG

GTGACCATCCCTTTAAAGCTAGACATAATGCAGTACATGGATGAACTTACGGACG

CTGCGAAGGTGATTGGGGCGGTAAACACAGTAATCCCTTTGGGTAACAAGAAAT

TCAAGGGTGATAATACGGACTGGTTAGGGATAAGGAACGCACTTATAAATAATG

GTGTGCCCGAGTACGTGGGGCATACTGCCGGACTTGTAATAGGTGCTGGTGGTAC

CAGTAGGGCGGCACTGTACGCTTTGCATAGCTTAGGTTGCAAGAAGATCTTTATC

ATCAATAGAACAACTAGTAAACTGAAGCCACTGATAGAATCACTACCCTCCGAG

TTTAACATCATTGGAATAGAGTCTACGAAATCCATCGAGGAGATTAAAGAACAC

GTCGGAGTCGCTGTTAGCTGCGTGCCTGCCGATAAGCCCTTAGATGACGAGCTAC

TGAGTAAGTTAGAACGTTTCCTTGTCAAGGGTGCACATGCGGCTTTCGTCCCAAC

ACTGCTAGAGGCTGCCTATAAACCCAGCGTAACACCTGTTATGACCATAAGTCAG

GACAAGTATCAATGGCACGTGGTGCCGGGTTCCCAGATGCTGGTCCATCAAGGT

GTTGCACAATTTGAAAAATGGACTGGTTTCAAGGGGCCCTTCAAAGCCATATTTG

ACGCCGTGACTAAAGAGTAA
```

(Saccharomyces cerevisiae (ARO2 gene))

SEQ ID NO: 28
```
ATGTCCACATTCGGTAAACTTTTCCGTGTCACTACATACGGCGAGTCACACTGCA

AATCTGTGGGGTGCATAGTAGACGGCGTTCCGCCGGGCATGAGTTTAACCGAAG

CGGACATTCAACCTCAGCTTACCCGTAGGAGGCCCGGTCAGAGCAAGTTATCCAC

CCCGAGGGACGAAAAGGACCGTGTAGAGATCCAAAGCGGAACGGAATTTGGGA

AGACACTTGGTACGCCTATCGCTATGATGATTAAAAACGAGGATCAACGTCCGC

ACGATTACTCCGACATGGACAAGTTCCCTAGGCCGAGTCACGCCGATTTTACGTA

CTCAGAGAAATACGGAATAAAAGCCTCCAGCGGTGGGGCCGTGCTTCCGCGAG

AGAAACCATTGGAAGAGTAGCATCCGGTGCAATAGCAGAGAAGTTCCTAGCACA

GAACTCAAATGTTGAAATTGTCGCTTTCGTCACGCAAATAGGTGAGATCAAGATG

AACCGTGACAGTTTCGACCCAGAATTTCAACACCTTCTAAATACAATTACGAGGG

AGAAGGTAGATAGCATGGGTCCAATAAGATGCCCCGACGCTTCCGTCGCGGGAT

TGATGGTGAAGGAAATTGAAAAATATCGTGGGAACAAGGATTCTATTGGGGGTG

TAGTAACTTGCGTAGTCAGAAATCTACCTACAGGGTTGGGTGAACCGTGTTTTGA

CAAACTGGAGGCGATGCTGGCACATGCCATGTTATCCATACCAGCAAGTAAAGG

ATTTGAAATAGGATCTGGCTTCCAGGGTGTAAGCGTACCAGGAAGCAAACACAA

TGATCCCTTTTACTTTGAAAAAGAGACTAACCGTCTTCGTACAAAGACAAACAAC

TCCGGTGGGGTGCAAGGGGGCATCTCTAATGGTGAGAACATTTACTTTTCCGTAC

CATTTAAGAGCGTGGCTACAATAAGCCAAGAGCAAAAGACCGCAACTTACGATG

GAGAAGAAGGAATCCTCGCAGCTAAGGGTAGGCACGATCCTGCGGTCACACCGC

GTGCAATTCCCATAGTGGAAGCTATGACCGCCCTAGTACTAGCAGATGCGTTACT

AATACAGAAAGCCAGGGATTTTTCTAGGTCAGTCGTACATTAA
```

(Saccharomyces cerevisiae (ARO3 gene))

SEQ ID NO: 29
```
ATGTTCATCAAGAATGACCATGCTGGTGATAGAAAGAGACTAGAGGACTGGCGT

ATAAAGGGTTATGACCCTCTAACTCCGCCTGATTTGCTACAGCACGAGTTTCCTA

TATCAGCAAAAGGGGAAGAAAATATCATCAAGGCTCGTGATAGTGTATGTGATA
```

TACTGAACGGAAAGGATGACAGACTTGTGATAGTAATTGGACCCTGTTCTCTGCA

TGATCCGAAGGCGGCCTACGACTATGCCGACAGATTAGCCAAAATATCCGAAAA

GCTGTCAAAAGATCTTTTAATTATCATGCGTGCATACCTAGAGAAGCCTCGTACA

ACCGTTGGATGGAAAGGGTTGATAAACGACCCGGATATGAACAATAGTTTTCAG

ATTAATAAAGGCCTTCGTATAAGCCGTGAGATGTTTATAAAACTAGTTGAGAAAT

TACCTATTGCAGGAGAAATGCTTGACACGATTTCCCCTCAGTTCTTATCTGACTGT

TTCTCACTAGGTGCAATTGGTGCTAGGACTACCGAGTCACAGTTACATCGTGAAC

TGGCCAGCGGTCTGTCTTTCCCCATTGGCTTTAAAAATGGTACCGATGGTGGCCT

TCAAGTAGCAATTGATGCTATGAGAGCTGCGGCCCACGAACACTACTTTTTGTCT

GTGACCAAACCTGGCGTAACAGCGATTGTGGGAACTGAAGGGAACAAGGACACC

TTCCTAATCCTGAGAGGGGCAAGAACGGGACTAATTTTGACAAGGAGTCAGTT

CAAAACACTAAGAAGCAATTGGAGAAGGCGGGCCTTACTGACGATTCTCAGAAG

AGAATCATGATAGACTGCAGCCATGGCAACTCAAATAAAGATTTCAAAAATCAA

CCCAAAGTCGCCAAGTGTATCTACGATCAACTAACCGAAGGAGAAAATAGTTTA

TGCGGGGTGATGATAGAGAGTAATATAAACGAAGGAAGACAGGATATTCCTAAG

GAAGGCGGAAGAGAGGGTCTGAAGTACGGGTGTTCTGTGACAGACGCTTGCATA

GGATGGGAGAGCACGGAACAGGTTTTGGAGCTGCTGGCAGAAGGGGTGCGTAAT

AGAAGGAAAGCCTTAAAGAAGTAA (Saccharomyces cerevisiae (ARO4 K2229L gene))

SEQ ID NO: 30

ATGAGCGAATCTCCGATGTTCGCCGCAAACGGCATGCCTAAGGTAAATCAAGGG

GCCGAGGAGGACGTGAGAATATTAGGTTATGACCCGCTTGCCAGTCCTGCATTGC

TTCAGGTACAGATTCCAGCAACGCCAACGTCCTTAGAAACAGCAAAAAGGGGAC

GTCGTGAAGCTATAGACATCATCACTGGCAAGGACGACCGTGTCCTAGTAATAGT

TGGTCCGTGCTCTATCCATGACCTTGAGGCTGCACAGGAGTATGCACTAAGGTTG

AAGAAATTGTCTGATGAACTGAAAGGTGATCTTAGTATAATCATGCGTGCATATT

TAGAGAAACCGCGTACGACGGTAGGCTGGAAAGGGCTAATTAACGATCCGGATG

TGAATAATACCTTTAACATCAACAAGGGTCTACAGAGTGCGCGTCAGTTATTCGT

GAACTTAACAAATATCGGACTGCCGATAGGCTCCGAGATGCTGGACACGATATC

TCCCCAGTATTTGGCTGACCTTGTTTCTTTTGGAGCTATAGGTGCAAGGACTACTG

AGAGTCAGTTACATAGAGAGTTGGCATCAGGACTTAGCTTCCCTGTAGGATTTAA

GAACGGTACAGACGGCACTCTTAATGTCGCGGTCGATGCCTGCCAGGCAGCCGC

CCATTCACATCATTTTATGGGAGTGACATTACACGGGGTGGCCGCTATCACAACG

ACTAAAGGGAATGAGCACTGTTTTGTTATCCTTAGAGGAGGAAAGAAAGGTACG

AATTATGATGCGAAAAGTGTAGCAGAGGCCAAAGCGCAACTTCCTGCCGGTTCA

AACGGACTTATGATTGACTATTCCCATGGAAACTCAAATAAGGACTTTAGGAATC

AGCCAAAAGTTAACGATGTGGTATGCGAACAGATCGCGAACGGTGAAAATGCGA

TTACGGGTGTTATGATCGAGTCAAATATAAATGAAGGTAACCAAGGTATCCCGG

CAGAGGGCAAAGCGGGCCTGAAGTACGGTGTATCTATTACGGATGCCTGTATAG

GTTGGGAGACAACCGAAGACGTCCTAAGGAAACTTGCCGCCGCGGTTAGACAGA

GACGTGAAGTCAATAAGAAGTAA

-continued (Escherichia coli (AROL gene))
SEQ ID NO: 31
ATGACCCAGCCATTATTTCTGATCGGTCCTCGTGGGTGCGGGAAAACGACGGTTG

GCATGGCCTTAGCTGACAGTTTGAATCGTAGATTCGTGGACACCGACCAGTGGCT

ACAGTCTCAGCTTAACATGACGGTGGCCGAAATTGTAGAACGTGAAGAATGGGC

TGGTTTTCGTGCAAGAGAAACAGCCGCATTGGAAGCTGTGACGGCGCCTTCAAC

GGTGATAGCTACGGGAGGTGGTATTATTTTGACCGAATTTAATAGGCACTTCATG

CAGAATAATGGCATAGTGGTTTACCTATGCGCTCCTGTGTCTGTCTTGGTAAACC

GTTTGCAAGCCGCACCAGAAGAAGACTTGCGTCCAACCCTGACGGGGAAGCCAC

TGTCTGAGGAAGTGCAAGAGGTACTGGAGGAAAGGGACGCTCTATACCGTGAGG

TGGCTCACATCATAATTGACGCTACGAATGAGCCATCACAGGTAATTTCTGAGAT

CCGTTCAGCGTTGGCCCAAACCATCAATTGTTAA (Saccharomyces cerevisiae (TRP1 gene))
SEQ ID NO: 32
ATGTCAGTGATTAACTTTACAGGCTCCTCAGGTCCCTTGGTCAAGGTCTGCGGCT

TGCAATCAACAGAGGCCGCTGAATGCGCCCTAGACTCAGATGCAGACCTTTTAG

GCATCATCTGTGTCCCCAACAGAAAGCGTACTATTGATCCTGTTATTGCGCGTAA

GATCAGTTCTTTGGTCAAGGCGTATAAGAACTCCTCAGGAACCCCCAAGTATCTG

GTAGGGGTATTCAGGAATCAACCTAAAGAAGACGTCTTGGCCCTAGTTAATGACT

ACGGCATAGACATAGTCCAGTTGCACGGAGACGAAAGCTGGCAAGAATATCAGG

AATTTTTGGGGCTGCCGGTTATAAAAAGGCTGGTTTTCCCTAAGGACTGTAACAT

ACTGTTATCAGCCGCATCACAGAAGCCGCATTCCTTTATACCTCTTTTCGACTCCG

AGGCCGGAGGCACTGGTGAATTACTGGACTGGAACAGCATTTCAGATTGGGTAG

GGAGGCAGGAGAGCCCAGAATCTCTTCATTTTATGTTGGCAGGGGGCCTTACGCC

GGAAAATGTTGGAGATGCATTGAGGTTGAACGGAGTTATAGGTGTGGATGTCAG

TGGTGGGGTTGAAACGAATGGTGTTAAAGACAGCAACAAAATAGCAAATTTTGT

CAAGAATGCCAAAAAGTAA (Saccharomyces cerevisiae (TRP2 S76L gene))
SEQ ID NO: 33
ATGACGGCGAGCATTAAAATTCAGCCAGACATTGACAGTTTAAAGCAGTTGCAG

CAACAGAATGACGACTCTTCCATTAACATGTATCCCGTGTATGCGTATCTGCCTT

CTTTGGATTTGACACCTCACGTTGCTTACTTAAAGTTAGCTCAACTTAATAATCCA

GATAGAAAGGAGTCTTTCTTACTTGAAAGTGCTAAGACCAATAATGAGCTGGAC

AGATATCTTTTCATAGGGATCAGTCCAAGGAAGACCATTAAGACCGGGCCCACT

GAAGGCATTGAGACTGACCCATTAGAAATCCTTGAAAAAGAAATGTCTACTTTCA

AAGTCGCCGAAAACGTCCCAGGCCTTCCCAAATTAAGCGGCGGGGCGATAGGTT

ACATATCATACGACTGTGTACGTTACTTCGAACCCAAGACTAGGCGTCCCTTGAA

AGATGTGCTTAGGTTACCAGAGGCGTACTTGATGCTTTGTGACACGATAATCGCA

TTTGACAATGTCTTCCAAAGGTTTCAAATTATTCACAATATTAACACAAACGAAA

CGTCTTTGGAGGAAGGATACCAGGCGGCTGCGCAGATAATCACGGATATTGTAT

CTAAGTTGACAGACGACAGCTCCCCCATTCCGTACCCGGAGCAACCCCCTATCAA

ACTAAACCAAACCTTTGAATCCAACGTAGGCAAAGAGGGGTATGAAAATCACGT

CTCCACTCTCAAAAAGCACATAAAGAAAGGTGACATAATCCAAGGTGTGCCCAG

CCAGAGAGTGGCGAGGCCTACATCTTTACATCCATTCAACATATATAGGCATCTT

-continued

AGAACCGTGAACCCATCACCTTATCTATTTTACATAGACTGCCTAGATTTCCAGA

TAATAGGGGCTAGTCCCGAATTGCTGTGTAAATCAGATTCAAAGAATCGTGTTAT

TACACACCCCATAGCTGGCACAGTCAAGAGGGGTGCTACCACTGAGGAAGATGA

CGCTCTGGCAGATCAGCTACGTGGTTCTTTGAAAGATAGGGCTGAGCATGTTATG

CTGGTTGACTTAGCAAGAAACGACATCAATCGTATATGCGATCCCCTAACGACTT

CCGTTGACAAACTTTTGACCATTCAGAAGTTCAGCCACGTACAGCACTTAGTCTC

TCAGGTCTCTGGCGTCCTAAGGCCTGAGAAAACTCGTTTCGATGCATTCAGAAGC

ATATTTCCCGCGGGTACAGTGAGTGGGGCCCCAAAGGTGCGTGCAATGGAGCTT

ATAGCCGAGCTAGAAGGCGAGCGTAGGGGAGTGTACGCAGGGGCCGTAGGCCAT

TGGTCTTATGACGGCAAGACCATGGATAATTGTATTGCACTAAGGACCATGGTCT

ATAAAGATGGGATTGCATACTTGCAGGCAGGAGGTGGGATTGTCTATGACAGCG

ATGAGTACGATGAGTATGTAGAAACAATGAATAAAATGATGGCGAATCATTCCA

CGATAGTGCAGGCGGAGGAGTTATGGGCGGATATTGTGGGTAGTGCATAA (Saccharomyces cerevisiae (TRP3 gene))

SEQ ID NO: 34

ATGTCTGTCCACGCAGCCACCAACCCGATAAATAAGCATGTCGTTCTGATTGATA

ATTACGACTCCTTCACGTGGAATGTTTATGAGTATCTTTGCCAGGAGGGAGCGAA

GGTTAGCGTTTACCGTAATGACGCTATCACGGTCCCAGAAATTGCAGCACTGAAT

CCCGATACCCTTCTGATATCACCAGGCCCGGGCCATCCCAAGACAGATTCTGGTA

TTAGCAGAGATTGCATCAGATACTTCACTGGAAAAATTCCAGTTTTTGGGATATG

TATGGGCAGCAATGCATGTTTGACGTGTTTGGCGGGAAGTGGCTTATGCGGGT

GAAATAGTGCACGGAAAGACTAGTCCCATATCCCATGATAACTGCGGTATCTTTA

AGAATGTCCCCCAGGGTATTGCAGTTACAAGATATCATAGCTTGGCTGGCACTGA

AAGTAGTCTGCCTAGCTGCCTAAAGGTGACTGCCTCTACTGAAAACGGGATAATC

ATGGGGGTAAGGCACAAGAAGTACACCGTCGAGGGGGTGCAATTCCACCCAGAG

AGTATTTTAACCGAAGAAGGACATCTAATGATCCGTAATATTCTTAATGTTTCTG

GCGGAACGTGGGAGGAAAATAAATCAAGCCCATCCAATTCCATCCTAGATAGGA

TATACGCCAGGCGTAAAATTGACGTAAACGAACAGTCAAAGATTCCCGGTTTCA

CCTTTCAGGACTTACAATCTAACTATGATCTTGGCCTTGCCCCGCCTCTGCAAGAT

TTTTATACCGTGCTGAGCAGTAGTCATAAGAGGGCTGTGGTCCTAGCGGAGGTGA

AGCGTGCCTCCCCTAGCAAAGGTCCAATCTGCCTGAAGGCCGTTGCTGCTGAACA

AGCCCTTAAATATGCTGAGGCTGGGCGAGTGCAATTAGCGTTCTAACAGAACC

CCACTGGTTCCACGGGAGCCTTCAAGACCTTGTGAATGTAAGAAAGATCTTGGAT

CTAAAATTTCCGCCAAAAGAGAGACCCTGCGTGCTTAGGAAAGAGTTTATATTTT

CCAAATACCAAATATTGGAGGCACGTCTAGCTGGTGCAGATACTGTCCTTTTGAT

TGTAAAGATGTTGTCCCAACCATTACTGAAAGAGCTATATAGTTACTCAAAGGAT

TTAAACATGGAGCCGTTAGTGGAAGTAAATAGCAAGGAGGAGCTACAACGTGCC

CTGGAAATTGGTGCCAAGGTTGTTGGAGTTAACAATCGTGACTTGCATTCCTTCA

ACGTAGACTTGAATACAACAAGTAATTTGGTCGAATCTATCCCAAAAGATGTGCT

GTTGATTGCACTTTCCGGTATCACAACACGTGATGACGCCGAAAAGTATAAAAA

-continued

GGAGGGGGTGCACGGGTTTTTGGTGGGTGAGGCGTTAATGAAATCTACAGATGT

AAAGAAGTTTATTCATGAGCTGTGCGAATAA (*Saccharomyces cerevisiae* (TRP4 gene))
SEQ ID NO: 35

ATGAGCGAAGCTACTCTATTAAGTTATACCAAAAAGCTACTAGCAAGCCCACCTC

AGCTTAGTTCCACCGACCTACACGATGCACTACTTGTCATCCTAAGTCTACTTCA

GAAGTGCGACACCAATTCTGATGAGTCCTTGTCTATTTATACGAAGGTGTCTTCC

TTTTTAACAGCCCTAAGGGTGACTAAGTTAGATCATAAGGCGGAATATATTGCCG

AGGCTGCAAAAGCAGTTTTGCGTCACTCAGATCTGGTCGATCTACCTTTACCTAA

AAAGGATGAGCTGCATCCTGAAGATGGTCCTGTTATCTTGGACATTGTGGGTACT

GGGGGTGATGGACAGAATACCTTTAACGTGTCAACGTCAGCCGCTATTGTGGCCT

CAGGTATTCAGGGACTGAAGATTTGCAAACACGGAGGTAAAGCATCTACCTCAA

ACAGCGGAGCTGGAGATCTGATTGGGACATTGGGATGCGATATGTTCAAAGTGA

ATAGTAGCACAGTCCCCAAATTGTGGCCAGACAATACATTTATGTTCTTATTGGC

TCCATTCTTTCATCATGGGATGGGTCATGTAAGCAAGATTCGTAAGTTTCTTGGA

ATACCTACGGTATTTAACGTATTGGGGCCGCTGTTACACCCCGTATCCCATGTGA

ATAAGAGGATACTTGGAGTGTATTCAAAAGAGTTGGCGCCAGAATATGCGAAGG

CAGCAGCCTTGGTCTATCCAGGGTCAGAAACGTTTATTGTGTGGGGCCATGTTGG

GCTTGACGAGGTGAGCCCCATAGGAAAGACTACCGTGTGGCACATCGATCCGAC

AAGCTCAGAACTAAAGTTGAAGACCTTCCAGCTGGAGCCATCTATGTTCGGTCTG

GAGGAGCACGAGCTGAGTAAATGCGCCTCATATGGACCTAAGGAGAATGCTCGT

ATATTAAAGGAGGAAGTCCTTTCCGGCAAATACCACCTAGGCGACAATAATCCA

ATATATGATTACATTCTGATGAATACTGCAGTATTATACTGCCTGTCCCAAGGGC

ACCAAAACTGGAAGGAAGGTATTATCAAAGCCGAGGAGTCAATTCACAGCGGGA

ATGCCTTGAGATCGCTAGAACATTTCATTGATTCAGTATCTTCCCTTTAA (*Saccharomyces cerevisiae* (TAT2 gene))
SEQ ID NO: 36

ATGACCGAAGATTTCATCAGTAGCGTCAAAAGGTCAAATGAAGAGCTTAAAGAG

AGAAAATCTAATTTTGGGTTTGTAGAGTACAAGTCAAAACAACTTACCTCCAGTA

GCTCACACAACTCCAACTCTTCACACCATGATGACGACAACCAGCACGGTAAAA

GAAACATCTTTCAGCGTTGTGTGGATTCTTTTAAATCCCCTCTGGATGGGTCTTTC

GACACCTCCAATCTGAAAAGAACACTGAAACCTCGTCATTTAATAATGATCGCAA

TAGGAGGTAGTATAGGTACTGGTCTTTTCGTGGGTTCAGGGAAGGCTATAGCGGA

AGGCGGACCACTTGGCGTTGTGATCGGATGGGCCATTGCGGGTAGCCAAATAAT

AGGTACTATACATGGGTTAGGAGAGATCACGGTAAGATTTCCAGTAGTCGGTGC

GTTTGCCAACTACGGCACCCGTTTCTTGGACCCGAGCATTAGTTTTGTAGTCTCCA

CTATATACGTGCTACAGTGGTTCTTTGTCCTACCCCTAGAGATTATTGCTGCGGCG

ATGACCGTGCAATACTGGAACAGTTCTATCGATCCGGTAATATGGGTCGCAATTT

TCTATGCCGTCATCGTCTCAATCAATTTGTTTGGAGTTAGGGGTTTCGGAGAAGC

TGAATTCGCCTTCTCAACTATTAAGGCAATCACTGTCTGTGGCTTCATAATCTTAT

GTGTAGTCTTGATCTGCGGCGGAGGACCCGATCACGAATTCATTGGTGCTAAATA

CTGGCATGATCCTGGCTGCCTGGCAAACGGGTTTCCTGGAGTCTTGAGTGTCCTT

GTCGTTGCGTCATACAGCCTAGGAGGCATAGAAATGACTTGCTTAGCCTCTGGGG

```
AAACGGACCCAAAGGGACTTCCCTCAGCTATAAAACAGGTTTTCTGGCGTATTTT
GTTTTTCTTCTTAATTTCTTTAACTCTAGTGGGATTTTTAGTTCCTTACACCAACCA
AAATCTACTAGGTGGCTCCTCTGTCGATAATAGTCCCTTCGTTATCGCGATTAAG
CTACACCATATCAAAGCTCTTCCGTCTATTGTTAACGCAGTTATCCTTATTTCCGT
GCTATCCGTGGGTAACAGTTGCATCTTTGCCAGCTCCAGAACTCTGTGTAGCATG
GCACATCAAGGACTGATACCGTGGTGGTTCGGCTATATTGACAGAGCTGGCAGA
CCCCTGGTTGGGATTATGGCCAATTCTCTTTTCGGCTTATTGGCGTTCCTTGTTAA
ATCTGGCTCCATGAGTGAGGTGTTTAATTGGCTGATGGCTATAGCCGGACTGGCG
ACATGTATTGTGTGGTTATCTATAAATCTTTCCCATATAAGATTCCGTCTTGCAAT
GAAGGCCCAAGGAAAGTCCCTGGATGAACTTGAATTCGTAAGCGCGGTTGGTAT
ATGGGGATCTGCTTATTCCGCACTTATCAATTGCTTAATACTTATTGCTCAATTTT
ATTGCTCTTTATGGCCAATCGGGGGTTGGACATCCGGAAAAGAGAGGGCAAAGA
TTTTCTTTCAGAATTATCTTTGCGCCCTGATTATGTTATTTATATTCATCGTCCATA
AGATCTATTATAAATGTCAAACGGGAAAGTGGTGGGGTGTTAAAGCTCTGAAGG
ACATCGACCTAGAGACCGACAGGAAGGACATAGACATCGAAATAGTTAAACAAG
AAATCGCTGAAAAGAAGATGTATTTGGACTCCAGACCTTGGTACGTGAGGCAGT
TTCATTTTTGGTGCTAA
```

What is claimed is:

1. A recombinant host organism comprising:
a plurality of cells transfected by a gene expressed in the recombinant host organism;
wherein the recombinant host organism is a fungal species selected from the group consisting of *Schizosaccharomyces cerevisiae, Schizosaccharomyces japonicus, Schizosaccharomyces pombe, Schizosaccharomyces cryophilus, Saccharomyces cerevisiae, Kluyveromyces lactis, Kluyveromyces dobzhanskii*, and *Yarrowia lipolytica*;
wherein the gene is codon optimized for expression in the recombinant host organism and is selected from a group consisting of PsiD, PsiH, PsiK, and PsiM; wherein:
PsiD encodes an L-tryptophan decarboxylase and comprises nucleic acid sequence SEQ ID NO:1, SEQ ID NO:2, or SEQ ID NO:3;
PsiH encodes a tryptamine 4-monooxygenase and comprises nucleic acid sequence SEQ ID NO:4, SEQ ID NO:5, or SEQ ID NO:6;
PsiK encodes a 4-hydroxytryptamine kinase and comprises nucleic acid sequence SEQ ID NO:7 or SEQ ID NO:8; and
PsiM encodes a methyl transferase and comprises codon optimized nucleic acid sequences SEQ ID NO:9, SEQ ID NO:10, SEQ ID NO:11, SEQ ID NO:12, or SEQ ID NO:13.

2. The recombinant host organism of claim 1, comprising PsiD, PsiH, PsiK and PsiM, all codon optimized for expression in the recombinant host organism, wherein the organism synthesizes psilocybin.

3. The recombinant host organism of claim 2, wherein the organism synthesizes psilocybin via at least a first pathway and a second pathway in sequential order; wherein:
the first pathway is a shikimate-chorismate pathway; and
the second pathway is an L-tryptophan pathway.

4. The recombinant host organism of claim 3, wherein the synthesis of psilocybin via the first pathway and the second pathway increases titers of psilocybin in the plurality of cells over titers of psilocybin not synthesized via the first pathway and the second pathway.

5. The recombinant host organism of claim 3, wherein the shikimate-chorismate pathway is modified by overexpression of at least one of an ARO1 gene, an ARO2 gene, an ARO3 gene, an ARO4 gene, or an AROL gene, and the L-tryptophan pathway is modified by overexpression of at least one of a TRP1 gene, a TRP2 gene, a TRP3 gene, or a TRP4 gene.

6. The recombinant host organism of claim 5, wherein the first pathway is modified by expression of at least one of SEQ ID NO:27, SEQ ID NO 28, SEQ ID NO:29, SEQ ID NO:30, or SEQ ID NO:31 and the second pathway is modified by expression of at least one of SEQ ID NO:32, SEQ ID NO:33, SEQ ID NO:34, or SEQ ID NO:35.

7. The recombinant host organism of claim 3, synthesizing at least one psilocybin intermediates selected from the group consisting of tryptamine, 4-hydroxytryptamine, norbaeocystin, baeocystin, and psilocin.

8. The recombinant host organism of claim 7, wherein the synthesis of psilocybin via the first pathway and the second pathway increases a titer of a psilocybin intermediate in the plurality of cells over titers of the psilocybin intermediate not synthesized via the first pathway and the second pathway.

9. The recombinant host organism of claim 1, further comprising a recombinant transporter protein that is codon optimized for expression in the recombinant host organism.

10. The recombinant host organism of claim 9, wherein the recombinant transporter protein comprises SEQ ID NO:36.

11. The recombinant host organism of claim 1, growing in a medium comprising glucose, galactose, sucrose, fructose, molasses, or any combination thereof.

12. A method, the method comprising:
transfecting a plurality of cells in a recombinant host organism a set of genes comprising PsiD, PsiH, PsiK and PsiM, creating the recombinant host organism of claim 2; and
synthesizing psilocybin in the recombinant host organism.

* * * * *

SEQUENCE LISTING

<160> NUMBER OF SEQ ID NOS: 36

<210> SEQ ID NO 1
<211> LENGTH: 1320
<212> TYPE: DNA
<213> ORGANISM: Psilocybe cubensis
<220> FEATURE:
<223> OTHER INFORMATION: PSID gene

<400> SEQUENCE: 1

```
atgcaagtca tccccgcgtg caacagcgca gctataaggt cactttgtcc gacccccgag    60
agctttagaa atatgggctg ctttccgtg agcgatgccg tctatagcga atttataggt    120
gaacttgcga cgagagcatc taatagaaac tacagcaatg agttcggttt aatgcaacca    180
atacaagaat ttaaagcgtt catcgagagt gatcccgttg tacaccaaga gtttatcgac    240
atgtttgaag gcatccaaga ttctccgagg aactaccaag aactatgtaa catgttcaat    300
gatattttta ggaaggctcc cgtatacgga gatttgggcc ctccggtcta catgattatg    360
gcgaagttga tgaatacaag ggcgggtttc agtgcgttca aagacaacg tctgaacctg    420
cattttaaaa agctgttcga tacctggggt ttatttcttt catccaaaga cagcaggaat    480
gtcctggtag ctgaccagtt tgatgatagg cactgcggct ggctgaacga gagggcatta    540
tctgcgatgg tgaaacacta taatgggcgt gcatttgatg aagtatttct atgtgacaaa    600
aatgcaccct attcggctt taattcatac gacgatttct tcaataggag gttccgtaat    660
agagacattg atagaccgt tgtcggcggc gtgaacaaca cgacgcttat atcagcagcc    720
tgtgagtctc tgtcttataa cgtcagctat gacgtgcaat ccttagatac tttagttttc    780
aaaggtgaga cgtactcatt aaaacatctt ttgaataatg atccatttac gccacaattc    840
gagcacggtt ccatattgca aggattccta aacgtgacag catatcatcg ttggcacgcg    900
```

-continued

```
ccggttaacg gaactatcgt caagataatc aacgttcctg gtacttattt cgcacaagcg      960
ccgtctacca tcggtgatcc gatcccagat aatgactatg atccaccgcc atatctaaag    1020
agtcttgtgt acttcagtaa cattgcagcg agacagatta tgttcataga agctgataac    1080
aaggagatag gcctaatttt cctggttttt ataggcatga cagaaatttc aacgtgtgaa    1140
gcaacggtat ccgaggggca acatgtcaat agagggacg  acctgggtat gtttcatttc    1200
gggggctctt cttttgccct tggcctgcgt aaagactgcc gtgccgaaat tgttgagaag    1260
ttcacggagc ccgggacagt tataaggatt aacgaagtcg tcgccgcctt gaaggcttaa    1320
```

<210> SEQ ID NO 2
<211> LENGTH: 1320
<212> TYPE: DNA
<213> ORGANISM: Psilocybe cyanescens

<400> SEQUENCE: 2

```
atgcaagtgc ttcctgcttg ccaaagctct gcccttaaaa ccctgtgtcc gagccccgag      60
gcttttagaa agctgggatg gctacctacg tctgacgaag tgtacaacga gttcatagat     120
gatctgactg gcaggacttg caatgagaag tatagcagcc aagtaaccct gttaaagcca     180
atccaagact tcaagacttt catagagaat gacccgatag tatatcaaga gttcattagc     240
atgtttgagg catagaacagagcc ctact aactatcatg agctatgtaa catgttcaac    300
gatatttttc gtaaggcacc cctatacgga gacttaggac cacctgtcta catgataatg    360
gcacgtatta tgaatacgca ggcgggtttt tcagcgttca ccaaagaatc tctgaacttc    420
cattttaaga agctattcga cacgtggggt ctattcctaa gctctaaaaa ttccagaaac    480
gtacttgtcg ccgatcagtt tgacgacaaa cattacggat ggttttctga gagcaaag     540
actgcgatga tgatcaacta ccaggacgt  acattcgaga aggtcttcat ctgtgacgag    600
catgtgcctt atcacggatt tacttcctat gacgacttct ttaacaggag atttcgtgac    660
aaggatacag accgtcccgt cgtcggtggc gtcaccgaca cgacgttgat aggcgcggca    720
tgtgaaagtt tatcttataa cgtttctcac aacgtccaat cactggacac ccttgtcata    780
aaaggcgagg cgtactcttt aaaacaccct ctgcataatg acccatttac gccacagttt    840
gaacatggat ctatcatcca aggattcttg aacgttacag cctatcacag atggcactct    900
ccagttaacg gcactattgt gaagattgta acgtaccag  gcatacttt  tgcccaggcg    960
ccctatacca taggtagccc aatccctgat aatgaccggg accgccgcc  ctacttgaag   1020
agccttgttt attttagcaa cattgctgcc agacagatta tgtttattga ggctgacaat   1080
aaagatattg gccttatctt tcttgtgttc attggcatga ctgaaattag cacatgtgaa   1140
gcgacggtat gcgaaggaca gcacgttaac agaggcgatg accttgggat gtttcatttt   1200
gggggatcga gttttgcatt ggggcttaga aaagatagca agcaaaaat  actagaaaaa   1260
tttgcaaagc cgggaacagt aataaggatt aacgagctgg tggcatccgt cagaaaataa   1320
```

<210> SEQ ID NO 3
<211> LENGTH: 1272
<212> TYPE: DNA
<213> ORGANISM: Gymnopilus junonius

<400> SEQUENCE: 3

```
atgtcatctc ctcgtatcgt gctgcacagg gttggtggct ggctgcctaa agaccaaaac      60
gtgctagaag catggctgag caagaagatt gctaaagcaa aaactagaaa tagggctcca     120
```

| | |
|---|---|
| aaagatttggg ctcctgtgat tcaagacttc cagagactga tagagaccga tgccgagatc | 180 |
| tacatgggtt tccatcagat gttcgagcag gtccccaaga aaactccgta cgataaagac | 240 |
| cccaccaatg agcaatggca agtaagaaat tatatgcaca tgttagatct gttcgaccta | 300 |
| attataaccg aggcaccgga tttcgaacaa aatgatcttg ttggatttcc aataaatgca | 360 |
| atcctggatt ggcccatggg accccccggt gggcttactg catttattaa ccctaaagta | 420 |
| aatattatgt ttcataaaat gtttgacgtt tgggcagtat ttctgtcatc tccagcatca | 480 |
| tgctacgtcc taaatacaag cgatagcggt tggttcggtc ccgctgcaac cgcagctata | 540 |
| cccaacttca aagagacctt catctgcgac ccaagtctgc catacctagg gtacactagc | 600 |
| tgggataatt tcttcaccag gctgtttagg ccgggggtgc gtcctgtcga gttcccgaac | 660 |
| aatgatgcca ttgttaacag tgcgtgtgaa tccacggttt ataatatagc tccaaacatt | 720 |
| aaaccactag ataaattttg gattaaggga gagccgtatt ccctaaatca catacttaat | 780 |
| aacgacccgt acgcgagcca gttcgtaggt ggaaccatat cccaagcatt cttatctgcg | 840 |
| ctgaactatc accgttgggc gagtccggtt aacggcaaca ttgtcaaggt cgtcaatgtt | 900 |
| ccgggtacat actacgcgga gtccccagtt accggttttg ggaatccaga agggccagat | 960 |
| ccagcggcgc ccaatctatc tcaaggtttc attactgctg tggctgcgag agccctgatt | 1020 |
| ttcatagagg ccgataaccc taacatcgga ttaatgtgtt ttgtgggggt tggcatggca | 1080 |
| gaggtctcaa catgtgaagt taccgtgagt gtaggcgatg ttgtcaagaa aggagatgag | 1140 |
| attggaatgt tccatttcgg gggaagcact cactgcttga tatttaggcc acaaacaaaa | 1200 |
| attacgttca atcccgacta tcctgtgtca accgccgtac ccttgaatgc tgcagtggca | 1260 |
| accgtcgtat aa | 1272 |

<210> SEQ ID NO 4
<211> LENGTH: 1527
<212> TYPE: DNA
<213> ORGANISM: Psilocybe cubensis

<400> SEQUENCE: 4

| | |
|---|---|
| atgattgccg tcttattctc ttttgtcata gctggctgca tctattatat agtatcccgt | 60 |
| cgtgtgcgtc gttcaagact tccgcccgga ccaccaggca tccctatccc ctttatcggc | 120 |
| aatatgtttg acatgcccga agaatcaccc tggttgacgt ttctgcaatg gggcagagat | 180 |
| tataatacag acattttgta tgtagatgca ggcggaactg agatggtaat attgaatacc | 240 |
| cttgagacaa tcactgattt gttagaaaag aggggggtcta tatattctgg caggctagaa | 300 |
| agtaccatgg ttaatgagtt gatggggtgg gagtttgatc taggattcat cacctacggt | 360 |
| gatcgttgga gagaggagag aaggatgttc gcgaaagagt tcagcgaaaa gggaatcaaa | 420 |
| caattcaggc acgcccaagt aaaggcggcg catcaacttg tccaacagct gacaaaaaca | 480 |
| ccggatcgtt gggctcaaca catacgtcat cagatagccg ccatgtcttt agacatcggc | 540 |
| tatggcatag acttagcgga ggatgatcca tggttagaag caacacactt agctaacgaa | 600 |
| ggactggcga tagcttccgt cccaggaaaa ttttgggtag actcatttcc gtctctgaaa | 660 |
| tacctaccag cctggtttcc tggagctgtc ttcaaacgta aggcaaaagt atggagggag | 720 |
| gcagcagacc atatggtgga catgccatat gagactatga ggaaattggc gccacagggc | 780 |
| ttgactagac catcctatgc atctgcaaga ctacaggcca tggacctaaa cggtgatttg | 840 |
| gagcaccaag agcacgtaat taaaaacaca gcagccgaag tgaacgtcgg aggggggagat | 900 |
| acaaccgtct ctgcgatgag tgcgttcata ctagcgatgg tcaagtatcc ggaagtacag | 960 |

```
cgtaaagtcc aggccgagct agacgcactt actaacaacg gccagattcc cgattacgac    1020
gaggaagacg atagtctacc ttacttgacc gcatgtatta aagagttatt tagatggaat    1080
caaattgcgc ccctagcgat tcctcacaag ttaatgaaag acgatgtata tagggttat     1140 ctaataccta agaatacgct agttttgca aacacatggg cggtcctgaa cgaccctgaa     1200
gtctacccag accctagcgt atttaggccg gagcgttatt taggacccga cggtaagccc    1260
gataatactg tcagggaccc caggaaggct gcgttcgggt atgggaggag gaactgtcca    1320
ggaatacact tagcccaatc aaccgtctgg atagccggag cgaccttact tagtgcgttt    1380
aatatcgaga ggccagttga ccagaatggg aaacccatcg atattccagc agacttcaca    1440
accgggtttt tcaggcatcc tgttcctttt cagtgccgtt tcgtgcctag gactgaacag    1500
gtctcccaat cagtcagtgg gccgtaa                                        1527

<210> SEQ ID NO 5
<211> LENGTH: 1485
<212> TYPE: DNA
<213> ORGANISM: Psilocybe cyanescens

<400> SEQUENCE: 5
atggcgcctt tgacaaccat gattccgatc gttctatctc ttctaatagc ggggtgtata     60
tattatatca acgcaaggag aattaaaagg tccaggttgc caccaggacc gccgggtatt    120
cctattccat tcatcgggaa catgttcgac atgccaagcg aaagtccctg gctaatcttc    180
ctacaatggg gacaagagta ccagaccgat ataatttacg ttgacgcggg aggaactgat    240
atgataatac ttaattccct agaggcaatt acagatctgt tagagaaaag gggctcattg    300
tatagcggga ggttggaatc cacgatggta aacgagctaa tgggttggga gtttgatttc    360
ggtttcatac cttacggtga agatggaggg gaagaacgtc gtatgttcgc caaagagttt    420
tctgagaaga acataaggca gtttagacac gcccaagtaa aggctgccaa tcagctagtg    480
cgtcaactaa ccgataaacc ggacaggtgg tcacaccaca taaggcatca aatcgcgtcc    540
atggccctgg acatcggtta cggaatcgat cttgctgaag acgatccgtg gatcgcagct    600
tccgaactgg cgaatgaagg cttggctgta gcctcagtgc caggatcttt ttgggtagat    660
acgttcccgt tcttaaaata tttgccaagt tggttacctg gcgcggagtt caaaagaaac    720
gcaaagatgt ggaaggaagg agcagatcat atggtcaata tgccttacga aacgatgaaa    780
aagctaagcg cacaaggact gactagacca tcatatgcaa gtgcgaggct acaggctatg    840
gacccgaacg gggatcttga acatcaagaa agagtgatca aaaatacggc cacgcaggta    900
aatgttggtg gtggggatac tacagtcggg gcagtaagtg cgtttatcct tgcgatggta    960
aaatacccgg aagttcaaag gaaagtacaa gccgagctgg acgagttcac gagcaagggg   1020
aggataccgg attacgatga agataacgat tctcttccct atctatcggc ttgcttcaaa   1080
gagctgttca ggtggggcca gattgcgcct ttggcgattg ctcataggct gataaaggac   1140
gatgtctata gggaatatac tatcccaaag aatgctctgg tctttgcgaa caattggtat   1200
gggcgtactg tattgaatga cccttctgag tatcccaatc cttcagaatt tagacctgaa   1260
aggtacttgg ggcccgatgg taagccagat gacaccgtca gggacccaag aaaggcagcg   1320
tttgggtacg gacgtagagt gtgtccaggg atacacctgg cgcagagcac ggtctggatt   1380
gctggtgtcg cgttggtatc tgccttcaac attgagctgc ccgtggacaa agacgggaaa   1440
tgtatagata ttccggcggc cttcacgacg ggattcttta gataa                   1485
```

<210> SEQ ID NO 6
<211> LENGTH: 1572
<212> TYPE: DNA
<213> ORGANISM: Gymnopilus junonius

<400> SEQUENCE: 6

| | | | | | | |
|---|---|---|---|---|---|---|
| atgatgtccg | agatgaatgg | gatggataaa | ttggcgctat | tgacgacgtt | attagctgcc | 60 |
| ggttttctat | acttcaagaa | taagcgtcgt | tccgcgttgc | cgttcccgcc | agggccgaaa | 120 |
| aagcatcccc | ttttaggtaa | cttgctggac | cttccgaaga | agctggagtg | ggagacgtac | 180 |
| agaagatggg | gaaaagaata | caattcagat | gtaatacatg | ttagcgcggg | gagtgtaaac | 240 |
| ttaattatcg | ttaattcctt | tgaagctgcg | acagacctgt | ttgataagag | atcagccaat | 300 |
| tattcaagta | ggccacaatt | cacgatggtg | agagaactga | tgggatggaa | ttggttgatg | 360 |
| tctgcattaa | tatacggtga | caagtggaga | gagcaacgta | ggttgtttca | gaaacatttc | 420 |
| agtacaacga | atgccgaact | ttaccaaaat | acacaattag | aatatgttcg | taaagccctg | 480 |
| cagcatctgc | tagaagagcc | ttcagatttt | atgggaataa | cacgtcacat | ggctgggggc | 540 |
| gtcagcatgt | ccctggcata | tggcttaaac | attcagaaga | aaacgaccc | ttttgttgac | 600 |
| cttgcacaaa | gggcagtgca | cagcataaca | gaggcctcag | ttcctgggac | attttgggta | 660 |
| gacgtaatgc | cttggctaaa | gtatattcca | gaatgggtgc | cgggtgctgg | ctttcagaag | 720 |
| aaggctgagt | gtggaggaa | attacagcaa | gattttcgtc | aggtcccata | tcaggcagct | 780 |
| ctgaaagaca | tggcttcagg | gaaagctaaa | ccatcatttg | caagtgagtg | tttggagacg | 840 |
| atagacgaca | tgaggatgc | acaaaggcaa | agggaggta | taaagacac | agctgccatt | 900 |
| gtattcgcag | ccggtgcgga | tacaagcctt | agtggaatcc | atacattatt | cgccgcaatg | 960 |
| ttgtgttacc | cagaggtcca | gaagaaagca | caagaagaac | tggatcgtgt | cttgggtggg | 1020 |
| agacgtctac | cggaatttac | cgatgagccc | aacatgccct | acatctctgc | gttagtgaag | 1080 |
| gaaatattga | ggtggaaacc | ggctactccg | attggcgtac | cccacttagc | cagcgaggat | 1140 |
| gacgtttaca | acggatatta | cataccaaaa | cgtgcggttg | tcataggcaa | cagctgggct | 1200 |
| atgcttcatg | atgaggaaac | ttatccggac | ccaagcacct | taaccctga | cagatttttg | 1260 |
| accacaaata | aaagcactgg | aaaattggaa | ttagatccca | cagtgagaga | tcccgcttta | 1320 |
| atggccttcg | gatttggtag | acgtatgtgt | ccaggacgtg | atgtagctct | ttctgtcata | 1380 |
| tggctgacta | tcgcaagcgt | tttagcaacg | tttaatatta | ccaaggcgat | agacgaaaac | 1440 |
| gggaaggaac | tggaaccgga | tgtacagtac | tggagcggtc | taatcgtcca | cccgctgcca | 1500 |
| ttcaaatgta | cgatcaagcc | aagatcaaag | gcagcggaag | aacttgtgaa | atctggcgca | 1560 |
| gacgcctatt | aa | | | | | 1572 |

<210> SEQ ID NO 7
<211> LENGTH: 1089
<212> TYPE: DNA
<213> ORGANISM: Psilocybe cubensis

<400> SEQUENCE: 7

| | | | | | | |
|---|---|---|---|---|---|---|
| atggcattcg | acttgaaaac | tgaagacggg | ctaataactt | acctaacgaa | acacctttct | 60 |
| ttggatgtgg | atacatcagg | tgtgaaaagg | ttaagcggtg | gcttcgttaa | cgtgacctgg | 120 |
| agaataaaac | taaacgcacc | ctatcagggt | cacacatcaa | taattctaaa | gcacgcacag | 180 |
| ccgcatatgt | caaccgacga | agacttcaaa | attggcgtgg | agcgttccgt | ctatgagtac | 240 |
| caggctatca | aacttatgat | ggccaatagg | gaggtgctag | ggggtgttga | cgggatcgtg | 300 |

-continued

```
tctgtgccag aggggttgaa ctacgacctt gaaaataatg cattgatcat gcaggacgta    360
ggtaagatga agaccctatt agactacgta acggcaaaac ccccgcttgc gactgatata    420
gcacgtttgg taggtacaga gattgggggt tcgtggcta gactgcataa cataggagg      480
gagaggagag acgacccgga gttcaagttt ttctctggaa atatagtcgg caggacaaca    540
agcgatcaac tataccaaac aattatccct aacgcagcta agtacggggt agatgaccct    600
ctactgccta ccgttgtaaa agatctggtc gatgatgtca tgcacagtga ggagactctt    660
gtaatggcgg atttatggag cggcaatata cttctacagt tggaggaggg gaatccttca    720
aagttacaga aaatctacat tttagattgg gaattgtgta aatacggccc agcttcacta    780
gaccttgggt atttcttggg tgattgctac ctgatttctc gtttccaaga tgagcaggtc    840
ggcacaacta tgagacaagc ctacttacaa agctacgctc gtacctctaa acattccata    900
aactacgcca aggtcactgc gggaattgca gcacatatag tgatgtggac agactttatg    960
cagtgggggga gtgaggaaga gagaattaac ttcgtcaaga aaggcgtggc cgccttccat   1020
gacgcaagag ggaacaatga taatggtgaa atcacctcta ctctgttgaa ggagagttca   1080
actgcctaa                                                            1089
```

<210> SEQ ID NO 8
<211> LENGTH: 1086
<212> TYPE: DNA
<213> ORGANISM: Psilocybe cyanescens

<400> SEQUENCE: 8

```
atgactttcg atctaaaaac ggaggagggc ttattatctt atcttaccaa gcatttaagt     60
ttagacgtag caccgaatgg tgtcaaaaga ttatctggtg gattcgtcaa tgtgacttgg    120
agggtagggt taaatgcacc gtaccatggg cacacgtcta taatccttaa acacgctcaa    180
ccacatttaa gctccgatat tgacttcaaa atagggtggg aaagaagtgc gtatgagtac    240
caggctttga agattgtctc tgccaacagc agcctacttg gttcttctga tatccgtgtc    300
tcagttccag aaggtttgca ctatgatgtt gtgaataacg ccctaatcat gcaggacgtg    360
ggtacaatga agaccttgct ggactatgtt acagcgaaac cccctatatc tgctgaaatt    420
gccagcctag taggtagtca gattggcgct ttcatagcaa gattacacaa tttgggcaga    480
gaaaataaag ataaggacga ctttaaattt ttctccggaa atatagttgg gaggacgacg    540
gcagaccaac tgtatcagac cataattcct aatgcggcaa aatatggaat cgatgaccca    600
attcttccaa tagttgtcaa agaacttgtt gaagaagtca tgaactcaga ggaaaccctg    660
attatggcgg acctatggag cggtaatatc ttgctacagt tcgacgagaa cagtacggaa    720
ctaacccgta tttggctggt agactggag ctatgcaagt acgggccgcc gtcactggat    780
atgggttact tcttgggcga ctgcttttttg gtagctagat tccaagacca acttgtaggc    840
acatctatga gacaagcata ccttaaaagc tacgcacgta acgtaaaaga gccgatcaac    900
tatgctaagg ccacagcagg catcggcgct catttggtaa tgtggactga cttcatgaag    960
tgggggtaacg atgaagaaag ggaggagttc gtgaaaaagg gggtcgaagc attccacgag   1020
gccaacgaag acaataggaa cggagagata acgagcatat tggtgaaaga ggcatcacgt   1080
acgtaa                                                              1086
```

<210> SEQ ID NO 9
<211> LENGTH: 930
<212> TYPE: DNA

<213> ORGANISM: Psilocybe cubensis

<400> SEQUENCE: 9

| | | | | | |
|---|---|---|---|---|---|
| atgcacatca | gaaacccta | tagaacccc | atagattacc | aggcgctgag | tgaggccttt | 60 |
| ccaccattga | agccctttgt | atccgtaaac | gctgatggta | cgagttccgt | agatctaacg | 120 |
| atcccggagg | cgcaacgtgc | gttcactgcc | gcattgttac | atagagattt | cgggctaacc | 180 |
| atgactatac | cggaagatag | actgcccct | actgtcccta | acaggttaaa | ttatgtactg | 240 |
| tggattgaag | atattttcaa | ctacacgaat | aagaccctgg | ggctgagcga | tgacagaccg | 300 |
| ataaaggggg | tggatattgg | cacaggcgcc | agcgcaatat | accctatgct | tgcttgcgcc | 360 |
| aggtttaagg | catggtccat | ggtagggaca | gaggtagaac | gtaaatgtat | tgatacggct | 420 |
| agactaaatg | tcgtcgccaa | taatctacag | gatagattga | gtatattaga | gacatccatc | 480 |
| gacggtccca | ttcttgttcc | aatcttcgag | gccacagaag | aatatgagta | tgagttcacc | 540 |
| atgtgtaatc | cgccattcta | cgatggtgcg | gccgacatgc | agacctctga | cgcggccaaa | 600 |
| ggattcggct | ttggagtggg | ggcccctcac | tctggaacag | ttatcgaaat | gtccactgaa | 660 |
| ggaggggagt | ccgcattcgt | agcccagatg | gtgagagaga | gcttgaaact | gcgtaccaga | 720 |
| tgcagatggt | atacgtctaa | tcttgggaaa | ttaaaaagcc | taaaggagat | tgtgggtctt | 780 |
| ttaaaagagc | tggagatttc | caactacgcc | ataaacgagt | acgtccaagg | gtctaccaga | 840 |
| agatacgccg | tcgcgtggtc | ttttactgac | attcagcttc | cagaggagct | atctcgtccc | 900 |
| agtaacccgg | aattgtcctc | cttgttttaa | | | | 930 |

<210> SEQ ID NO 10
<211> LENGTH: 930
<212> TYPE: DNA
<213> ORGANISM: Psilocybe cyanescens

<400> SEQUENCE: 10

| | | | | | |
|---|---|---|---|---|---|
| atgcatatca | ggaatccgta | ccgtgacggc | gtggactacc | aggcattagc | cgaggctttc | 60 |
| ccggcgctaa | agccacacgt | cactgtcaat | tcagacaata | caacttctat | agatttcgcg | 120 |
| gtacccgagg | cccagagact | ttacaccgca | gcattacttc | atagggactt | tggtttaacc | 180 |
| ataaccttac | ccgaggatag | actatgtcct | acggtcccga | atagattgaa | ctatgtgttg | 240 |
| tgggtggaag | atatactgaa | ggttacgtca | gacgcattgg | gattaccgga | taatagacaa | 300 |
| gtgaaaggta | ttgatattgg | aacaggagca | agcgcaattt | atcccatgtt | agcttgttcc | 360 |
| aggtttaaga | cttggtccat | ggtagctaca | gaggtggatc | aaaaatgcat | agataccgca | 420 |
| aggctaaacg | taatagctaa | taaccttcag | gagagattgg | caatcatagc | cacttccgtg | 480 |
| gacgggccta | ttcttgttcc | tctgttgcag | gctaattccg | actttgaata | tgacttcacc | 540 |
| atgtgcaatc | cgcccttta | cgacggcgcc | tctgatatgc | agacaagtga | tgccgctaaa | 600 |
| ggctttggct | tcggagtaaa | cgcacctcac | actgggacag | tacttgaaat | ggcgacagaa | 660 |
| ggaggggaaa | gtgcgttcgt | tgcccaaatg | gttcgtgagt | ccttgaacct | gcagactaga | 720 |
| tgcaggtggt | tcacatctaa | tttgggtaaa | ctaaaatcac | tgtacgagat | tgtgggtcta | 780 |
| ttaagagaac | accagatttc | taactacgcc | ataaatgagt | atgtacaagg | cgcaactcgt | 840 |
| aggtatgcaa | ttgcgtggag | tttcatagat | gtaagactgc | ccgaccattt | gtccagacca | 900 |
| tctaatcccg | atctatccag | tttgttttaa | | | | 930 |

<210> SEQ ID NO 11
<211> LENGTH: 954

```
<212> TYPE: DNA
<213> ORGANISM: Panaeolus cyanescens

<400> SEQUENCE: 11
atgcataacc gtaacccgta tagggacgtg attgattacc aagcacttgc ggaagcctac    60
ccgcccctaa aacccacgt cacggtgaac gcggataaca cggcatccat agatcttacg   120
atccccgagg tccagaggca atacacagca gctcttttac atcgtgattt cggattaact   180
atcacactac cagaagatag gctgtgcccg acagtaccga accgttttaaa ctatgtattg   240
tggatagagg atatatttca gtgtacgaat aaggctctgg gattgtcaga tgacagaccc   300
gttaagggg tagatatagg gaccggcgcc tccgccatct atccaatgct tgcttgcgcg   360
aggtttaagc agtggtccat gattgccaca gaagtggagc gtaagtgcat agatacagcg   420
agattgaatg tcctggcgaa taacttacag gaccgtttgt caattcttga ggtttcagta   480
gacggcccga ttttggtacc catctttgat accttcgagc gtgcgacaag cgattacgaa   540
tttgagttca cgatgtgtaa ccctccattt tacgacgggg ccgcggatat gcaaacatca   600
gatgcagcta agggtttcgg ttttggagtt aacgctccac actccggtac cgtgatagag   660
atggctactg aaggaggtga ggctgctttt gtggcgcaaa tggtccgtga gagcatgaag   720
ttacagacaa ggtgtcgttg gtttacaagc aacttaggca agctaaaatc actgcatgaa   780
attgttgctt tgttgagaga tcccagatc acaaactatg ccataaatga gtacgttcag   840
gggacgacga gaaggtacgc tcttgcttgg tccttcacag acataaaact tactgaggaa   900
ctttacaggc cctccaatcc agaattagga cctctttgca gcacatttgt ctaa          954

<210> SEQ ID NO 12
<211> LENGTH: 930
<212> TYPE: DNA
<213> ORGANISM: Gymnopilus dilepis

<400> SEQUENCE: 12
atgcacatta gaaacccta cttaacacct ccggactacg aggcccttgc ggaggccttc    60
cccgcactaa agccttatgt tacagttaac cccgataaga ctactacaat tgactttgcc   120
ataccggagg ctcagagatt atacacggct gctctacttt acagggactt tggactgaca   180
ataacattgc cgccggatag gttatgccca accgtgccca ataggcttaa ttatgttttg   240
tggattcagg acattctgca gattacctcc gctgccttgg gcttgccaga ggctagacaa   300
gtaaagggag tagacatagg taccggagcg gcagcgatat accctattct tggttgcagc   360
cttgcaaaga attggtctat ggtggggaca gaggtcgaac aaaaatgtat cgacatagcg   420
cgtcaaaacg tgatttcaaa tggattgcag gataggataa ccataactgc taataccata   480
gacgctccca ttctgctgcc cttatttgaa ggagacagta acttcgaatg ggagttcacc   540
atgtgtaacc cgccattta cgacggcgct gcggacatgg agacaagcca ggacgctaaa   600
ggcttcgggt tcggcgtcaa cgccccgcat acaggaacag tggtgaaat ggccacggac   660
ggtggtgagg ctgcattcgt cagccaaatg gtgagagagt ccttgcacct aaagacacgt   720
tgtagatggt tcacgtccaa tctaggtaaa ttgaagagtc tacatgaaat tgtgggattg   780
ttgcgtgaac accaaattac caactacgcg ataaatgaat atgttcaggg aacgacacgt   840
agatacgcga ttgcatggtc atttactgac ctacgtctat cagaccacct gccacgtcct   900
ccgaaccccg atctatcagc cctattttaa                                    930

<210> SEQ ID NO 13
```

<211> LENGTH: 894
<212> TYPE: DNA
<213> ORGANISM: Gymnopilus junonius

<400> SEQUENCE: 13

```
atgcactctc gtaacccttat agatcccct cctgatttcg cggcattaag tgcggcttat      60
cctccgctgt caccatacat aactaccgat ctaagcagcg gtcgtaaaac aattgacttt     120
agaaatgagg aagcgcaacg tcgtctaact gaggctatca tgttgcgtga cttcggcgtt     180
gtgttaaaca taccatctaa caggctgtgc ccgcctgtgc cgaatcgtat gaactatgta     240
ctttggatac aagatatagt ttacgcgcac cagacaatac tgggagtgag ttctcgtcgt     300
atcagaggtc ttgatattgg tactggtgct accgctatat atcctatact ggcatgcaag     360
aaagagcaga gctgggagat ggttgcaact gaattggacg actactccta tgagtgtgca     420
tgtgataacg tgtcatccaa caatatgcag acttccatta aagtaaagaa ggcttcggta     480
gatgggccca tcctgttccc agtggaaaac caaaatttcg actttagcat gtgcaacccg     540
cctttctacg gctctaagga ggaggtggcg caatccgcag agtcaaaaga actgccgccc     600
aatgctgttt gcacgggtgc agagatcgag atgatattta gtcaaggagg agaagagggt     660
ttcgtaggta gaatggtaga ggaatcagag aggttgcaaa cgagatgcaa atggtacact     720
tcaatgcttg gtaagatgtc tagtgtaagc actatagttc aggctctgcg tgcgagatca     780
attatgaatt atgctttgac agaatttgta caaggacaaa cccgtaggtg ggcgatagct     840
tggtctttct ccgacactca cttaccggat gccgtcagta gaatctctag ttaa          894
```

<210> SEQ ID NO 14
<211> LENGTH: 439
<212> TYPE: PRT
<213> ORGANISM: Psilocybe cubensis

<400> SEQUENCE: 14

```
Met Gln Val Ile Pro Ala Cys Asn Ser Ala Ala Ile Arg Ser Leu Cys
1               5                   10                  15

Pro Thr Pro Glu Ser Phe Arg Asn Met Gly Trp Leu Ser Val Ser Asp
            20                  25                  30

Ala Val Tyr Ser Glu Phe Ile Gly Glu Leu Ala Thr Arg Ala Ser Asn
        35                  40                  45

Arg Asn Tyr Ser Asn Glu Phe Gly Leu Met Gln Pro Ile Gln Glu Phe
    50                  55                  60

Lys Ala Phe Ile Glu Ser Asp Pro Val His Gln Glu Phe Ile Asp
65                  70                  75                  80

Met Phe Glu Gly Ile Gln Asp Ser Pro Arg Asn Tyr Gln Glu Leu Cys
                85                  90                  95

Asn Met Phe Asn Asp Ile Phe Arg Lys Ala Pro Val Tyr Gly Asp Leu
            100                 105                 110

Gly Pro Pro Val Tyr Met Ile Met Ala Lys Leu Met Asn Thr Arg Ala
        115                 120                 125

Gly Phe Ser Ala Phe Thr Arg Gln Arg Leu Asn Leu His Phe Lys Lys
    130                 135                 140

Leu Phe Asp Thr Trp Gly Leu Phe Leu Ser Ser Lys Asp Ser Arg Asn
145                 150                 155                 160

Val Leu Val Ala Asp Gln Phe Asp Asp Arg His Cys Gly Trp Leu Asn
                165                 170                 175

Glu Arg Ala Leu Ser Ala Met Val Lys His Tyr Asn Gly Arg Ala Phe
            180                 185                 190
```

```
Asp Glu Val Phe Leu Cys Asp Lys Asn Ala Pro Tyr Tyr Gly Phe Asn
            195                 200                 205

Ser Tyr Asp Asp Phe Phe Asn Arg Arg Phe Arg Asn Arg Asp Ile Asp
    210                 215                 220

Arg Pro Val Val Gly Gly Val Asn Asn Thr Thr Leu Ile Ser Ala Ala
225                 230                 235                 240

Cys Glu Ser Leu Ser Tyr Asn Val Ser Tyr Asp Val Gln Ser Leu Asp
                245                 250                 255

Thr Leu Val Phe Lys Gly Glu Thr Tyr Ser Leu Lys His Leu Leu Asn
            260                 265                 270

Asn Asp Pro Phe Thr Pro Gln Phe Glu His Gly Ser Ile Leu Gln Gly
            275                 280                 285

Phe Leu Asn Val Thr Ala Tyr His Arg Trp His Ala Pro Val Asn Gly
            290                 295                 300

Thr Ile Val Lys Ile Ile Asn Val Pro Gly Thr Tyr Phe Ala Gln Ala
305                 310                 315                 320

Pro Ser Thr Ile Gly Asp Pro Ile Pro Asp Asn Asp Tyr Asp Pro Pro
                325                 330                 335

Pro Tyr Leu Lys Ser Leu Val Tyr Phe Ser Asn Ile Ala Ala Arg Gln
            340                 345                 350

Ile Met Phe Ile Glu Ala Asp Asn Lys Glu Ile Gly Leu Ile Phe Leu
            355                 360                 365

Val Phe Ile Gly Met Thr Glu Ile Ser Thr Cys Glu Ala Thr Val Ser
        370                 375                 380

Glu Gly Gln His Val Asn Arg Gly Asp Asp Leu Gly Met Phe His Phe
385                 390                 395                 400

Gly Gly Ser Ser Phe Ala Leu Gly Leu Arg Lys Asp Cys Arg Ala Glu
                405                 410                 415

Ile Val Glu Lys Phe Thr Glu Pro Gly Thr Val Ile Arg Ile Asn Glu
            420                 425                 430

Val Val Ala Ala Leu Lys Ala
            435

<210> SEQ ID NO 15
<211> LENGTH: 439
<212> TYPE: PRT
<213> ORGANISM: Psilocybe cyanescens

<400> SEQUENCE: 15

Met Gln Val Leu Pro Ala Cys Gln Ser Ser Ala Leu Lys Thr Leu Cys
1               5                   10                  15

Pro Ser Pro Glu Ala Phe Arg Lys Leu Gly Trp Leu Pro Thr Ser Asp
            20                  25                  30

Glu Val Tyr Asn Glu Phe Ile Asp Asp Leu Thr Gly Arg Thr Cys Asn
        35                  40                  45

Glu Lys Tyr Ser Ser Gln Val Thr Leu Leu Lys Pro Ile Gln Asp Phe
    50                  55                  60

Lys Thr Phe Ile Glu Asn Asp Pro Ile Val Tyr Gln Glu Phe Ile Ser
65              70                  75                  80

Met Phe Glu Gly Ile Glu Gln Ser Pro Thr Asn Tyr His Glu Leu Cys
                85                  90                  95

Asn Met Phe Asn Asp Ile Phe Arg Lys Ala Pro Leu Tyr Gly Asp Leu
            100                 105                 110

Gly Pro Pro Val Tyr Met Ile Met Ala Arg Ile Met Asn Thr Gln Ala
```

-continued

```
                115                 120                 125
Gly Phe Ser Ala Phe Thr Lys Glu Ser Leu Asn Phe His Phe Lys Lys
            130                 135                 140

Leu Phe Asp Thr Trp Gly Leu Phe Leu Ser Ser Lys Asn Ser Arg Asn
145                 150                 155                 160

Val Leu Val Ala Asp Gln Phe Asp Asp Lys His Tyr Gly Trp Phe Ser
                165                 170                 175

Glu Arg Ala Lys Thr Ala Met Met Ile Asn Tyr Pro Gly Arg Thr Phe
            180                 185                 190

Glu Lys Val Phe Ile Cys Asp Glu His Val Pro Tyr His Gly Phe Thr
        195                 200                 205

Ser Tyr Asp Asp Phe Phe Asn Arg Arg Phe Arg Asp Lys Asp Thr Asp
    210                 215                 220

Arg Pro Val Val Gly Gly Val Thr Asp Thr Thr Leu Ile Gly Ala Ala
225                 230                 235                 240

Cys Glu Ser Leu Ser Tyr Asn Val Ser His Asn Val Gln Ser Leu Asp
                245                 250                 255

Thr Leu Val Ile Lys Gly Glu Ala Tyr Ser Leu Lys His Leu Leu His
            260                 265                 270

Asn Asp Pro Phe Thr Pro Gln Phe Glu His Gly Ser Ile Ile Gln Gly
        275                 280                 285

Phe Leu Asn Val Thr Ala Tyr His Arg Trp His Ser Pro Val Asn Gly
    290                 295                 300

Thr Ile Val Lys Ile Val Asn Val Pro Gly Thr Tyr Phe Ala Gln Ala
305                 310                 315                 320

Pro Tyr Thr Ile Gly Ser Pro Ile Pro Asp Asn Asp Arg Asp Pro Pro
                325                 330                 335

Pro Tyr Leu Lys Ser Leu Val Tyr Phe Ser Asn Ile Ala Ala Arg Gln
            340                 345                 350

Ile Met Phe Ile Glu Ala Asp Asn Lys Asp Ile Gly Leu Ile Phe Leu
        355                 360                 365

Val Phe Ile Gly Met Thr Glu Ile Ser Thr Cys Glu Ala Thr Val Cys
370                 375                 380

Glu Gly Gln His Val Asn Arg Gly Asp Asp Leu Gly Met Phe His Phe
385                 390                 395                 400

Gly Gly Ser Ser Phe Ala Leu Gly Leu Arg Lys Asp Ser Lys Ala Lys
                405                 410                 415

Ile Leu Glu Lys Phe Ala Lys Pro Gly Thr Val Ile Arg Ile Asn Glu
            420                 425                 430

Leu Val Ala Ser Val Arg Lys
        435
```

<210> SEQ ID NO 16
<211> LENGTH: 423
<212> TYPE: PRT
<213> ORGANISM: Gymnopilus junonius

<400> SEQUENCE: 16

```
Met Ser Ser Pro Arg Ile Val Leu His Arg Val Gly Gly Trp Leu Pro
1               5                   10                  15

Lys Asp Gln Asn Val Leu Glu Ala Trp Leu Ser Lys Lys Ile Ala Lys
            20                  25                  30

Ala Lys Thr Arg Asn Arg Ala Pro Lys Asp Trp Ala Pro Val Ile Gln
        35                  40                  45
```

```
Asp Phe Gln Arg Leu Ile Glu Thr Asp Ala Glu Ile Tyr Met Gly Phe
 50                  55                  60

His Gln Met Phe Glu Gln Val Pro Lys Lys Thr Pro Tyr Asp Lys Asp
 65                  70                  75                  80

Pro Thr Asn Glu Gln Trp Gln Val Arg Asn Tyr Met His Met Leu Asp
                 85                  90                  95

Leu Phe Asp Leu Ile Ile Thr Glu Ala Pro Asp Phe Glu Gln Asn Asp
            100                 105                 110

Leu Val Gly Phe Pro Ile Asn Ala Ile Leu Asp Trp Pro Met Gly Thr
        115                 120                 125

Pro Gly Gly Leu Thr Ala Phe Ile Asn Pro Lys Val Asn Ile Met Phe
    130                 135                 140

His Lys Met Phe Asp Val Trp Ala Val Phe Leu Ser Ser Pro Ala Ser
145                 150                 155                 160

Cys Tyr Val Leu Asn Thr Ser Asp Ser Gly Trp Phe Gly Pro Ala Ala
                165                 170                 175

Thr Ala Ala Ile Pro Asn Phe Lys Glu Thr Phe Ile Cys Asp Pro Ser
            180                 185                 190

Leu Pro Tyr Leu Gly Tyr Thr Ser Trp Asp Asn Phe Phe Thr Arg Leu
        195                 200                 205

Phe Arg Pro Gly Val Arg Pro Val Glu Phe Pro Asn Asn Asp Ala Ile
    210                 215                 220

Val Asn Ser Ala Cys Glu Ser Thr Val Tyr Asn Ile Ala Pro Asn Ile
225                 230                 235                 240

Lys Pro Leu Asp Lys Phe Trp Ile Lys Gly Glu Pro Tyr Ser Leu Asn
                245                 250                 255

His Ile Leu Asn Asn Asp Pro Tyr Ala Ser Gln Phe Val Gly Gly Thr
            260                 265                 270

Ile Ser Gln Ala Phe Leu Ser Ala Leu Asn Tyr His Arg Trp Ala Ser
        275                 280                 285

Pro Val Asn Gly Asn Ile Val Lys Val Val Asn Val Pro Gly Thr Tyr
    290                 295                 300

Tyr Ala Glu Ser Pro Val Thr Gly Phe Gly Asn Pro Glu Gly Pro Asp
305                 310                 315                 320

Pro Ala Ala Pro Asn Leu Ser Gln Gly Phe Ile Thr Ala Val Ala Ala
                325                 330                 335

Arg Ala Leu Ile Phe Ile Glu Ala Asp Asn Pro Asn Ile Gly Leu Met
            340                 345                 350

Cys Phe Val Gly Val Gly Met Ala Glu Val Ser Thr Cys Glu Val Thr
        355                 360                 365

Val Ser Val Gly Asp Val Lys Lys Gly Asp Glu Ile Gly Met Phe
    370                 375                 380

His Phe Gly Gly Ser Thr His Cys Leu Ile Phe Arg Pro Gln Thr Lys
385                 390                 395                 400

Ile Thr Phe Asn Pro Asp Tyr Pro Val Ser Thr Ala Val Pro Leu Asn
                405                 410                 415

Ala Ala Val Ala Thr Val Val
            420

<210> SEQ ID NO 17
<211> LENGTH: 508
<212> TYPE: PRT
<213> ORGANISM: Psilocybe cubensis

<400> SEQUENCE: 17
```

```
Met Ile Ala Val Leu Phe Ser Phe Val Ile Ala Gly Cys Ile Tyr Tyr
1               5                   10                  15

Ile Val Ser Arg Arg Val Arg Arg Ser Arg Leu Pro Pro Gly Pro Pro
            20                  25                  30

Gly Ile Pro Ile Pro Phe Ile Gly Asn Met Phe Asp Met Pro Glu Glu
            35                  40                  45

Ser Pro Trp Leu Thr Phe Leu Gln Trp Gly Arg Asp Tyr Asn Thr Asp
    50                  55                  60

Ile Leu Tyr Val Asp Ala Gly Gly Thr Glu Met Val Ile Leu Asn Thr
65                  70                  75                  80

Leu Glu Thr Ile Thr Asp Leu Leu Glu Lys Arg Gly Ser Ile Tyr Ser
                85                  90                  95

Gly Arg Leu Glu Ser Thr Met Val Asn Glu Leu Met Gly Trp Glu Phe
                100                 105                 110

Asp Leu Gly Phe Ile Thr Tyr Gly Asp Arg Trp Arg Glu Glu Arg Arg
            115                 120                 125

Met Phe Ala Lys Glu Phe Ser Glu Lys Gly Ile Lys Gln Phe Arg His
    130                 135                 140

Ala Gln Val Lys Ala Ala His Gln Leu Val Gln Gln Leu Thr Lys Thr
145                 150                 155                 160

Pro Asp Arg Trp Ala Gln His Ile Arg His Gln Ile Ala Ala Met Ser
                165                 170                 175

Leu Asp Ile Gly Tyr Gly Ile Asp Leu Ala Glu Asp Pro Trp Leu
            180                 185                 190

Glu Ala Thr His Leu Ala Asn Glu Gly Leu Ala Ile Ala Ser Val Pro
                195                 200                 205

Gly Lys Phe Trp Val Asp Ser Phe Pro Ser Leu Lys Tyr Leu Pro Ala
            210                 215                 220

Trp Phe Pro Gly Ala Val Phe Lys Arg Lys Ala Lys Val Trp Arg Glu
225                 230                 235                 240

Ala Ala Asp His Met Val Asp Met Pro Tyr Glu Thr Met Arg Lys Leu
                245                 250                 255

Ala Pro Gln Gly Leu Thr Arg Pro Ser Tyr Ala Ser Ala Arg Leu Gln
                260                 265                 270

Ala Met Asp Leu Asn Gly Asp Leu Glu His Gln Glu His Val Ile Lys
            275                 280                 285

Asn Thr Ala Ala Glu Val Asn Val Gly Gly Asp Thr Thr Val Ser
290                 295                 300

Ala Met Ser Ala Phe Ile Leu Ala Met Val Lys Tyr Pro Glu Val Gln
305                 310                 315                 320

Arg Lys Val Gln Ala Glu Leu Asp Ala Leu Thr Asn Asn Gly Gln Ile
                325                 330                 335

Pro Asp Tyr Asp Glu Glu Asp Ser Leu Pro Tyr Leu Thr Ala Cys
            340                 345                 350

Ile Lys Glu Leu Phe Arg Trp Asn Gln Ile Ala Pro Leu Ala Ile Pro
                355                 360                 365

His Lys Leu Met Lys Asp Asp Val Tyr Arg Gly Tyr Leu Ile Pro Lys
            370                 375                 380

Asn Thr Leu Val Phe Ala Asn Thr Trp Ala Val Leu Asn Asp Pro Glu
385                 390                 395                 400

Val Tyr Pro Asp Pro Ser Val Phe Arg Pro Glu Arg Tyr Leu Gly Pro
                405                 410                 415
```

```
Asp Gly Lys Pro Asp Asn Thr Val Arg Asp Pro Arg Lys Ala Ala Phe
            420                 425                 430

Gly Tyr Gly Arg Arg Asn Cys Pro Gly Ile His Leu Ala Gln Ser Thr
        435                 440                 445

Val Trp Ile Ala Gly Ala Thr Leu Leu Ser Ala Phe Asn Ile Glu Arg
    450                 455                 460

Pro Val Asp Gln Asn Gly Lys Pro Ile Asp Ile Pro Ala Asp Phe Thr
465                 470                 475                 480

Thr Gly Phe Phe Arg His Pro Val Pro Phe Gln Cys Arg Phe Val Pro
                485                 490                 495

Arg Thr Glu Gln Val Ser Gln Ser Val Ser Gly Pro
            500                 505

<210> SEQ ID NO 18
<211> LENGTH: 494
<212> TYPE: PRT
<213> ORGANISM: Psilocybe cyanescens

<400> SEQUENCE: 18

Met Ala Pro Leu Thr Thr Met Ile Pro Ile Val Leu Ser Leu Leu Ile
1               5                   10                  15

Ala Gly Cys Ile Tyr Tyr Ile Asn Ala Arg Arg Ile Lys Arg Ser Arg
            20                  25                  30

Leu Pro Pro Gly Pro Pro Gly Ile Pro Ile Pro Phe Ile Gly Asn Met
        35                  40                  45

Phe Asp Met Pro Ser Glu Ser Pro Trp Leu Ile Phe Leu Gln Trp Gly
    50                  55                  60

Gln Glu Tyr Gln Thr Asp Ile Ile Tyr Val Asp Ala Gly Gly Thr Asp
65                  70                  75                  80

Met Ile Ile Leu Asn Ser Leu Glu Ala Ile Thr Asp Leu Leu Glu Lys
                85                  90                  95

Arg Gly Ser Leu Tyr Ser Gly Arg Leu Glu Ser Thr Met Val Asn Glu
            100                 105                 110

Leu Met Gly Trp Glu Phe Asp Phe Gly Phe Ile Pro Tyr Gly Glu Arg
        115                 120                 125

Trp Arg Glu Glu Arg Arg Met Phe Ala Lys Glu Phe Ser Glu Lys Asn
    130                 135                 140

Ile Arg Gln Phe Arg His Ala Gln Val Lys Ala Ala Asn Gln Leu Val
145                 150                 155                 160

Arg Gln Leu Thr Asp Lys Pro Asp Arg Trp Ser His His Ile Arg His
                165                 170                 175

Gln Ile Ala Ser Met Ala Leu Asp Ile Gly Tyr Gly Ile Asp Leu Ala
            180                 185                 190

Glu Asp Asp Pro Trp Ile Ala Ala Ser Glu Leu Ala Asn Glu Gly Leu
        195                 200                 205

Ala Val Ala Ser Val Pro Gly Ser Phe Trp Val Asp Thr Phe Pro Phe
    210                 215                 220

Leu Lys Tyr Leu Pro Ser Trp Leu Pro Gly Ala Glu Phe Lys Arg Asn
225                 230                 235                 240

Ala Lys Met Trp Lys Glu Gly Ala Asp His Met Val Asn Met Pro Tyr
                245                 250                 255

Glu Thr Met Lys Lys Leu Ser Ala Gln Gly Leu Thr Arg Pro Ser Tyr
            260                 265                 270

Ala Ser Ala Arg Leu Gln Ala Met Asp Pro Asn Gly Asp Leu Glu His
        275                 280                 285
```

Gln Glu Arg Val Ile Lys Asn Thr Ala Thr Gln Val Asn Val Gly Gly
        290                 295                 300

Gly Asp Thr Thr Val Gly Ala Val Ser Ala Phe Ile Leu Ala Met Val
305                 310                 315                 320

Lys Tyr Pro Glu Val Gln Arg Lys Val Gln Ala Glu Leu Asp Glu Phe
                325                 330                 335

Thr Ser Lys Gly Arg Ile Pro Asp Tyr Asp Glu Asp Asn Asp Ser Leu
            340                 345                 350

Pro Tyr Leu Ser Ala Cys Phe Lys Glu Leu Phe Arg Trp Gly Gln Ile
        355                 360                 365

Ala Pro Leu Ala Ile Ala His Arg Leu Ile Lys Asp Asp Val Tyr Arg
    370                 375                 380

Glu Tyr Thr Ile Pro Lys Asn Ala Leu Val Phe Ala Asn Asn Trp Tyr
385                 390                 395                 400

Gly Arg Thr Val Leu Asn Asp Pro Ser Glu Tyr Pro Asn Pro Ser Glu
                405                 410                 415

Phe Arg Pro Glu Arg Tyr Leu Gly Pro Asp Gly Lys Pro Asp Asp Thr
            420                 425                 430

Val Arg Asp Pro Arg Lys Ala Ala Phe Gly Tyr Gly Arg Arg Val Cys
        435                 440                 445

Pro Gly Ile His Leu Ala Gln Ser Thr Val Trp Ile Ala Gly Val Ala
    450                 455                 460

Leu Val Ser Ala Phe Asn Ile Glu Leu Pro Val Asp Lys Asp Gly Lys
465                 470                 475                 480

Cys Ile Asp Ile Pro Ala Ala Phe Thr Thr Gly Phe Phe Arg
                485                 490

<210> SEQ ID NO 19
<211> LENGTH: 523
<212> TYPE: PRT
<213> ORGANISM: Gymnopilus junonius

<400> SEQUENCE: 19

Met Met Ser Glu Met Asn Gly Met Asp Lys Leu Ala Leu Leu Thr Thr
1               5                   10                  15

Leu Leu Ala Ala Gly Phe Leu Tyr Phe Lys Asn Lys Arg Arg Ser Ala
                20                  25                  30

Leu Pro Phe Pro Pro Gly Pro Lys Lys His Pro Leu Leu Gly Asn Leu
            35                  40                  45

Leu Asp Leu Pro Lys Lys Leu Glu Trp Glu Thr Tyr Arg Arg Trp Gly
        50                  55                  60

Lys Glu Tyr Asn Ser Asp Val Ile His Val Ser Ala Gly Ser Val Asn
65                  70                  75                  80

Leu Ile Ile Val Asn Ser Phe Glu Ala Ala Thr Asp Leu Phe Asp Lys
                85                  90                  95

Arg Ser Ala Asn Tyr Ser Ser Arg Pro Gln Phe Thr Met Val Arg Glu
            100                 105                 110

Leu Met Gly Trp Asn Trp Leu Met Ser Ala Leu Ile Tyr Gly Asp Lys
        115                 120                 125

Trp Arg Glu Gln Arg Arg Leu Phe Gln Lys His Phe Ser Thr Thr Asn
    130                 135                 140

Ala Glu Leu Tyr Gln Asn Thr Gln Leu Glu Tyr Val Arg Lys Ala Leu
145                 150                 155                 160

Gln His Leu Leu Glu Glu Pro Ser Asp Phe Met Gly Ile Thr Arg His

```
            165                 170                 175
Met Ala Gly Gly Val Ser Met Ser Leu Ala Tyr Gly Leu Asn Ile Gln
            180                 185                 190

Lys Lys Asn Asp Pro Phe Val Asp Leu Ala Gln Arg Ala Val His Ser
        195                 200                 205

Ile Thr Glu Ala Ser Val Pro Gly Thr Phe Trp Val Asp Val Met Pro
    210                 215                 220

Trp Leu Lys Tyr Ile Pro Glu Trp Val Pro Gly Ala Gly Phe Gln Lys
225                 230                 235                 240

Lys Ala Arg Val Trp Arg Lys Leu Gln Gln Asp Phe Arg Gln Val Pro
                245                 250                 255

Tyr Gln Ala Ala Leu Lys Asp Met Ala Ser Gly Lys Ala Lys Pro Ser
                    260                 265                 270

Phe Ala Ser Glu Cys Leu Glu Thr Ile Asp Asp Asn Glu Asp Ala Gln
                275                 280                 285

Arg Gln Arg Glu Val Ile Lys Asp Thr Ala Ala Ile Val Phe Ala Ala
            290                 295                 300

Gly Ala Asp Thr Ser Leu Ser Gly Ile His Thr Leu Phe Ala Ala Met
305                 310                 315                 320

Leu Cys Tyr Pro Glu Val Gln Lys Lys Ala Gln Glu Glu Leu Asp Arg
                325                 330                 335

Val Leu Gly Gly Arg Arg Leu Pro Glu Phe Thr Asp Glu Pro Asn Met
            340                 345                 350

Pro Tyr Ile Ser Ala Leu Val Lys Glu Ile Leu Arg Trp Lys Pro Ala
                355                 360                 365

Thr Pro Ile Gly Val Pro His Leu Ala Ser Glu Asp Asp Val Tyr Asn
        370                 375                 380

Gly Tyr Tyr Ile Pro Lys Arg Ala Val Val Ile Gly Asn Ser Trp Ala
385                 390                 395                 400

Met Leu His Asp Glu Glu Thr Tyr Pro Asp Pro Ser Thr Phe Asn Pro
                    405                 410                 415

Asp Arg Phe Leu Thr Thr Asn Lys Ser Thr Gly Lys Leu Glu Leu Asp
                420                 425                 430

Pro Thr Val Arg Asp Pro Ala Leu Met Ala Phe Gly Phe Gly Arg Arg
            435                 440                 445

Met Cys Pro Gly Arg Asp Val Ala Leu Ser Val Ile Trp Leu Thr Ile
        450                 455                 460

Ala Ser Val Leu Ala Thr Phe Asn Ile Thr Lys Ala Ile Asp Glu Asn
465                 470                 475                 480

Gly Lys Glu Leu Glu Pro Asp Val Gln Tyr Trp Ser Gly Leu Ile Val
                485                 490                 495

His Pro Leu Pro Phe Lys Cys Thr Ile Lys Pro Arg Ser Lys Ala Ala
                500                 505                 510

Glu Glu Leu Val Lys Ser Gly Ala Asp Ala Tyr
                515                 520

<210> SEQ ID NO 20
<211> LENGTH: 362
<212> TYPE: PRT
<213> ORGANISM: Psilocybe cubensis

<400> SEQUENCE: 20

Met Ala Phe Asp Leu Lys Thr Glu Asp Gly Leu Ile Thr Tyr Leu Thr
1               5                   10                  15
```

```
Lys His Leu Ser Leu Asp Val Asp Thr Ser Gly Val Lys Arg Leu Ser
            20                  25                  30

Gly Gly Phe Val Asn Val Thr Trp Arg Ile Lys Leu Asn Ala Pro Tyr
        35                  40                  45

Gln Gly His Thr Ser Ile Ile Leu Lys His Ala Gln Pro His Met Ser
    50                  55                  60

Thr Asp Glu Asp Phe Lys Ile Gly Val Glu Arg Ser Val Tyr Glu Tyr
65                  70                  75                  80

Gln Ala Ile Lys Leu Met Met Ala Asn Arg Glu Val Leu Gly Gly Val
                85                  90                  95

Asp Gly Ile Val Ser Val Pro Glu Gly Leu Asn Tyr Asp Leu Glu Asn
            100                 105                 110

Asn Ala Leu Ile Met Gln Asp Val Gly Lys Met Lys Thr Leu Leu Asp
        115                 120                 125

Tyr Val Thr Ala Lys Pro Pro Leu Ala Thr Asp Ile Ala Arg Leu Val
    130                 135                 140

Gly Thr Glu Ile Gly Gly Phe Val Ala Arg Leu His Asn Ile Gly Arg
145                 150                 155                 160

Glu Arg Arg Asp Asp Pro Glu Phe Lys Phe Phe Ser Gly Asn Ile Val
                165                 170                 175

Gly Arg Thr Thr Ser Asp Gln Leu Tyr Gln Thr Ile Ile Pro Asn Ala
            180                 185                 190

Ala Lys Tyr Gly Val Asp Asp Pro Leu Leu Pro Thr Val Val Lys Asp
        195                 200                 205

Leu Val Asp Asp Val Met His Ser Glu Glu Thr Leu Val Met Ala Asp
    210                 215                 220

Leu Trp Ser Gly Asn Ile Leu Leu Gln Leu Glu Glu Gly Asn Pro Ser
225                 230                 235                 240

Lys Leu Gln Lys Ile Tyr Ile Leu Asp Trp Glu Leu Cys Lys Tyr Gly
                245                 250                 255

Pro Ala Ser Leu Asp Leu Gly Tyr Phe Leu Gly Asp Cys Tyr Leu Ile
            260                 265                 270

Ser Arg Phe Gln Asp Glu Gln Val Gly Thr Thr Met Arg Gln Ala Tyr
        275                 280                 285

Leu Gln Ser Tyr Ala Arg Thr Ser Lys His Ser Ile Asn Tyr Ala Lys
    290                 295                 300

Val Thr Ala Gly Ile Ala Ala His Ile Val Met Trp Thr Asp Phe Met
305                 310                 315                 320

Gln Trp Gly Ser Glu Glu Glu Arg Ile Asn Phe Val Lys Lys Gly Val
                325                 330                 335

Ala Ala Phe His Asp Ala Arg Gly Asn Asn Asp Asn Gly Glu Ile Thr
            340                 345                 350

Ser Thr Leu Leu Lys Glu Ser Ser Thr Ala
        355                 360

<210> SEQ ID NO 21
<211> LENGTH: 361
<212> TYPE: PRT
<213> ORGANISM: Psilocybe cyanescens

<400> SEQUENCE: 21

Met Thr Phe Asp Leu Lys Thr Glu Glu Gly Leu Leu Ser Tyr Leu Thr
1               5                   10                  15

Lys His Leu Ser Leu Asp Val Ala Pro Asn Gly Val Lys Arg Leu Ser
            20                  25                  30
```

```
Gly Gly Phe Val Asn Val Thr Trp Arg Val Gly Leu Asn Ala Pro Tyr
        35                  40                  45

His Gly His Thr Ser Ile Ile Leu Lys His Ala Gln Pro His Leu Ser
 50                  55                  60

Ser Asp Ile Asp Phe Lys Ile Gly Val Glu Arg Ser Ala Tyr Glu Tyr
 65                  70                  75                  80

Gln Ala Leu Lys Ile Val Ser Ala Asn Ser Ser Leu Leu Gly Ser Ser
                 85                  90                  95

Asp Ile Arg Val Ser Val Pro Glu Gly Leu His Tyr Asp Val Val Asn
            100                 105                 110

Asn Ala Leu Ile Met Gln Asp Val Gly Thr Met Lys Thr Leu Leu Asp
        115                 120                 125

Tyr Val Thr Ala Lys Pro Pro Ile Ser Ala Glu Ile Ala Ser Leu Val
130                 135                 140

Gly Ser Gln Ile Gly Ala Phe Ile Ala Arg Leu His Asn Leu Gly Arg
145                 150                 155                 160

Glu Asn Lys Asp Lys Asp Asp Phe Lys Phe Phe Ser Gly Asn Ile Val
                165                 170                 175

Gly Arg Thr Thr Ala Asp Gln Leu Tyr Gln Thr Ile Ile Pro Asn Ala
            180                 185                 190

Ala Lys Tyr Gly Ile Asp Asp Pro Ile Leu Pro Ile Val Val Lys Glu
        195                 200                 205

Leu Val Glu Glu Val Met Asn Ser Glu Glu Thr Leu Ile Met Ala Asp
210                 215                 220

Leu Trp Ser Gly Asn Ile Leu Leu Gln Phe Asp Glu Asn Ser Thr Glu
225                 230                 235                 240

Leu Thr Arg Ile Trp Leu Val Asp Trp Glu Leu Cys Lys Tyr Gly Pro
                245                 250                 255

Pro Ser Leu Asp Met Gly Tyr Phe Leu Gly Asp Cys Phe Leu Val Ala
            260                 265                 270

Arg Phe Gln Asp Gln Leu Val Gly Thr Ser Met Arg Gln Ala Tyr Leu
        275                 280                 285

Lys Ser Tyr Ala Arg Asn Val Lys Glu Pro Ile Asn Tyr Ala Lys Ala
290                 295                 300

Thr Ala Gly Ile Gly Ala His Leu Val Met Trp Thr Asp Phe Met Lys
305                 310                 315                 320

Trp Gly Asn Asp Glu Glu Arg Glu Phe Val Lys Lys Gly Val Glu
                325                 330                 335

Ala Phe His Glu Ala Asn Glu Asp Asn Arg Asn Gly Glu Ile Thr Ser
            340                 345                 350

Ile Leu Val Lys Glu Ala Ser Arg Thr
        355                 360

<210> SEQ ID NO 22
<211> LENGTH: 309
<212> TYPE: PRT
<213> ORGANISM: Psilocybe cyanescens

<400> SEQUENCE: 22

Met His Ile Arg Asn Pro Tyr Arg Asp Gly Val Asp Tyr Gln Ala Leu
1               5                   10                  15

Ala Glu Ala Phe Pro Ala Leu Lys Pro His Val Thr Val Asn Ser Asp
            20                  25                  30

Asn Thr Thr Ser Ile Asp Phe Ala Val Pro Glu Ala Gln Arg Leu Tyr
```

```
                35                  40                  45
Thr Ala Ala Leu Leu His Arg Asp Phe Gly Leu Thr Ile Thr Leu Pro
    50                  55                  60

Glu Asp Arg Leu Cys Pro Thr Val Pro Asn Arg Leu Asn Tyr Val Leu
65                  70                  75                  80

Trp Val Glu Asp Ile Leu Lys Val Thr Ser Asp Ala Leu Gly Leu Pro
                85                  90                  95

Asp Asn Arg Gln Val Lys Gly Ile Asp Ile Gly Thr Gly Ala Ser Ala
            100                 105                 110

Ile Tyr Pro Met Leu Ala Cys Ser Arg Phe Lys Thr Trp Ser Met Val
        115                 120                 125

Ala Thr Glu Val Asp Gln Lys Cys Ile Asp Thr Ala Arg Leu Asn Val
    130                 135                 140

Ile Ala Asn Asn Leu Gln Glu Arg Leu Ala Ile Ile Ala Thr Ser Val
145                 150                 155                 160

Asp Gly Pro Ile Leu Val Pro Leu Leu Gln Ala Asn Ser Asp Phe Glu
                165                 170                 175

Tyr Asp Phe Thr Met Cys Asn Pro Pro Phe Tyr Asp Gly Ala Ser Asp
            180                 185                 190

Met Gln Thr Ser Asp Ala Ala Lys Gly Phe Gly Phe Gly Val Asn Ala
        195                 200                 205

Pro His Thr Gly Thr Val Leu Glu Met Ala Thr Glu Gly Gly Glu Ser
    210                 215                 220

Ala Phe Val Ala Gln Met Val Arg Glu Ser Leu Asn Leu Gln Thr Arg
225                 230                 235                 240

Cys Arg Trp Phe Thr Ser Asn Leu Gly Lys Leu Lys Ser Leu Tyr Glu
                245                 250                 255

Ile Val Gly Leu Leu Arg Glu His Gln Ile Ser Asn Tyr Ala Ile Asn
            260                 265                 270

Glu Tyr Val Gln Gly Ala Thr Arg Arg Tyr Ala Ile Ala Trp Ser Phe
        275                 280                 285

Ile Asp Val Arg Leu Pro Asp His Leu Ser Arg Pro Ser Asn Pro Asp
    290                 295                 300

Leu Ser Ser Leu Phe
305

<210> SEQ ID NO 23
<211> LENGTH: 309
<212> TYPE: PRT
<213> ORGANISM: Psilocybe cubensis

<400> SEQUENCE: 23

Met His Ile Arg Asn Pro Tyr Arg Thr Pro Ile Asp Tyr Gln Ala Leu
1               5                   10                  15

Ser Glu Ala Phe Pro Pro Leu Lys Pro Phe Val Ser Val Asn Ala Asp
            20                  25                  30

Gly Thr Ser Ser Val Asp Leu Thr Ile Pro Glu Ala Gln Arg Ala Phe
        35                  40                  45

Thr Ala Ala Leu Leu His Arg Asp Phe Gly Leu Thr Met Thr Ile Pro
    50                  55                  60

Glu Asp Arg Leu Cys Pro Thr Val Pro Asn Arg Leu Asn Tyr Val Leu
65                  70                  75                  80

Trp Ile Glu Asp Ile Phe Asn Tyr Thr Asn Lys Thr Leu Gly Leu Ser
                85                  90                  95
```

-continued

```
Asp Asp Arg Pro Ile Lys Gly Val Asp Ile Gly Thr Gly Ala Ser Ala
                100                 105                 110

Ile Tyr Pro Met Leu Ala Cys Ala Arg Phe Lys Ala Trp Ser Met Val
            115                 120                 125

Gly Thr Glu Val Glu Arg Lys Cys Ile Asp Thr Ala Arg Leu Asn Val
        130                 135                 140

Val Ala Asn Asn Leu Gln Asp Arg Leu Ser Ile Leu Glu Thr Ser Ile
145                 150                 155                 160

Asp Gly Pro Ile Leu Val Pro Ile Phe Glu Ala Thr Glu Glu Tyr Glu
                165                 170                 175

Tyr Glu Phe Thr Met Cys Asn Pro Pro Phe Tyr Asp Gly Ala Ala Asp
            180                 185                 190

Met Gln Thr Ser Asp Ala Ala Lys Gly Phe Gly Phe Gly Val Gly Ala
        195                 200                 205

Pro His Ser Gly Thr Val Ile Glu Met Ser Thr Glu Gly Gly Glu Ser
210                 215                 220

Ala Phe Val Ala Gln Met Val Arg Glu Ser Leu Lys Leu Arg Thr Arg
225                 230                 235                 240

Cys Arg Trp Tyr Thr Ser Asn Leu Gly Lys Leu Lys Ser Leu Lys Glu
                245                 250                 255

Ile Val Gly Leu Leu Lys Glu Leu Glu Ile Ser Asn Tyr Ala Ile Asn
            260                 265                 270

Glu Tyr Val Gln Gly Ser Thr Arg Arg Tyr Ala Val Ala Trp Ser Phe
        275                 280                 285

Thr Asp Ile Gln Leu Pro Glu Glu Leu Ser Arg Pro Ser Asn Pro Glu
290                 295                 300

Leu Ser Ser Leu Phe
305

<210> SEQ ID NO 24
<211> LENGTH: 317
<212> TYPE: PRT
<213> ORGANISM: Panaeolus cyanescens

<400> SEQUENCE: 24

Met His Asn Arg Asn Pro Tyr Arg Asp Val Ile Asp Tyr Gln Ala Leu
1               5                   10                  15

Ala Glu Ala Tyr Pro Pro Leu Lys Pro His Val Thr Val Asn Ala Asp
            20                  25                  30

Asn Thr Ala Ser Ile Asp Leu Thr Ile Pro Glu Val Gln Arg Gln Tyr
        35                  40                  45

Thr Ala Ala Leu Leu His Arg Asp Phe Gly Leu Thr Ile Thr Leu Pro
    50                  55                  60

Glu Asp Arg Leu Cys Pro Thr Val Pro Asn Arg Leu Asn Tyr Val Leu
65                  70                  75                  80

Trp Ile Glu Asp Ile Phe Gln Cys Thr Asn Lys Ala Leu Gly Leu Ser
                85                  90                  95

Asp Asp Arg Pro Val Lys Gly Val Asp Ile Gly Thr Gly Ala Ser Ala
            100                 105                 110

Ile Tyr Pro Met Leu Ala Cys Ala Arg Phe Lys Gln Trp Ser Met Ile
        115                 120                 125

Ala Thr Glu Val Glu Arg Lys Cys Ile Asp Thr Ala Arg Leu Asn Val
    130                 135                 140

Leu Ala Asn Asn Leu Gln Asp Arg Leu Ser Ile Leu Glu Val Ser Val
145                 150                 155                 160
```

```
Asp Gly Pro Ile Leu Val Pro Ile Phe Asp Thr Phe Glu Arg Ala Thr
            165                 170                 175

Ser Asp Tyr Glu Phe Glu Phe Thr Met Cys Asn Pro Pro Phe Tyr Asp
        180                 185                 190

Gly Ala Ala Asp Met Gln Thr Ser Asp Ala Ala Lys Gly Phe Gly Phe
            195                 200                 205

Gly Val Asn Ala Pro His Ser Gly Thr Val Ile Glu Met Ala Thr Glu
        210                 215                 220

Gly Gly Glu Ala Ala Phe Val Ala Gln Met Val Arg Glu Ser Met Lys
225                 230                 235                 240

Leu Gln Thr Arg Cys Arg Trp Phe Thr Ser Asn Leu Gly Lys Leu Lys
            245                 250                 255

Ser Leu His Glu Ile Val Ala Leu Leu Arg Glu Ser Gln Ile Thr Asn
        260                 265                 270

Tyr Ala Ile Asn Glu Tyr Val Gln Gly Thr Thr Arg Arg Tyr Ala Leu
    275                 280                 285

Ala Trp Ser Phe Thr Asp Ile Lys Leu Thr Glu Glu Leu Tyr Arg Pro
        290                 295                 300

Ser Asn Pro Glu Leu Gly Pro Leu Cys Ser Thr Phe Val
305                 310                 315

<210> SEQ ID NO 25
<211> LENGTH: 297
<212> TYPE: PRT
<213> ORGANISM: Gymnopilus junonius

<400> SEQUENCE: 25

Met His Ser Arg Asn Pro Tyr Arg Ser Pro Asp Phe Ala Ala Leu
1               5                   10                  15

Ser Ala Ala Tyr Pro Pro Leu Ser Pro Tyr Ile Thr Thr Asp Leu Ser
            20                  25                  30

Ser Gly Arg Lys Thr Ile Asp Phe Arg Asn Glu Ala Gln Arg Arg
        35                  40                  45

Leu Thr Glu Ala Ile Met Leu Arg Asp Phe Gly Val Val Leu Asn Ile
50                  55                  60

Pro Ser Asn Arg Leu Cys Pro Pro Val Pro Asn Arg Met Asn Tyr Val
65                  70                  75                  80

Leu Trp Ile Gln Asp Ile Val Tyr Ala His Gln Thr Ile Leu Gly Val
            85                  90                  95

Ser Ser Arg Arg Ile Arg Gly Leu Asp Ile Gly Thr Gly Ala Thr Ala
        100                 105                 110

Ile Tyr Pro Ile Leu Ala Cys Lys Lys Glu Gln Ser Trp Glu Met Val
    115                 120                 125

Ala Thr Glu Leu Asp Asp Tyr Ser Tyr Glu Cys Ala Cys Asp Asn Val
        130                 135                 140

Ser Ser Asn Asn Met Gln Thr Ser Ile Lys Val Lys Lys Ala Ser Val
145                 150                 155                 160

Asp Gly Pro Ile Leu Phe Pro Val Glu Asn Gln Asn Phe Asp Phe Ser
            165                 170                 175

Met Cys Asn Pro Pro Phe Tyr Gly Ser Lys Glu Val Ala Gln Ser
        180                 185                 190

Ala Glu Ser Lys Glu Leu Pro Pro Asn Ala Val Cys Thr Gly Ala Glu
    195                 200                 205

Ile Glu Met Ile Phe Ser Gln Gly Gly Glu Glu Gly Phe Val Gly Arg
```

```
            210                 215                 220
Met Val Glu Glu Ser Glu Arg Leu Gln Thr Arg Cys Lys Trp Tyr Thr
225                 230                 235                 240

Ser Met Leu Gly Lys Met Ser Ser Val Ser Thr Ile Val Gln Ala Leu
            245                 250                 255

Arg Ala Arg Ser Ile Met Asn Tyr Ala Leu Thr Glu Phe Val Gln Gly
                260                 265                 270

Gln Thr Arg Arg Trp Ala Ile Ala Trp Ser Phe Ser Asp Thr His Leu
            275                 280                 285

Pro Asp Ala Val Ser Arg Ile Ser Ser
            290                 295

<210> SEQ ID NO 26
<211> LENGTH: 309
<212> TYPE: PRT
<213> ORGANISM: Gymnopilus dilepis

<400> SEQUENCE: 26

Met His Ile Arg Asn Pro Tyr Leu Thr Pro Asp Tyr Glu Ala Leu
1               5                   10                  15

Ala Glu Ala Phe Pro Ala Leu Lys Pro Tyr Val Thr Val Asn Pro Asp
                20                  25                  30

Lys Thr Thr Thr Ile Asp Phe Ala Ile Pro Glu Ala Gln Arg Leu Tyr
            35                  40                  45

Thr Ala Ala Leu Leu Tyr Arg Asp Phe Gly Leu Thr Ile Thr Leu Pro
        50                  55                  60

Pro Asp Arg Leu Cys Pro Thr Val Pro Asn Arg Leu Asn Tyr Val Leu
65                  70                  75                  80

Trp Ile Gln Asp Ile Leu Gln Ile Thr Ser Ala Ala Leu Gly Leu Pro
                85                  90                  95

Glu Ala Arg Gln Val Lys Gly Val Asp Ile Gly Thr Gly Ala Ala Ala
            100                 105                 110

Ile Tyr Pro Ile Leu Gly Cys Ser Leu Ala Lys Asn Trp Ser Met Val
        115                 120                 125

Gly Thr Glu Val Glu Gln Lys Cys Ile Asp Ile Ala Arg Gln Asn Val
    130                 135                 140

Ile Ser Asn Gly Leu Gln Asp Arg Ile Thr Ile Thr Ala Asn Thr Ile
145                 150                 155                 160

Asp Ala Pro Ile Leu Leu Pro Leu Phe Glu Gly Asp Ser Asn Phe Glu
                165                 170                 175

Trp Glu Phe Thr Met Cys Asn Pro Pro Phe Tyr Asp Gly Ala Ala Asp
            180                 185                 190

Met Glu Thr Ser Gln Asp Ala Lys Gly Phe Gly Phe Gly Val Asn Ala
        195                 200                 205

Pro His Thr Gly Thr Val Val Glu Met Ala Thr Asp Gly Gly Glu Ala
    210                 215                 220

Ala Phe Val Ser Gln Met Val Arg Glu Ser Leu His Leu Lys Thr Arg
225                 230                 235                 240

Cys Arg Trp Phe Thr Ser Asn Leu Gly Lys Leu Lys Ser Leu His Glu
                245                 250                 255

Ile Val Gly Leu Leu Arg Glu His Gln Ile Thr Asn Tyr Ala Ile Asn
            260                 265                 270

Glu Tyr Val Gln Gly Thr Thr Arg Arg Tyr Ala Ile Ala Trp Ser Phe
        275                 280                 285
```

```
Thr Asp Leu Arg Leu Ser Asp His Leu Pro Arg Pro Pro Asn Pro Asp
    290                 295                 300

Leu Ser Ala Leu Phe
305
```

<210> SEQ ID NO 27
<211> LENGTH: 4767
<212> TYPE: DNA
<213> ORGANISM: Saccharomyces cerevisiae
<220> FEATURE:
<223> OTHER INFORMATION: ARO1 gene

<400> SEQUENCE: 27

| | | | | | |
|---|---|---|---|---|---|
| atggttcaac | tagccaaggt | tccaatacta | ggaaacgata | taatacacgt | tggatataat | 60 |
| atacacgatc | atcttgtaga | gacaattatt | aaacactgtc | cttcttctac | ttacgtcatc | 120 |
| tgtaacgata | ctaaccttag | caaggtacct | tattaccagc | aactggttct | ggagttcaaa | 180 |
| gcaagtcttc | ccgaaggctc | cagactacta | acctacgtgg | tcaaaccggg | cgagacgtct | 240 |
| aagagtaggg | agacgaaggc | gcagttagag | gattatcttt | tagtagaagg | gtgcactcgt | 300 |
| gatacggtca | tggtagccat | cggcggaggt | gtcatcggtg | acatgatcgg | tttcgtagcc | 360 |
| tccacgttca | tgagaggtgt | gagggtagta | caggttccga | cgtctctttt | agcaatggta | 420 |
| gactcatcca | taggcggtaa | aacggcgatc | gatactccgc | taggaaagaa | cttcattgga | 480 |
| gcctttttggc | agccaaaatt | tgttcttgtg | atatcaagt | ggcttgaaac | actagctaaa | 540 |
| cgtgaattta | tcaacggcat | ggcagaagtg | atcaagacag | cgtgcatctg | aacgctgat | 600 |
| gaatttactc | gtctcgaatc | caacgcgtca | ctgttcctaa | cgtagtaaa | tggtgcgaaa | 660 |
| aatgtaaagg | tgactaacca | gctgacgaac | gagatagatg | agatcagcaa | cacggatatt | 720 |
| gaagccatgt | tggaccatac | ttataaactg | gtattagaga | gtattaaggt | taaagcggag | 780 |
| gtggtaagca | gcgatgaaag | ggagagcagt | cttaggaacc | tttttaaactt | cgggcatagc | 840 |
| ataggtcacg | cgtatgaagc | catactgaca | ccccaggctt | tacatggaga | gtgcgtatcc | 900 |
| atcggcatgg | taaagaagc | agaactatca | aggtattttg | ggatactttc | tccgacccag | 960 |
| gtggcgcgtc | taagcaaaat | tctagttgcg | tacggattgc | ccgttagccc | cgatgagaaa | 1020 |
| tggtttaaag | agcttacact | tcataagaag | acacccttgg | acatactgct | aaagaagatg | 1080 |
| agcatcgaca | gaaaaatga | aggaagcaag | aagaaggtcg | taatcctaga | gtctatcggc | 1140 |
| aaatgttacg | gagactcagc | tcagtttgtt | tcagacgaag | acttacgttt | tatattgaca | 1200 |
| gatgaaacac | tagtatatcc | tttttaaggat | attcccgctg | atcagcagaa | agtcgtgatt | 1260 |
| ccacccggaa | gtaaatcaat | aagcaatcgt | gctttaatct | tagcagctct | gggggaggga | 1320 |
| cagtgcaaga | tcaagaacct | attacactcc | gacgacacca | acatatgct | gaccgcagtc | 1380 |
| cacgagttaa | aggtgctac | catcagttgg | gaggataacg | gagaaacagt | ggtcgtagag | 1440 |
| ggccatggcg | ggagcactct | atcggcttgt | gctgatccct | tatacttagg | caacgcgggg | 1500 |
| acggcgagta | gattcttaac | atcactggcg | gcactagtga | acagtacatc | ctcccaaaag | 1560 |
| tatatcgtac | taacaggcaa | cgcaaggatg | cagcaacgtc | cgatagcgcc | ccttgttgac | 1620 |
| agcttacgtg | ctaacgggac | aaagatcgag | tacttgaaca | cgaaggttc | tttgccgatc | 1680 |
| aaagtgtaca | ctgattctgt | atttaaaggc | ggccgtattg | agttggctgc | gacagttagt | 1740 |
| tcccaatacg | tgagcagtat | cctgatgtgt | gcgccttacg | cagaagagcc | cgtgacttta | 1800 |
| gctttggtag | gtgggaaacc | gatcagtaaa | ctatacgttg | atatgacaat | taagatgatg | 1860 |
| gaaaagttcg | gcatcaatgt | ggagacctca | accacggaac | cctacacata | ctacattccg | 1920 |

```
aagggcatt acattaatcc aagtgagtac gtaatcgaga gcgacgcttc atccgctacc    1980
tatccgttag cattcgccgc aatgaccggt accaccgtaa cagtccccaa catcggcttt    2040
gaatctctgc agggcgacgc tagattcgca agagacgtcc taaagccgat ggggtgtaaa    2100
atcacccaaa cggctacgtc tacaaccgtc agtggaccac ccgtcggtac gctaaagcca    2160
ttaaaacacg ttgatatgga accaatgaca gacgccttct taaccgcatg cgttgtagcc    2220
gcaatcagtc atgactccga ccccaattca gcgaacacta ctactatcga ggggatcgca    2280
aaccaagggg ttaaagaatg caacagaatc ttagcgatgg ctaccgagct ggcaaagttt    2340
ggagtaaaga caacagaact tcccgatggc ataccaggtcc atgggctaaa ttccatcaag    2400
gaccttaaag tcccatctga cagctcagga cccgtcggag tctgtactta tgatgaccat    2460
agggttgcca tgtcattttc ccttttggct ggcatggtaa acagtcagaa tgagagagat    2520
gaagtggcaa acccagttag gatcttagag aggcactgca ccggaaagac gtggccaggc    2580
tggtgggacg ttctgcacag cgaacttgga gcgaagctgg atggtgccga ccgctagaa    2640 tgcacatcca aaagaactc taagaagagc gtagtcataa taggcatgag agctgcgggc    2700
aaaactacta tctctaagtg gtgcgcaagt gcgctgggtt acaagttggt agatttagat    2760
gaattgttcg agcagcagca taataaccaa tcagtaaaac aatttgtagt cgagaatggt    2820
tgggagaaat tcagagagga agagaccagg atattcaagg aggttattca aaattacggc    2880
gacgacgggt atgtctttag cactggggga gggatcgtcg aatccgcgga gagcaggaaa    2940
gcactaaagg acttcgccag ttccggtggg tatgtgcttc acttacatcg tgatatagag    3000
gagacgatag tcttcctaca aagtgatcca tccaggccgg cgtatgttga ggagattagg    3060
gaggtctgga accgtagaga aggctggtat aaagaatgta gtaattttag cttttcgca    3120 cctcactgta gcgcagaggc ggagtttcaa gcacttagac gttcattcag taagtatata    3180
gctacgatca cggggtccg tgaaatagag attcctagtg ggaggagtgc gtttgtatgc    3240 ttaactttg acgatctaac tgagcaaacg gagaatctga cgcctatatg ctacgggtgt    3300
gaagccgtag aggtgcgtgt tgatcatctt gccaattatt ccgcagactt cgttagcaag    3360
caattaagca tactgagaaa agcgaccgac agtatacca ttatcttcac cgtccgtact    3420
atgaaacaag gcggtaattt tcccgatgaa gagttcaaga cattgcgtga gttgtacgac    3480
atagctctta aaaacggagt ggagttcctt gatttggaac ttactctgcc tacagatata    3540
cagtacgaag tcatcaacaa gagaggtaat acgaagatca ttgggtctca tcatgacttc    3600
cagggtttgt acagctggga cgatgctgaa tgggaaaaca gattcaatca ggcactgact    3660
cttgacgtag atgtggtgaa atttgtgggt accgcggtga atttcgagga caacttacgt    3720
ttggaacatt ttcgtgacac gcacaaaaat aaaccactaa tagcagttaa catgacgtct    3780
aagggctcaa tcagtagggt actaaataat gtattgactc cggttacttc agacctttta    3840
ccgaacagcg cagcgcctgg tcaattgacg gttgcacaga ttaataaaat gtatacatct    3900
atgggaggaa ttgagcctaa agagctattt gtggtgggga agccaatcgg ccactcaaga    3960
tcacctatac tacacaatac tgggtatgag attttgggtc tacctcacaa attcgataaa    4020
tttgagacgg aaagcgcaca attagtgaag gagaaattgt tagacgggaa caagaatttc    4080
ggtggtgcag cggtgaccat ccctttaaag ctagacataa tgcagtacat ggatgaactt    4140
acggacgctg cgaaggtgat tggggcggta aacacagtaa tcccctttggg taacaagaaa    4200 ttcaagggtg ataatacgga ctggttaggg ataaggaacg cacttataaa taatggtgtg    4260
```

| | | | |
|---|---|---|---|
| cccgagtacg | tggggcatac tgccggactt | gtaataggtg ctggtggtac | cagtagggcg 4320 |
| gcactgtacg | cttttgcatag cttaggttgc | aagaagatct | ttatcatcaa tagaacaact 4380 |
| agtaaactga | agccactgat agaatcacta | ccctccgagt ttaacatcat | tggaatagag 4440 |
| tctacgaaat | ccatcgagga gattaaagaa | cacgtcggag tcgctgttag | ctgcgtgcct 4500 |
| gccgataagc | ccttagatga cgagctactg | agtaagttag aacgtttcct | tgtcaagggt 4560 |
| gcacatgcgg | ctttcgtccc aacactgcta | gaggctgcct ataaacccag | cgtaacacct 4620 |
| gttatgacca | taagtcagga caagtatcaa | tggcacgtgg tgccgggttc | ccagatgctg 4680 |
| gtccatcaag | gtgttgcaca atttgaaaaa | tggactggtt tcaaggggcc | cttcaaagcc 4740 |
| atatttgacg | ccgtgactaa agagtaa | | 4767 |

<210> SEQ ID NO 28
<211> LENGTH: 1131
<212> TYPE: DNA
<213> ORGANISM: Saccharomyces cerevisiae
<220> FEATURE:
<223> OTHER INFORMATION: ARO2 gene

<400> SEQUENCE: 28

| | | | |
|---|---|---|---|
| atgtccacat | tcggtaaact tttccgtgtc | actacatacg gcgagtcaca | ctgcaaatct 60 |
| gtggggtgca | tagtagacgg cgttccgccg | ggcatgagtt taaccgaagc | ggacattcaa 120 |
| cctcagctta | cccgtaggag gcccggtcag | agcaagttat ccaccccgag | ggacgaaaag 180 |
| gaccgtgtag | agatccaaag cggaacggaa | tttgggaaga cacttggtac | gcctatcgct 240 |
| atgatgatta | aaaacgagga tcaacgtccg | cacgattact ccgacatgga | caagttccct 300 |
| aggccgagtc | acgccgattt tacgtactca | gagaaatacg gaataaaagc | ctccagcggt 360 |
| gggggccgtg | cttccgcgag agaaaccatt | ggaagagtag catccggtgc | aatagcagag 420 |
| aagttcctag | cacagaactc aaatgttgaa | attgtcgctt tcgtcacgca | aataggtgag 480 |
| atcaagatga | accgtgacag tttcgaccca | gaatttcaac accttctaaa | tacaattacg 540 |
| agggagaagg | tagatagcat gggtccaata | agatgccccg acgcttccgt | cgcgggattg 600 |
| atggtgaagg | aaattgaaaa atatcgtggg | aacaaggatt ctattggggg | tgtagtaact 660 |
| tgcgtagtca | gaaatctacc tacagggttg | ggtgaaccgt gttttgacaa | actggaggcg 720 |
| atgctggcac | atgccatgtt atccatacca | gcaagtaaag gatttgaaat | aggatctggc 780 |
| ttccagggtg | taagcgtacc aggaagcaaa | cacaatgatc cctttactt | tgaaaaagag 840 |
| actaaccgtc | ttcgtacaaa gacaaacaac | tccggtgggg tgcaagggg | catctctaat 900 |
| ggtgagaaca | tttactttc cgtaccattt | aagagcgtgg ctacaataag | ccaagagcaa 960 |
| aagaccgcaa | cttacgatgg agaagaagga | atcctcgcag ctaagggtag | gcacgatcct 1020 |
| gcggtcacac | cgcgtgcaat tcccatagtg | gaagctatga ccgccctagt | actagcagat 1080 |
| gcgttactaa | tacagaaagc cagggatttt | tctaggtcag tcgtacatta | a 1131 |

<210> SEQ ID NO 29
<211> LENGTH: 1113
<212> TYPE: DNA
<213> ORGANISM: Saccharomyces cerevisiae
<220> FEATURE:
<223> OTHER INFORMATION: ARO3 gene

<400> SEQUENCE: 29

| | | | |
|---|---|---|---|
| atgttcatca | agaatgacca tgctggtgat | agaaagagac tagaggactg | gcgtataaag 60 |
| ggttatgacc | ctctaactcc gcctgatttg | ctacagcacg agtttcctat | atcagcaaaa 120 |

```
ggggaagaaa atatcatcaa ggctcgtgat agtgtatgtg atatactgaa cggaaaggat      180
gacagacttg tgatagtaat tggaccctgt tctctgcatg atccgaaggc ggcctacgac      240
tatgccgaca gattagccaa aatatccgaa aagctgtcaa aagatctttt aattatcatg      300
cgtgcatacc tagagaagcc tcgtacaacc gttggatgga aagggttgat aaacgacccg      360
gatatgaaca atagttttca gattaataaa ggccttcgta taagccgtga gatgtttata      420
aaactagttg agaaattacc tattgcagga gaaatgcttg acacgatttc ccctcagttc      480
ttatctgact gtttctcact aggtgcaatt ggtgctagga ctaccgagtc acagttacat      540
cgtgaactgg ccagcggtct gtctttcccc attggcttta aaaatggtac cgatggtggc      600
cttcaagtag caattgatgc tatgagagct gcggcccacg aacactactt tttgtctgtg      660
accaaacctg gcgtaacagc gattgtggga actgaaggga acaaggacac cttcctaatc      720
ctgagagggg gcaagaacgg gactaatttt gacaaggagt cagttcaaaa cactaagaag      780
caattggaga aggcgggcct tactgacgat tctcagaaga gaatcatgat agactgcagc      840
catggcaact caaataaaga tttcaaaaat caacccaaag tcgccaagtg tatctacgat      900
caactaaccg aaggagaaaa tagtttatgc ggggtgatga tagagagtaa tataaacgaa      960
ggaagacagg atattcctaa ggaaggcgga agagagggtc tgaagtacgg gtgttctgtg     1020
acagacgctt gcataggatg ggagagcacg gaacaggttt tggagctgct ggcagaaggg     1080
gtgcgtaata gaaggaaagc cttaaagaag taa                                  1113

<210> SEQ ID NO 30
<211> LENGTH: 1113
<212> TYPE: DNA
<213> ORGANISM: Saccharomyces cerevisiae
<220> FEATURE:
<223> OTHER INFORMATION: ARO4 K2229L gene

<400> SEQUENCE: 30
atgagcgaat ctccgatgtt cgccgcaaac ggcatgccta aggtaaatca aggggccgag       60
gaggacgtga gaatattagg ttatgacccg cttgccagtc ctgcattgct tcaggtacag      120
attccagcaa cgccaacgtc cttagaaaca gcaaaaaggg gacgtcgtga agctatagac      180
atcatcactg gcaaggacga ccgtgtccta gtaatagttg gtccgtgctc tatccatgac      240
cttgaggctg cacaggagta tgcactaagg ttgaagaaat tgtctgatga actgaaaggt      300
gatcttagta taatcatgcg tgcatattta gagaaaccgc gtacgacggt aggctggaaa      360
gggctaatta acgatccgga tgtgaataat acctttaaca tcaacaaggg tctacagagt      420
gcgcgtcagt tattcgtgaa cttaacaaat atcggactgc cgataggctc cgagatgctg      480
gacacgatat ctccccagta tttggctgac cttgtttctt ttggagctat aggtgcaagg      540
actactgaga gtcagttaca tagagagttg gcatcaggac ttagcttccc tgtaggattt      600
aagaacggta cagacggcac tcttaatgtc gcggtcgatg cctgccaggc agccgcccat      660
tcacatcatt ttatgggagt gacattacac ggggtggccg ctatcacaac gactaaaggg      720
aatgagcact gttttgttat ccttagagga ggaaagaaag gtacgaatta tgatgcgaaa      780
agtgtagcag aggccaaagc gcaacttcct gccggttcaa acggactat gattgactat       840 tcccatggaa actcaaataa ggactttagg aatcagccaa aagttaacga tgtggtatgc      900
gaacagatcg cgaacggtga aaatgcgatt acgggtgtta tgatcgagtc aaatataaat      960
gaaggtaacc aaggtatccc ggcagagggc aaagcgggcc tgaagtacgg tgtatctatt     1020
```

```
acggatgcct gtataggttg ggagacaacc gaagacgtcc taaggaaact tgccgccgcg    1080
gttagacaga gacgtgaagt caataagaag taa                                 1113

<210> SEQ ID NO 31
<211> LENGTH: 525
<212> TYPE: DNA
<213> ORGANISM: Escherichia coli
<220> FEATURE:
<223> OTHER INFORMATION: AROL gene

<400> SEQUENCE: 31
atgacccagc cattatttct gatcggtcct cgtgggtgcg ggaaaacgac ggttggcatg      60
gccttagctg acagtttgaa tcgtagattc gtggacaccg accagtggct acagtctcag    120
cttaacatga cggtggccga aattgtagaa cgtgaagaat gggctggttt tcgtgcaaga    180
gaaacagccg cattggaagc tgtgacggcg ccttcaacgg tgatagctac gggaggtggt    240
attattttga ccgaatttaa taggcacttc atgcagaata atggcatagt ggtttaccta    300
tgcgctcctg tgtctgtctt ggtaaaccgt ttgcaagccg caccgaaaga agacttgcgt    360
ccaaccctga cggggaagcc actgtctgag gaagtgcaag aggtactgga ggaaagggac    420
gctctatacc gtgaggtggc tcacatcata attgacgcta cgaatgagcc atcacaggta    480
atttctgaga tccgttcagc gttggcccaa accatcaatt gttaa                    525

<210> SEQ ID NO 32
<211> LENGTH: 675
<212> TYPE: DNA
<213> ORGANISM: Saccharomyces cerevisiae
<220> FEATURE:
<223> OTHER INFORMATION: TRP1 gene

<400> SEQUENCE: 32
atgtcagtga ttaactttac aggctcctca ggtcccttgg tcaaggtctg cggcttgcaa      60
tcaacagagg ccgctgaatg cgccctagac tcagatgcag acctttttagg catcatctgt    120 gtccccaaca gaaagcgtac tattgatcct gttattgcgc gtaagatcag ttctttggtc    180
aaggcgtata gaactcctc aggaacccccc aagtatctgg tagggtatt caggaatcaa    240 cctaaagaag acgtcttggc cctagttaat gactacggca tagacatagt ccagttgcac    300
ggagacgaaa gctggcaaga atatcaggaa tttttgggc tgccggttat aaaaaggctg    360
gttttcccta aggactgtaa catactgtta tcagccgcat cacagaagcc gcattccttt    420
atacctcttt tcgactccga ggccggaggc actggtgaat tactgactg aacagcatt     480 tcagattggg tagggaggca ggagagccca gaatctcttc attttatgtt ggcagggggc    540
cttacgccgg aaaatgttgg agatgcattg aggttgaacg gagttatagg tgtgatgtc    600 agtggtgggg ttgaaacgaa tggtgttaaa gacagcaaca aaatagcaaa ttttgtcaag    660
aatgccaaaa agtaa                                                     675

<210> SEQ ID NO 33
<211> LENGTH: 1524
<212> TYPE: DNA
<213> ORGANISM: Saccharomyces cerevisiae
<220> FEATURE:
<223> OTHER INFORMATION: TRP2 S76L gene

<400> SEQUENCE: 33
atgacggcga gcattaaaat tcagccagac attgacagtt taagcagtt gcagcaacag       60 aatgacgact cttccattaa catgtatccc gtgtatgcgt atctgccttc tttggatttg    120
```

```
acacctcacg ttgcttactt aaagttagct caacttaata atccagatag aaaggagtct      180
ttcttacttg aaagtgctaa gaccaataat gagctggaca gatatctttt cataggggatc     240 agtccaagga agaccattaa gaccgggccc actgaaggca ttgagactga cccattagaa      300
atccttgaaa aagaaatgtc tactttcaaa gtcgccgaaa acgtcccagg ccttcccaaa      360
ttaagcggcg gggcgatagg ttacatatca tacgactgtg tacgttactt cgaacccaag      420
actaggcgtc ccttgaaaga tgtgcttagg ttaccagagg cgtacttgat gctttgtgac      480
acgataatcg catttgacaa tgtcttccaa aggtttcaaa ttattcacaa tattaacaca      540
aacgaaacgt ctttggagga aggataccag gcggctgcgc agataatcac ggatattgta      600
tctaagttga cagacgacag ctcccccatt ccgtacccgg agcaacccccc tatcaaacta     660 aaccaaacct ttgaatccaa cgtaggcaaa gaggggtatg aaaatcacgt ctccactctc      720
aaaaagcaca taagaaaagg tgacataatc caaggtgtgc ccagccagag agtggcgagg      780
cctacatctt tacatccatt caacatatat aggcatctta gaaccgtgaa cccatcacct      840
tatctatttt acatagactg cctagatttc cagataatag gggctagtcc cgaattgctg      900
tgtaaatcag attcaaagaa tcgtgttatt acacacccca tagctggcac agtcaagagg      960
ggtgctacca ctgaggaaga tgacgctctg gcagatcagc tacgtggttc tttgaaagat      1020
agggctgagc atgttatgct ggttgactta gcaagaaacg acatcaatcg tatatgcgat      1080
cccctaacga cttccgttga caaacttttg accattcaga agttcagcca cgtacagcac      1140
ttagtctctc aggtctctgg cgtcctaagg cctgagaaaa ctcgtttcga tgcattcaga      1200
agcatatttc ccgcgggtac agtgagtggg gccccaaagg tgccgtgcaat ggagcttata    1260 gccgagctag aaggcgagcg taggggagtg tacgcagggg ccgtaggcca ttggtcttat     1320
gacggcaaga ccatggataa ttgtattgca ctaaggacca tggtctataa agatgggatt     1380
gcatacttgc aggcaggagg tgggattgtc tatgacagcg atgagtacga tgagtatgta     1440
gaaacaatga ataaaatgat ggcgaatcat tccacgatag tgcaggcgga ggagttatgg     1500
gcggatattg tgggtagtgc ataa                                            1524
```

<210> SEQ ID NO 34
<211> LENGTH: 1455
<212> TYPE: DNA
<213> ORGANISM: Saccharomyces cerevisiae
<220> FEATURE:
<223> OTHER INFORMATION: TRP3 gene

<400> SEQUENCE: 34

```
atgtctgtcc acgcagccac caacccgata aataagcatg tcgttctgat tgataattac      60
gactccttca cgtggaatgt ttatgagtat ctttgccagg agggagcgaa ggttagcgtt     120
taccgtaatg acgctatcac ggtcccagaa attgcagcac tgaatcccga taccccttctg   180 atatcaccag gcccgggcca tcccaagaca gattctggta ttagcagaga ttgcatcaga    240
tacttcactg gaaaaattcc agtttttggg atatgtatgg ggcagcaatg catgtttgac    300
gtgtttggcg gggaagtggc ttatgcgggt gaaatagtgc acggaaagac tagtcccata   360
tcccatgata actgcggtat ctttaagaat gtccccccagg gtattgcagt tacaagatat    420
catagcttgg ctggcactga aagtagtctg cctagctgcc taaaggtgac tgcctctact    480
gaaaacggga taatcatggg ggtaaggcac aagaagtaca ccgtcgaggg ggtgcaattc    540
cacccagaga gtatttttaac cgaagaagga catctaatga tccgtaatat tcttaatgtt   600
```

```
tctggcggaa cgtgggagga aaataaatca agcccatcca attccatcct agataggata    660
tacgccaggc gtaaaattga cgtaaacgaa cagtcaaaga ttcccggttt cacctttcag    720
gacttacaat ctaactatga tcttggcctt gccccgcctc tgcaagattt ttataccgtg    780
ctgagcagta gtcataagag ggctgtggtc ctagcggagg tgaagcgtgc ctcccctagc    840
aaaggtccaa tctgcctgaa ggccgttgct gctgaacaag cccttaaata tgctgaggct    900
ggggcgagtg caattagcgt tctaacagaa ccccactggt tccacgggag ccttcaagac    960
cttgtgaatg taagaaagat cttggatcta aaatttccgc caaagagag accctgcgtg    1020 cttaggaaag agtttatatt ttccaaatac caaatattgg aggcacgtct agctggtgca    1080
gatactgtcc ttttgattgt aaagatgttg tcccaaccat tactgaaaga gctatatagt    1140
tactcaaagg atttaaacat ggagccgtta gtggaagtaa atagcaagga ggagctacaa    1200
cgtgccctgg aaattggtgc caaggttgtt ggagttaaca atcgtgactt gcattccttc    1260
aacgtagact tgaatacaac aagtaatttg gtcgaatcta tcccaaaaga tgtgctgttg    1320
attgcacttt ccggtatcac aacacgtgat gacgccgaaa agtataaaaa ggagggggtg    1380
cacgggtttt tggtgggtga ggcgttaatg aaatctacag atgtaaagaa gtttattcat    1440
gagctgtgcg aataa                                                    1455

<210> SEQ ID NO 35
<211> LENGTH: 1143
<212> TYPE: DNA
<213> ORGANISM: Saccharomyces cerevisiae
<220> FEATURE:
<223> OTHER INFORMATION: TRP4 gene

<400> SEQUENCE: 35
atgagcgaag ctactctatt aagttatacc aaaaagctac tagcaagccc acctcagctt     60
agttccaccg acctacacga tgcactactt gtcatcctaa gtctacttca gaagtgcgac    120
accaattctg atgagtcctt gtctatttat acgaaggtgt cttcctttt aacagcccta    180 agggtgacta agttagatca taaggcggaa tatattgccg aggctgcaaa agcagttttg    240
cgtcactcag atcggtcga tctacccttta cctaaaaagg atgagctgca tcctgaagat    300
ggtcctgtta tcttggacat tgtgggtact gggggtgatg gacagaatac ctttaacgtg    360
tcaacgtcag ccgctattgt ggcctcaggt attcagggac tgaagatttg caaacacgga    420
ggtaaagcat ctacctcaaa cagcggagct ggagatctga ttgggacatt gggatgcgat    480
atgttcaaag tgaatagtag cacagtcccc aaattgtggc cagacaatac atttatgttc    540
ttattggctc cattctttca tcatgggatg ggtcatgtaa gcaagattcg taagtttctt    600
ggaataccta cggtatttaa cgtattgggg ccgctgttac accccgtatc ccatgtgaat    660
aagaggatac ttggagtgta ttcaaaagag ttggcgccag aatatgcgaa ggcagcagcc    720
ttggtctatc cagggtcaga aacgtttatt gtgtggggcc atgttgggct tgacgaggtg    780
agccccatag gaaagactac cgtgtggcac atcgatccga caagctcaga actaaagttg    840
aagaccttcc agctggagcc atctatgttc ggtctggagg agcacgagct gagtaaatgc    900
gcctcatatg gacctaagga gaatgctcgt atattaaagg aggaagtcct ttccggcaaa    960
taccacctag gcgacaataa tccaatatat gattacattc tgatgaatac tgcagtatta    1020
tactgcctgt cccaagggca ccaaaactgg aaggaaggta ttatcaaagc cgaggagtca    1080
attcacagcg ggaatgcctt gagatcgcta gaacatttca ttgattcagt atcttcccttt    1140 taa                                                                  1143
```

<210> SEQ ID NO 36
<211> LENGTH: 1779
<212> TYPE: DNA
<213> ORGANISM: Saccharomyces cerevisiae
<220> FEATURE:
<223> OTHER INFORMATION: TAT2 gene

<400> SEQUENCE: 36

| | | | | | |
|---|---|---|---|---|---|
| atgaccgaag | atttcatcag | tagcgtcaaa | aggtcaaatg | aagagcttaa agagagaaaa | 60 |
| tctaattttg | ggtttgtaga | gtacaagtca | aaacaactta | cctccagtag ctcacacaac | 120 |
| tccaactctt | cacaccatga | tgacgacaac | cagcacggta | aagaaacat ctttcagcgt | 180 |
| tgtgtggatt | cttttaaatc | ccctctggat | gggtctttcg | acacctccaa tctgaaaaga | 240 |
| acactgaaac | ctcgtcattt | aataatgatc | gcaataggag | gtagtatagg tactggtctt | 300 |
| ttcgtgggtt | cagggaaggc | tatagcggaa | ggcggaccac | ttggcgttgt gatcggatgg | 360 |
| gccattgcgg | gtagccaaat | aataggtact | atacatgggt | taggagagat cacggtaaga | 420 |
| tttccagtag | tcggtgcgtt | tgccaactac | ggcacccgtt | tcttggaccc gagcattagt | 480 |
| tttgtagtct | ccactatata | cgtgctacag | tggttctttg | tcctaccct agagattatt | 540 |
| gctgcggcga | tgaccgtgca | atactggaac | agttctatcg | atccggtaat atgggtcgca | 600 |
| attttctatg | ccgtcatcgt | ctcaatcaat | ttgtttggag | ttaggggttt cggagaagct | 660 |
| gaattcgcct | tctcaactat | taaggcaatc | actgtctgtg | gcttcataat cttatgtgta | 720 |
| gtcttgatct | gcggcggagg | acccgatcac | gaattcattg | gtgctaaata ctggcatgat | 780 |
| cctggctgcc | tggcaaacgg | gttcctgga | gtcttgagtg | tccttgtcgt tgcgtcatac | 840 |
| agcctaggag | gcatagaaat | gacttgctta | gcctctgggg | aaacggaccc aaagggactt | 900 |
| ccctcagcta | taaaacaggt | tttctggcgt | attttgtttt | tcttcttaat ttctttaact | 960 |
| ctagtgggat | ttttagttcc | ttacaccaac | caaaatctac | taggtggctc ctctgtcgat | 1020 |
| aatagtccct | tcgttatcgc | gattaagcta | caccatatca | aagctcttcc gtctattgtt | 1080 |
| aacgcagtta | tccttatttc | cgtgctatcc | gtgggtaaca | gttgcatctt tgccagctcc | 1140 |
| agaactctgt | gtagcatggc | acatcaagga | ctgataccgt | ggtggttcgg ctatattgac | 1200 |
| agagctggca | gaccccctggt | tgggattatg | gccaattctc | ttttcggctt attggcgttc | 1260 |
| cttgttaaat | ctggctccat | gagtgaggtg | tttaattggc | tgatggctat agccggactg | 1320 |
| gcgacatgta | ttgtgtggtt | atctataaat | ctttcccata | aagattccg tcttgcaatg | 1380 |
| aaggcccaag | gaaagtccct | ggatgaactt | gaattcgtaa | gcgcggttgg tatatgggga | 1440 |
| tctgcttatt | ccgcacttat | caattgctta | atacttattg | ctcaattta ttgctcttta | 1500 |
| tggccaatcg | ggggttggac | atccggaaaa | gagagggcaa | agatttctt tcagaattat | 1560 |
| ctttgcgccc | tgattatgtt | atttatattc | atcgtccata | agatctatta taaatgtcaa | 1620 |
| acgggaaagt | ggtggggtgt | taagctctcg | aaggacatcg | acctagagac cgacaggaag | 1680 |
| gacatagaca | tcgaaatagt | taaacaagaa | atcgctgaaa | agaagatgta tttggactcc | 1740 |
| agaccttggt | acgtgaggca | gtttcatttt | tggtgctaa | | 1779 |